(12) United States Patent
Zupancic et al.

(10) Patent No.: US 9,850,547 B2
(45) Date of Patent: *Dec. 26, 2017

(54) BIOSENSOR SYSTEM FOR THE RAPID DETECTION OF ANALYTES

(71) Applicant: FUNDAMENTAL SOLUTIONS CORPORATION, Easton, PA (US)

(72) Inventors: Thomas J. Zupancic, Powell, OH (US); Lingchun Zeng, Upper Arlington, OH (US); Srikanth Vedamoorthy, New Albany, OH (US); Joel S. Lwande, Athens, OH (US); Joseph D. Kittle, The Plains, OH (US); Min Mo, Dublin, OH (US)

(73) Assignee: Fundamental Solutions Corporation, Easton, PA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/642,867

(22) Filed: Jul. 6, 2017

(65) Prior Publication Data
US 2017/0306423 A1 Oct. 26, 2017

Related U.S. Application Data

(62) Division of application No. 15/086,769, filed on Mar. 31, 2016, now Pat. No. 9,752,199.

(60) Provisional application No. 62/140,920, filed on Mar. 31, 2015, provisional application No. 62/245,595, filed on Oct. 23, 2015.

(51) Int. Cl.
| | |
|---|---|
| *G01N 33/53* | (2006.01) |
| *C12Q 1/68* | (2006.01) |
| *C07K 14/735* | (2006.01) |
| *G01N 33/536* | (2006.01) |
| *G01N 33/569* | (2006.01) |
| *C07K 14/725* | (2006.01) |
| *C07K 14/36* | (2006.01) |
| *C07K 14/315* | (2006.01) |
| *C07K 16/12* | (2006.01) |
| *G01N 33/50* | (2006.01) |

(52) U.S. Cl.
CPC .......... *C12Q 1/6897* (2013.01); *C07K 14/315* (2013.01); *C07K 14/36* (2013.01); *C07K 14/7051* (2013.01); *C07K 14/70535* (2013.01); *C07K 16/12* (2013.01); *G01N 33/5047* (2013.01); *G01N 33/536* (2013.01); *G01N 33/56916* (2013.01); *C07K 2317/52* (2013.01); *C07K 2319/22* (2013.01); *C07K 2319/60* (2013.01); *G01N 2333/245* (2013.01)

(58) Field of Classification Search
None
See application file for complete search history.

(56) References Cited

U.S. PATENT DOCUMENTS

| | | | | |
|---|---|---|---|---|
| 8,420,327 | B2 * | 4/2013 | Ellis | G01N 33/542 435/7.1 |
| 9,291,549 | B2 | 3/2016 | Schwoebel et al. | |
| 9,442,118 | B2 * | 9/2016 | Huang | G01N 33/542 |
| 2002/0168367 | A1 | 11/2002 | Larrick et al. | |
| 2005/0202442 | A1 | 9/2005 | Morris et al. | |
| 2009/0068757 | A1 * | 3/2009 | Lehmann | B01J 19/0046 436/172 |
| 2009/0304696 | A1 | 12/2009 | Lawson et al. | |
| 2013/0089554 | A1 | 4/2013 | Blankenship et al. | |
| 2014/0273020 | A1 | 9/2014 | Zupancic et al. | |
| 2014/0335603 | A1 | 11/2014 | Zupancic et al. | |
| 2016/0289775 | A1 | 10/2016 | Zupancic et al. | |

FOREIGN PATENT DOCUMENTS

WO  WO 2016/149109 A1  9/2016

OTHER PUBLICATIONS

International Search Report and Written Opinion dated Oct. 19, 2016 for Application No. PCT/US2016/025219, 22 pgs.
U.S. Appl. No. 15/642,867, filed Jul. 6, 2017, Zupancic et al.
U.S. Appl. No. 15/642,900, filed Jul. 6, 2017, Zupancic et al.
U.S. Appl. No. 62/140,920, filed Mar. 31, 2015, Zupancic et al.
U.S. Appl. No. 62/245,595, filed Oct. 23, 2015, Zupancic et al.

\* cited by examiner

*Primary Examiner* — Changhwa J Cheu
(74) *Attorney, Agent, or Firm* — Frost Brown Todd LLC

(57) ABSTRACT

A system, device, and method for rapid detection of analytes that includes a living, engineered biosensor cell that is typically a component of the mammalian immune system; a reporter protein that is engineered into and expressed by the living, engineered biosensor cell, wherein the reporter protein emits a detectable signal in response to certain predetermined changes in the cytosol of the living, engineered cell; a signal transduction pathway expressed by the living, engineered biosensor cell, wherein the signal transduction pathway controls a biological process within the cytosol of the living, engineered biosensor cell, and wherein the biochemical process, when it occurs, causes the reporter protein to emit a detectable signal; at least one type of detector molecule that is adapted to bind to a specific analyte; at least one analyte that binds to the detector molecule that is specific to that analyte; a plurality of non-antibody signal transducing elements that are either expressed by the living, engineered biosensor cell or that actively bind to a receptor or a receptor component expressed by the living, engineered biosensor cell, wherein each signal transducing element is adapted to receive a detector molecule.

15 Claims, 4 Drawing Sheets

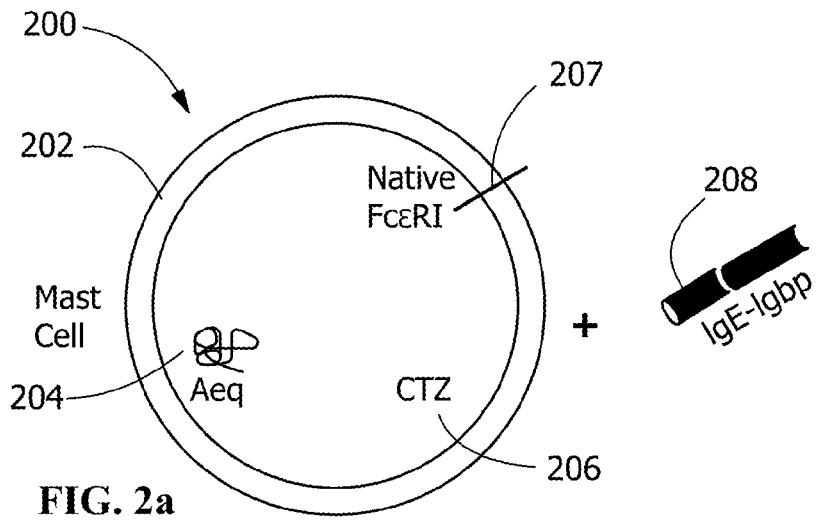
FIG. 2a
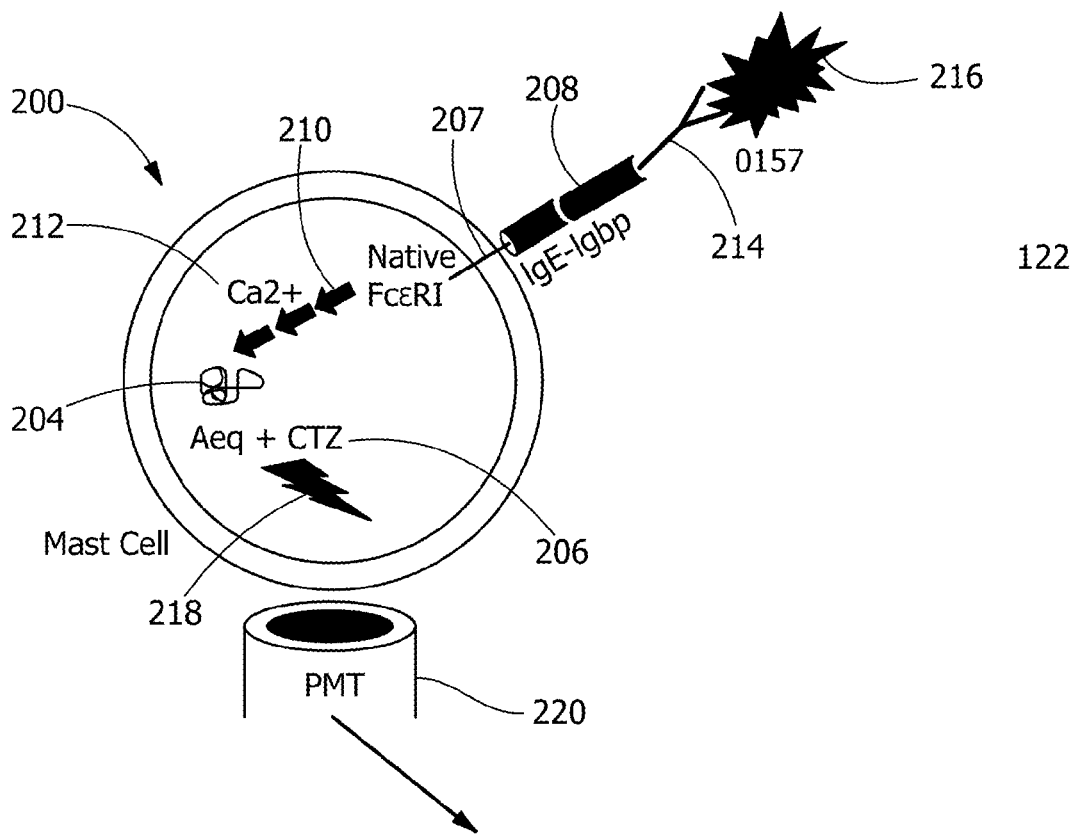
FIG. 2b
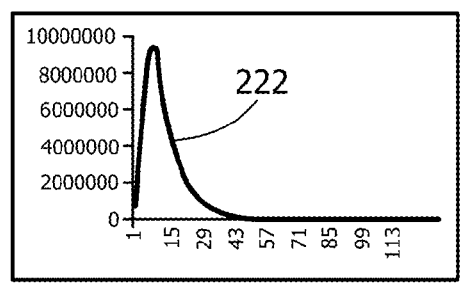

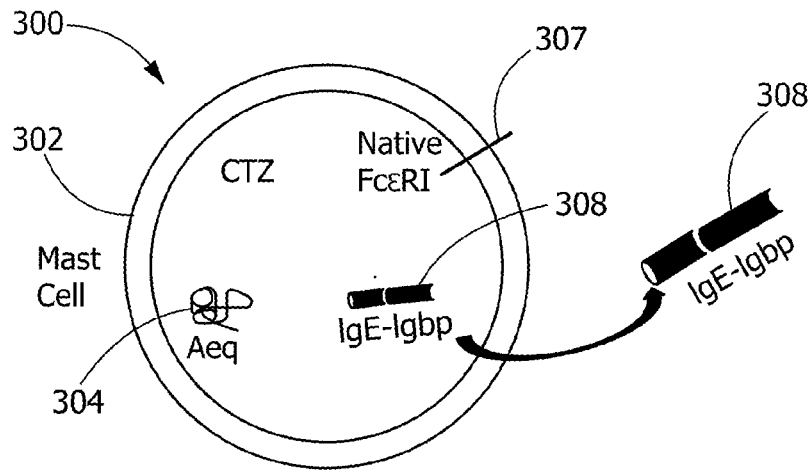
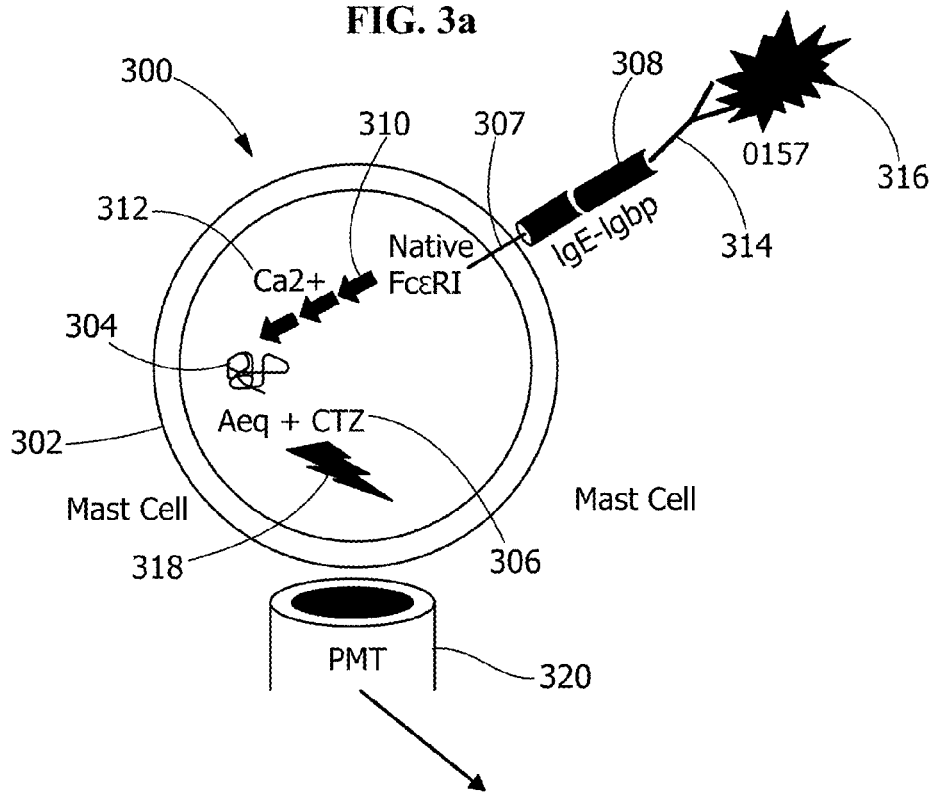
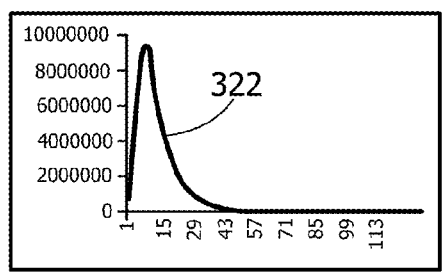
FIG. 3a
FIG. 3b

SEQUENCE LISTING

```
<160> NUMBER OF SEQ ID NOS: 19

<210> SEQ ID NO 1
<211> LENGTH: 1929
<212> TYPE: DNA
<213> ORGANISM: Artificial Sequence
<220> FEATURE:
<223> OTHER INFORMATION: Chimeric Protein:   BBP-IgM
<220> FEATURE:
<221> NAME/KEY: CDS
<222> LOCATION: (1)..(1929)

<400> SEQUENCE: 1 atg gtg ctg cag acg caa gtg ttt atc tcc ctg ctg ctc tgg atc agc      48
Met Val Leu Gln Thr Gln Val Phe Ile Ser Leu Leu Leu Trp Ile Ser
1               5                   10                  15 gga gcg tac ggc act tac aag ctg gtg atc aac ggt aaa acc ttg aag      96
Gly Ala Tyr Gly Thr Tyr Lys Leu Val Ile Asn Gly Lys Thr Leu Lys
            20                  25                  30 ggt gag acc acc act gag gca gtc gac gcc gcc act gcc gag aag gtc     144
Gly Glu Thr Thr Thr Glu Ala Val Asp Ala Ala Thr Ala Glu Lys Val
        35                  40                  45 ttt aaa cag tat gcc aat gat aac ggc gtg gac ggc gag tgg acc tac     192
Phe Lys Gln Tyr Ala Asn Asp Asn Gly Val Asp Gly Glu Trp Thr Tyr
    50                  55                  60 gat gac gcc act aag aca ttc act gtg act gaa aag ccc gag gtg att     240
Asp Asp Ala Thr Lys Thr Phe Thr Val Thr Glu Lys Pro Glu Val Ile
65                  70                  75                  80 gac gcg tcc gaa ttg aca cct gcg gtg acc acc tac aaa ctg gtt atc     288
Asp Ala Ser Glu Leu Thr Pro Ala Val Thr Thr Tyr Lys Leu Val Ile
                85                  90                  95 aac ggc aag act ctg aag ggc gag acc acc aca gag gca gtc gat gcc     336
Asn Gly Lys Thr Leu Lys Gly Glu Thr Thr Thr Glu Ala Val Asp Ala
```

```
                100               105                110
    gcc acc gcc gag aag gtc ttc aag caa tat gcc aac gac aac ggg gtg      384
    Ala Thr Ala Glu Lys Val Phe Lys Gln Tyr Ala Asn Asp Asn Gly Val
            115                 120                 125 gac ggg gag tgg acc tac gat gat gcc acc aag acc ttc acc gtg acc      432
    Asp Gly Glu Trp Thr Tyr Asp Asp Ala Thr Lys Thr Phe Thr Val Thr
    130                 135                 140 gag aag ccc gaa gtg atc gat gcg agt gaa ctg act ccc gcc gtg aca      480
    Glu Lys Pro Glu Val Ile Asp Ala Ser Glu Leu Thr Pro Ala Val Thr
    145                 150                 155                 160 ggt tct gct tct ggt tct ggt ggt tca gca tca gca cca act ttg ttt      528
    Gly Ser Ala Ser Gly Ser Gly Gly Ser Ala Ser Ala Pro Thr Leu Phe
                    165                 170                 175 cca ctt gtc tca tgt gag aac tcg cca tcg gat acc tcg agc gta gcg      576
    Pro Leu Val Ser Cys Glu Asn Ser Pro Ser Asp Thr Ser Ser Val Ala
                180                 185                 190 gtc gga tgt ctc gct caa gac ttt ctt ccg gac agc atc acg ttt tca      624
    Val Gly Cys Leu Ala Gln Asp Phe Leu Pro Asp Ser Ile Thr Phe Ser
            195                 200                 205 tgg aag tat aag aac aat tcg gat att tcg agc acg cga gga ttt ccc      672
    Trp Lys Tyr Lys Asn Asn Ser Asp Ile Ser Ser Thr Arg Gly Phe Pro
        210                 215                 220 agc gta ttg aga ggg gga aag tac gcg gca aca agc cag gtg ctg ctc      720
    Ser Val Leu Arg Gly Gly Lys Tyr Ala Ala Thr Ser Gln Val Leu Leu
    225                 230                 235                 240 cca agc aag gat gtg atg cag ggc act gac gag cat gta gta tgc aag      768
    Pro Ser Lys Asp Val Met Gln Gly Thr Asp Glu His Val Val Cys Lys
                    245                 250                 255 gta cag cac ccc aat gga aac aag gaa aag aat gtc cct ctg cct gta      816
    Val Gln His Pro Asn Gly Asn Lys Glu Lys Asn Val Pro Leu Pro Val
                260                 265                 270 att gcc gag ctc cct cct aaa gtg tca gtg ttc gtg ccg ccc aga gat      864
    Ile Ala Glu Leu Pro Pro Lys Val Ser Val Phe Val Pro Pro Arg Asp
            275                 280                 285 ggg ttc ttt gga aac ccg cga tcg aag tcg aaa ctg atc tgc cag gcc      912
    Gly Phe Phe Gly Asn Pro Arg Ser Lys Ser Lys Leu Ile Cys Gln Ala
        290                 295                 300 acg gga ttc agc cct cgg cag att caa gtg tcg tgg ttg cgg gag gga      960
    Thr Gly Phe Ser Pro Arg Gln Ile Gln Val Ser Trp Leu Arg Glu Gly
    305                 310                 315                 320 aaa cag gtg gga tcg ggg gtg acc aca gac cag gtg cag gcg gag gct     1008
    Lys Gln Val Gly Ser Gly Val Thr Thr Asp Gln Val Gln Ala Glu Ala
                    325                 330                 335 aaa gaa agc ggt ccc acc aca tat aag gtc act tcc acc ctt act att     1056
    Lys Glu Ser Gly Pro Thr Thr Tyr Lys Val Thr Ser Thr Leu Thr Ile
                340                 345                 350 aag gaa tcg gat tgg ttg tca cag tcg atg ttc aca tgt aga gtc gat     1104
    Lys Glu Ser Asp Trp Leu Ser Gln Ser Met Phe Thr Cys Arg Val Asp
            355                 360                 365 cat cgc gga ctc acg ttt caa cag aac gcg tca tca atg tgt gta ccc     1152
    His Arg Gly Leu Thr Phe Gln Gln Asn Ala Ser Ser Met Cys Val Pro
        370                 375                 380 gat caa gat acg gcg atc aga gta ttc gcc att ccg cct agc ttc gca     1200
    Asp Gln Asp Thr Ala Ile Arg Val Phe Ala Ile Pro Pro Ser Phe Ala
    385                 390                 395                 400 tcc att ttt ctc acc aaa agc aca aag ctg aca tgt ctt gtg aca gac     1248
    Ser Ile Phe Leu Thr Lys Ser Thr Lys Leu Thr Cys Leu Val Thr Asp
                    405                 410                 415 ctc aca acg tac gat tca gtc aca att tca tgg acc agg cag aat ggg     1296
```

-continued

| | | |
|---|---|---|
| Leu Thr Thr Tyr Asp Ser Val Thr Ile Ser Trp Thr Arg Gln Asn Gly<br>420                                425                            430 | | |

```
gag gcg gta aag acg cac acc aac att tcg gaa agc cat ccc aac gcc      1344
Glu Ala Val Lys Thr His Thr Asn Ile Ser Glu Ser His Pro Asn Ala
            435                 440                 445 acg ttt tcg gcg gtc ggg gag gca tcg att tgt gag gac gat tgg aat      1392
Thr Phe Ser Ala Val Gly Glu Ala Ser Ile Cys Glu Asp Asp Trp Asn
450                 455                 460 tca ggg gag cgc ttc aca tgc acg gtc act cac acg gat ctc cca tcc      1440
Ser Gly Glu Arg Phe Thr Cys Thr Val Thr His Thr Asp Leu Pro Ser
465                 470                 475                 480 ccg ttg aag cag aca atc tcg cga ccc aaa ggt gtc gca ctg cac agg      1488
Pro Leu Lys Gln Thr Ile Ser Arg Pro Lys Gly Val Ala Leu His Arg
                485                 490                 495 ccc gac gtc tac ctc ctg cct cct gcc agg gaa cag ctc aac ctc cgg      1536
Pro Asp Val Tyr Leu Leu Pro Pro Ala Arg Glu Gln Leu Asn Leu Arg
            500                 505                 510 gaa tca gca acg atc acg tgt ctt gta acc ggg ttt tca ccg gct gac      1584
Glu Ser Ala Thr Ile Thr Cys Leu Val Thr Gly Phe Ser Pro Ala Asp
515                 520                 525 gtc ttt gtc caa tgg atg cag cgg gga caa ccc ttg tca cca gag aag      1632
Val Phe Val Gln Trp Met Gln Arg Gly Gln Pro Leu Ser Pro Glu Lys
530                 535                 540 tat gtg aca tca gcg ccc atg ccc gag cca cag gct ccg ggt agg tat      1680
Tyr Val Thr Ser Ala Pro Met Pro Glu Pro Gln Ala Pro Gly Arg Tyr
545                 550                 555                 560 ttt gcc cat tcc atc ctc act gtg tcc gag gaa gag tgg aac acc ggc      1728
Phe Ala His Ser Ile Leu Thr Val Ser Glu Glu Glu Trp Asn Thr Gly
                565                 570                 575 gaa acg tac acg tgc gtc gta gca cac gaa gcg ttg ccc aat aga gtg      1776
Glu Thr Tyr Thr Cys Val Val Ala His Glu Ala Leu Pro Asn Arg Val
            580                 585                 590 act gag aga act gta gat aag tcc act gag ggc gaa gta agc gcg gat      1824
Thr Glu Arg Thr Val Asp Lys Ser Thr Glu Gly Glu Val Ser Ala Asp
595                 600                 605 gaa gaa ggt ttc gaa aac ttg tgg gct aca gcg agc acg ttt atc gtg      1872
Glu Glu Gly Phe Glu Asn Leu Trp Ala Thr Ala Ser Thr Phe Ile Val
610                 615                 620 ttg ttc ttg ctt tca ctc ttc tac tcc aca act gta acc ctg ttc aag      1920
Leu Phe Leu Leu Ser Leu Phe Tyr Ser Thr Thr Val Thr Leu Phe Lys
625                 630                 635                 640 gtc aag tag                                                          1929
Val Lys <210> SEQ ID NO 2
<211> LENGTH: 642
<212> TYPE: PRT
<213> ORGANISM: Artificial Sequence
<220> FEATURE:
<223> OTHER INFORMATION: Synthetic Construct

<400> SEQUENCE: 2

Met Val Leu Gln Thr Gln Val Phe Ile Ser Leu Leu Leu Trp Ile Ser
1               5                   10                  15

Gly Ala Tyr Gly Thr Tyr Lys Leu Val Ile Asn Gly Lys Thr Leu Lys
            20                  25                  30

Gly Glu Thr Thr Thr Glu Ala Val Asp Ala Ala Thr Ala Glu Lys Val
        35                  40                  45

Phe Lys Gln Tyr Ala Asn Asp Asn Gly Val Asp Gly Glu Trp Thr Tyr
50                  55                  60
```

-continued

```
Asp Asp Ala Thr Lys Thr Phe Thr Val Thr Glu Lys Pro Glu Val Ile
 65                  70                  75                  80

Asp Ala Ser Glu Leu Thr Pro Ala Val Thr Thr Tyr Lys Leu Val Ile
                 85                  90                  95

Asn Gly Lys Thr Leu Lys Gly Glu Thr Thr Glu Ala Val Asp Ala
            100                 105                 110

Ala Thr Ala Glu Lys Val Phe Lys Gln Tyr Ala Asn Asp Asn Gly Val
            115                 120                 125

Asp Gly Glu Trp Thr Tyr Asp Asp Ala Thr Lys Thr Phe Thr Val Thr
130                 135                 140

Glu Lys Pro Glu Val Ile Asp Ala Ser Glu Leu Thr Pro Ala Val Thr
145                 150                 155                 160

Gly Ser Ala Ser Gly Ser Gly Ser Ala Ser Ala Pro Thr Leu Phe
                165                 170                 175

Pro Leu Val Ser Cys Glu Asn Ser Pro Ser Asp Thr Ser Ser Val Ala
                180                 185                 190

Val Gly Cys Leu Ala Gln Asp Phe Leu Pro Asp Ser Ile Thr Phe Ser
            195                 200                 205

Trp Lys Tyr Lys Asn Asn Ser Asp Ile Ser Ser Thr Arg Gly Phe Pro
210                 215                 220

Ser Val Leu Arg Gly Gly Lys Tyr Ala Ala Thr Ser Gln Val Leu Leu
225                 230                 235                 240

Pro Ser Lys Asp Val Met Gln Gly Thr Asp Glu His Val Val Cys Lys
                245                 250                 255

Val Gln His Pro Asn Gly Asn Lys Glu Lys Asn Val Pro Leu Pro Val
            260                 265                 270

Ile Ala Glu Leu Pro Pro Lys Val Ser Val Phe Val Pro Pro Arg Asp
            275                 280                 285

Gly Phe Phe Gly Asn Pro Arg Ser Lys Ser Lys Leu Ile Cys Gln Ala
290                 295                 300

Thr Gly Phe Ser Pro Arg Gln Ile Gln Val Ser Trp Leu Arg Glu Gly
305                 310                 315                 320

Lys Gln Val Gly Ser Gly Val Thr Thr Asp Gln Val Gln Ala Glu Ala
                325                 330                 335

Lys Glu Ser Gly Pro Thr Thr Tyr Lys Val Thr Ser Thr Leu Thr Ile
            340                 345                 350

Lys Glu Ser Asp Trp Leu Ser Gln Ser Met Phe Thr Cys Arg Val Asp
            355                 360                 365

His Arg Gly Leu Thr Phe Gln Gln Asn Ala Ser Ser Met Cys Val Pro
            370                 375                 380

Asp Gln Asp Thr Ala Ile Arg Val Phe Ala Ile Pro Pro Ser Phe Ala
385                 390                 395                 400

Ser Ile Phe Leu Thr Lys Ser Thr Lys Leu Thr Cys Leu Val Thr Asp
                405                 410                 415

Leu Thr Thr Tyr Asp Ser Val Thr Ile Ser Trp Thr Arg Gln Asn Gly
            420                 425                 430

Glu Ala Val Lys Thr His Thr Asn Ile Ser Glu Ser His Pro Asn Ala
            435                 440                 445

Thr Phe Ser Ala Val Gly Glu Ala Ser Ile Cys Glu Asp Asp Trp Asn
            450                 455                 460

Ser Gly Glu Arg Phe Thr Cys Thr Val Thr His Thr Asp Leu Pro Ser
465                 470                 475                 480
```

```
Pro Leu Lys Gln Thr Ile Ser Arg Pro Lys Gly Val Ala Leu His Arg
                485                 490                 495

Pro Asp Val Tyr Leu Leu Pro Ala Arg Glu Gln Leu Asn Leu Arg
        500                 505                 510

Glu Ser Ala Thr Ile Thr Cys Leu Val Thr Gly Phe Ser Pro Ala Asp
            515                 520                 525

Val Phe Val Gln Trp Met Gln Arg Gly Gln Pro Leu Ser Pro Glu Lys
        530                 535                 540

Tyr Val Thr Ser Ala Pro Met Pro Glu Pro Gln Ala Pro Gly Arg Tyr
545                 550                 555                 560

Phe Ala His Ser Ile Leu Thr Val Ser Glu Glu Glu Trp Asn Thr Gly
                565                 570                 575

Glu Thr Tyr Thr Cys Val Val Ala His Glu Ala Leu Pro Asn Arg Val
            580                 585                 590

Thr Glu Arg Thr Val Asp Lys Ser Thr Gly Glu Val Ser Ala Asp
        595                 600                 605

Glu Glu Gly Phe Glu Asn Leu Trp Ala Thr Ala Ser Thr Phe Ile Val
        610                 615                 620

Leu Phe Leu Leu Ser Leu Phe Tyr Ser Thr Thr Val Thr Leu Phe Lys
625                 630                 635                 640

Val Lys

<210> SEQ ID NO 3
<211> LENGTH: 1884
<212> TYPE: DNA
<213> ORGANISM: Artificial Sequence
<220> FEATURE:
<223> OTHER INFORMATION: Chimeric Protein: BBP-IgAB
<220> FEATURE:
<221> NAME/KEY: CDS
<222> LOCATION: (1)..(1884)

<400> SEQUENCE: 3 atg ccg ggt gga ccc gga gtg ctc cag gca ttg cct gca acc atc ttc       48
Met Pro Gly Gly Pro Gly Val Leu Gln Ala Leu Pro Ala Thr Ile Phe
1               5                   10                  15 ctg ctg ttc ttg ttg tcc gcc gtc tac ctt gga cct ggt tgc cag gca       96
Leu Leu Phe Leu Leu Ser Ala Val Tyr Leu Gly Pro Gly Cys Gln Ala
            20                  25                  30 act tac aag ctg gtg atc aac ggt aaa acc ttg aag ggt gag acc acc      144
Thr Tyr Lys Leu Val Ile Asn Gly Lys Thr Leu Lys Gly Glu Thr Thr
        35                  40                  45 act gag gca gtc gac gcc gcc act gcc gag aag gtc ttt aaa cag tat      192
Thr Glu Ala Val Asp Ala Ala Thr Ala Glu Lys Val Phe Lys Gln Tyr
    50                  55                  60 gcc aat gat aac ggc gtg gac ggc gag tgg acc tac gat gac gcc act      240
Ala Asn Asp Asn Gly Val Asp Gly Glu Trp Thr Tyr Asp Asp Ala Thr
65                  70                  75                  80 aag aca ttc act gtg act gaa aag ccc gag gtg att gac gcg tcc gaa      288
Lys Thr Phe Thr Val Thr Glu Lys Pro Glu Val Ile Asp Ala Ser Glu
                85                  90                  95 ttg aca cct gcg gtg acc acc tac aaa ctg gtt atc aac ggc aag act      336
Leu Thr Pro Ala Val Thr Thr Tyr Lys Leu Val Ile Asn Gly Lys Thr
            100                 105                 110 ctg aag ggc gag acc acc aca gag gca gtc gat gcc gcc acc gcc gag      384
Leu Lys Gly Glu Thr Thr Thr Glu Ala Val Asp Ala Ala Thr Ala Glu
        115                 120                 125 aag gtc ttc aag caa tat gcc aac gac aac ggg gtg gac ggg gag tgg      432
Lys Val Phe Lys Gln Tyr Ala Asn Asp Asn Gly Val Asp Gly Glu Trp
```

-continued

```
                130                 135                 140
acc tac gat gat gcc acc aag acc ttc acc gtg acc gag aag ccc gaa     480
Thr Tyr Asp Asp Ala Thr Lys Thr Phe Thr Val Thr Glu Lys Pro Glu
145                 150                 155                 160 gtg atc gat gcg agt gaa ctg act ccc gcc gtg aca ggt tct gct tcg     528
Val Ile Asp Ala Ser Glu Leu Thr Pro Ala Val Thr Gly Ser Ala Ser
                165                 170                 175 ggc tca gga ctg tgg atg cat aag gtg cct gca tcg ctc atg gtg agc     576
Gly Ser Gly Leu Trp Met His Lys Val Pro Ala Ser Leu Met Val Ser
        180                 185                 190 ctg ggc gaa gat gca cat ttt cag tgt ccc cat aac agc tcc aac aac     624
Leu Gly Glu Asp Ala His Phe Gln Cys Pro His Asn Ser Ser Asn Asn
    195                 200                 205 gcg aac gtg acc tgg tgg cgg gtg ctc cat ggc aat tac acc tgg ccg     672
Ala Asn Val Thr Trp Trp Arg Val Leu His Gly Asn Tyr Thr Trp Pro
210                 215                 220 cct gaa ttt ctc gga ccg gga gag gac ccg aat ggg acc ctt atc atc     720
Pro Glu Phe Leu Gly Pro Gly Glu Asp Pro Asn Gly Thr Leu Ile Ile
225                 230                 235                 240 cag aac gtg aat aag tcc cac gga gga atc tac gtc tgc cgc gtg caa     768
Gln Asn Val Asn Lys Ser His Gly Gly Ile Tyr Val Cys Arg Val Gln
                245                 250                 255 gag gga aat gag agc tac caa cag tca tgc gga acg tac ctc cgc gtc     816
Glu Gly Asn Glu Ser Tyr Gln Gln Ser Cys Gly Thr Tyr Leu Arg Val
        260                 265                 270 cgg cag cca cca ccg agg ccg ttc ctc gat atg gga gag gga act aag     864
Arg Gln Pro Pro Pro Arg Pro Phe Leu Asp Met Gly Glu Gly Thr Lys
    275                 280                 285 aac cgg atc att acc gcc gaa ggc atc atc ctc ctc ttc tgc gcc gtc     912
Asn Arg Ile Ile Thr Ala Glu Gly Ile Ile Leu Leu Phe Cys Ala Val
290                 295                 300 gtg ccg ggg act ctg ctt ctg ttc cgg aaa agg tgg caa aac gaa aag     960
Val Pro Gly Thr Leu Leu Leu Phe Arg Lys Arg Trp Gln Asn Glu Lys
305                 310                 315                 320 ctg ggt ctg gac gct ggg gac gaa tac gag gat gaa aac ttg tac gag    1008
Leu Gly Leu Asp Ala Gly Asp Glu Tyr Glu Asp Glu Asn Leu Tyr Glu
                325                 330                 335 ggc ctg aat ctg gac gat tgc tcg atg tat gag gac att agc aga gga    1056
Gly Leu Asn Leu Asp Asp Cys Ser Met Tyr Glu Asp Ile Ser Arg Gly
        340                 345                 350 ctg cag ggt acc tac caa gac gtg gga agc ctg aac atc ggg gat gtg    1104
Leu Gln Gly Thr Tyr Gln Asp Val Gly Ser Leu Asn Ile Gly Asp Val
    355                 360                 365 cag ctc gag aaa cca agg aaa aga aga gct agc gaa gga cgc gga tca    1152
Gln Leu Glu Lys Pro Arg Lys Arg Arg Ala Ser Glu Gly Arg Gly Ser
370                 375                 380 ctg ctt act tgc ggc gat gtc gaa gaa aat ccc gga cca atg gcc aga    1200
Leu Leu Thr Cys Gly Asp Val Glu Glu Asn Pro Gly Pro Met Ala Arg
385                 390                 395                 400 ttg gcg ctg tcg ccg gtc cct tcg cac tgg atg gtg gcc ctg ctg ctc    1248
Leu Ala Leu Ser Pro Val Pro Ser His Trp Met Val Ala Leu Leu Leu
                405                 410                 415 ttg ctt tcg gcg gct gag ccg gtg cca gcg gct aga tcg gag gac cgc    1296
Leu Leu Ser Ala Ala Glu Pro Val Pro Ala Ala Arg Ser Glu Asp Arg
        420                 425                 430 tac aga aat ccg aag ggt tcc gct tgc tca cgc atc tgg caa tca cca    1344
Tyr Arg Asn Pro Lys Gly Ser Ala Cys Ser Arg Ile Trp Gln Ser Pro
    435                 440                 445 cgc ttc atc gcg cgc aaa cgc ggc ttc act gtc aag atg cac tgc tat    1392
```

```
Arg Phe Ile Ala Arg Lys Arg Gly Phe Thr Val Lys Met His Cys Tyr
    450                 455                 460 atg aac tcg gcc agc ggg aat gtg tcg tgg ctg tgg aag cag gaa atg      1440
Met Asn Ser Ala Ser Gly Asn Val Ser Trp Leu Trp Lys Gln Glu Met
465                 470                 475                 480 gac gag aat ccg cag caa ctg aaa ctg gag aag ggc cgg atg gaa gaa      1488
Asp Glu Asn Pro Gln Gln Leu Lys Leu Glu Lys Gly Arg Met Glu Glu
                    485                 490                 495 tcc cag aat gag tcg ctg gcc acc ctt act atc caa ggt atc cgg ttt      1536
Ser Gln Asn Glu Ser Leu Ala Thr Leu Thr Ile Gln Gly Ile Arg Phe
                500                 505                 510 gaa gat aac ggg atc tac ttc tgt caa cag aag tgt aac aac act tca      1584
Glu Asp Asn Gly Ile Tyr Phe Cys Gln Gln Lys Cys Asn Asn Thr Ser
            515                 520                 525 gag gtg tac cag gga tgc ggc acc gaa ctc cgc gtc atg gga ttc tcc      1632
Glu Val Tyr Gln Gly Cys Gly Thr Glu Leu Arg Val Met Gly Phe Ser
        530                 535                 540 acc ctc gcc caa ctg aag cag cgc aac acg ctg aag gac ggc atc att      1680
Thr Leu Ala Gln Leu Lys Gln Arg Asn Thr Leu Lys Asp Gly Ile Ile
545                 550                 555                 560 atg atc cag acc ctg ctg atc atc ctg ttc atc att gtg ccg atc ttt      1728
Met Ile Gln Thr Leu Leu Ile Ile Leu Phe Ile Ile Val Pro Ile Phe
                565                 570                 575 ctg ctc ttg gat aag gac gac tcg aaa gcc gga atg gaa gag gac cac      1776
Leu Leu Leu Asp Lys Asp Asp Ser Lys Ala Gly Met Glu Glu Asp His
                580                 585                 590 acg tac gaa ggt ctg gac atc gac caa act gcg act tac gag gac att      1824
Thr Tyr Glu Gly Leu Asp Ile Asp Gln Thr Ala Thr Tyr Glu Asp Ile
            595                 600                 605 gtg acc ctc cgg act ggc gaa gtc aag tgg tcc gtg ggt gaa cac cct      1872
Val Thr Leu Arg Thr Gly Glu Val Lys Trp Ser Val Gly Glu His Pro
        610                 615                 620 gga cag gaa tag                                                       1884
Gly Gln Glu
625

<210> SEQ ID NO 4
<211> LENGTH: 627
<212> TYPE: PRT
<213> ORGANISM: Artificial Sequence
<220> FEATURE:
<223> OTHER INFORMATION: Synthetic Construct

<400> SEQUENCE: 4

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Thr Tyr Lys Leu Val Ile Asn Gly Lys Thr Leu Lys Gly Glu Thr Thr
        35                  40                  45

Thr Glu Ala Val Asp Ala Ala Thr Ala Glu Lys Val Phe Lys Gln Tyr
    50                  55                  60

Ala Asn Asp Asn Gly Val Asp Gly Glu Trp Thr Tyr Asp Asp Ala Thr
65                  70                  75                  80

Lys Thr Phe Thr Val Thr Glu Lys Pro Glu Val Ile Asp Ala Ser Glu
                85                  90                  95

Leu Thr Pro Ala Val Thr Thr Tyr Lys Leu Val Ile Asn Gly Lys Thr
            100                 105                 110

Leu Lys Gly Glu Thr Thr Thr Glu Ala Val Asp Ala Ala Thr Ala Glu
```

-continued

```
            115                 120                 125
Lys Val Phe Lys Gln Tyr Ala Asn Asp Asn Gly Val Asp Gly Glu Trp
            130                 135                 140
Thr Tyr Asp Asp Ala Thr Lys Thr Phe Thr Val Thr Glu Lys Pro Glu
145                 150                 155                 160
Val Ile Asp Ala Ser Glu Leu Thr Pro Ala Val Thr Gly Ser Ala Ser
                    165                 170                 175
Gly Ser Gly Leu Trp Met His Lys Val Pro Ala Ser Leu Met Val Ser
                180                 185                 190
Leu Gly Glu Asp Ala His Phe Gln Cys Pro His Asn Ser Ser Asn Asn
            195                 200                 205
Ala Asn Val Thr Trp Trp Arg Val Leu His Gly Asn Tyr Thr Trp Pro
210                 215                 220
Pro Glu Phe Leu Gly Pro Gly Glu Asp Pro Asn Gly Thr Leu Ile Ile
225                 230                 235                 240
Gln Asn Val Asn Lys Ser His Gly Gly Ile Tyr Val Cys Arg Val Gln
                    245                 250                 255
Glu Gly Asn Glu Ser Tyr Gln Gln Ser Cys Gly Thr Tyr Leu Arg Val
                260                 265                 270
Arg Gln Pro Pro Pro Arg Pro Phe Leu Asp Met Gly Glu Gly Thr Lys
            275                 280                 285
Asn Arg Ile Ile Thr Ala Glu Gly Ile Ile Leu Leu Phe Cys Ala Val
290                 295                 300
Val Pro Gly Thr Leu Leu Leu Phe Arg Lys Arg Trp Gln Asn Glu Lys
305                 310                 315                 320
Leu Gly Leu Asp Ala Gly Asp Glu Tyr Glu Asp Glu Asn Leu Tyr Glu
                    325                 330                 335
Gly Leu Asn Leu Asp Asp Cys Ser Met Tyr Glu Asp Ile Ser Arg Gly
                340                 345                 350
Leu Gln Gly Thr Tyr Gln Asp Val Gly Ser Leu Asn Ile Gly Asp Val
            355                 360                 365
Gln Leu Glu Lys Pro Arg Lys Arg Arg Ala Ser Glu Gly Arg Gly Ser
370                 375                 380
Leu Leu Thr Cys Gly Asp Val Glu Glu Asn Pro Gly Pro Met Ala Arg
385                 390                 395                 400
Leu Ala Leu Ser Pro Val Pro Ser His Trp Met Val Ala Leu Leu Leu
                    405                 410                 415
Leu Leu Ser Ala Ala Glu Pro Val Pro Ala Ala Arg Ser Glu Asp Arg
                420                 425                 430
Tyr Arg Asn Pro Lys Gly Ser Ala Cys Ser Arg Ile Trp Gln Ser Pro
            435                 440                 445
Arg Phe Ile Ala Arg Lys Arg Gly Phe Thr Val Lys Met His Cys Tyr
450                 455                 460
Met Asn Ser Ala Ser Gly Asn Val Ser Trp Leu Trp Lys Gln Glu Met
465                 470                 475                 480
Asp Glu Asn Pro Gln Gln Leu Lys Leu Glu Lys Gly Arg Met Glu Glu
                    485                 490                 495
Ser Gln Asn Glu Ser Leu Ala Thr Leu Thr Ile Gln Gly Ile Arg Phe
                500                 505                 510
Glu Asp Asn Gly Ile Tyr Phe Cys Gln Gln Lys Cys Asn Asn Thr Ser
            515                 520                 525
Glu Val Tyr Gln Gly Cys Gly Thr Glu Leu Arg Val Met Gly Phe Ser
530                 535                 540
```

```
Thr Leu Ala Gln Leu Lys Gln Arg Asn Thr Leu Lys Asp Gly Ile Ile
545                 550                 555                 560

Met Ile Gln Thr Leu Leu Ile Ile Leu Phe Ile Ile Val Pro Ile Phe
            565                 570                 575

Leu Leu Leu Asp Lys Asp Ser Lys Ala Gly Met Glu Glu Asp His
        580                 585                 590

Thr Tyr Glu Gly Leu Asp Ile Asp Gln Thr Ala Thr Tyr Glu Asp Ile
        595                 600                 605

Val Thr Leu Arg Thr Gly Glu Val Lys Trp Ser Val Gly Glu His Pro
    610                 615                 620

Gly Gln Glu
625

<210> SEQ ID NO 5
<211> LENGTH: 936
<212> TYPE: DNA
<213> ORGANISM: Artificial Sequence
<220> FEATURE:
<223> OTHER INFORMATION: Chimeric Protein: BBP-CD3Z
<220> FEATURE:
<221> NAME/KEY: CDS
<222> LOCATION: (1)..(936)

<400> SEQUENCE: 5 atg aag tgg aag gcg ctt ttc acc gcg gcc atc ctg cag gca cag ttg     48
Met Lys Trp Lys Ala Leu Phe Thr Ala Ala Ile Leu Gln Ala Gln Leu
1               5                   10                  15 ccg att aca gag gca act tac aag ctg gtg atc aac ggt aaa acc ttg     96
Pro Ile Thr Glu Ala Thr Tyr Lys Leu Val Ile Asn Gly Lys Thr Leu
            20                  25                  30 aag ggt gag acc acc act gag gca gtc gac gcc gcc act gcc gag aag    144
Lys Gly Glu Thr Thr Thr Glu Ala Val Asp Ala Ala Thr Ala Glu Lys
        35                  40                  45 gtc ttt aaa cag tat gcc aat gat aac ggc gtg gac ggc gag tgg acc    192
Val Phe Lys Gln Tyr Ala Asn Asp Asn Gly Val Asp Gly Glu Trp Thr
    50                  55                  60 tac gat gac gcc act aag aca ttc act gtg act gaa aag ccc gag gtg    240
Tyr Asp Asp Ala Thr Lys Thr Phe Thr Val Thr Glu Lys Pro Glu Val
65                  70                  75                  80 att gac gcg tcc gaa ttg aca cct gcg gtg acc acc tac aaa ctg gtt    288
Ile Asp Ala Ser Glu Leu Thr Pro Ala Val Thr Thr Tyr Lys Leu Val
                85                  90                  95 atc aac ggc aag act ctg aag ggc gag acc acc aca gag gca gtc gat    336
Ile Asn Gly Lys Thr Leu Lys Gly Glu Thr Thr Thr Glu Ala Val Asp
            100                 105                 110 gcc gcc acc gcc gag aag gtc ttc aag caa tat gcc aac gac aac ggg    384
Ala Ala Thr Ala Glu Lys Val Phe Lys Gln Tyr Ala Asn Asp Asn Gly
        115                 120                 125 gtg gac ggg gag tgg acc tac gat gat gcc acc aag acc ttc acc gtg    432
Val Asp Gly Glu Trp Thr Tyr Asp Asp Ala Thr Lys Thr Phe Thr Val
    130                 135                 140 acc gag aag ccc gaa gtg atc gat gcg agt gaa ctg act ccc gcc gtg    480
Thr Glu Lys Pro Glu Val Ile Asp Ala Ser Glu Leu Thr Pro Ala Val
145                 150                 155                 160 aca ggt tct gct tct ggt tct ggt cag agc ttt ggc ctg ctg gat ccc    528
Thr Gly Ser Ala Ser Gly Ser Gly Gln Ser Phe Gly Leu Leu Asp Pro
                165                 170                 175 aaa ctc tgc tac ctg ctg gat gga atc ctc ttc atc tat ggt gtc att    576
Lys Leu Cys Tyr Leu Leu Asp Gly Ile Leu Phe Ile Tyr Gly Val Ile
            180                 185                 190
```

```
ctc act gcc ttg ttc ctg aga gtg aag ttc agc agg agc gca gac gcc      624
Leu Thr Ala Leu Phe Leu Arg Val Lys Phe Ser Arg Ser Ala Asp Ala
        195                 200                 205 ccc gcg tac cag cag ggc cag aac cag ctc tat aac gag ctc aat cta      672
Pro Ala Tyr Gln Gln Gly Gln Asn Gln Leu Tyr Asn Glu Leu Asn Leu
    210                 215                 220 gga cga aga gag gag tac gat gtt ttg gac aag aga cgt ggc cgg gac      720
Gly Arg Arg Glu Glu Tyr Asp Val Leu Asp Lys Arg Arg Gly Arg Asp
225                 230                 235                 240 cct gag atg ggg gga aag ccg cag aga agg aag aac cct cag gaa ggc      768
Pro Glu Met Gly Gly Lys Pro Gln Arg Arg Lys Asn Pro Gln Glu Gly
            245                 250                 255 ctg tac aat gaa ctg cag aaa gat aag atg gcg gag gcc tac agt gag      816
Leu Tyr Asn Glu Leu Gln Lys Asp Lys Met Ala Glu Ala Tyr Ser Glu
        260                 265                 270 att ggg atg aaa ggc gag cgc cgg agg ggc aag ggg cac gat ggc ctt      864
Ile Gly Met Lys Gly Glu Arg Arg Arg Gly Lys Gly His Asp Gly Leu
    275                 280                 285 tac cag ggt ctc agt aca gcc acc aag gac acc tac gac gcc ctt cac      912
Tyr Gln Gly Leu Ser Thr Ala Thr Lys Asp Thr Tyr Asp Ala Leu His
290                 295                 300 atg cag gcc ctg ccc cct cgc taa                                      936
Met Gln Ala Leu Pro Pro Arg
305                 310

<210> SEQ ID NO 6
<211> LENGTH: 311
<212> TYPE: PRT
<213> ORGANISM: Artificial Sequence
<220> FEATURE:
<223> OTHER INFORMATION: Synthetic Construct

<400> SEQUENCE: 6

Met Lys Trp Lys Ala Leu Phe Thr Ala Ala Ile Leu Gln Ala Gln Leu
1               5                   10                  15

Pro Ile Thr Glu Ala Thr Tyr Lys Leu Val Ile Asn Gly Lys Thr Leu
            20                  25                  30

Lys Gly Glu Thr Thr Thr Glu Ala Val Asp Ala Ala Thr Ala Glu Lys
        35                  40                  45

Val Phe Lys Gln Tyr Ala Asn Asp Asn Gly Val Asp Gly Glu Trp Thr
    50                  55                  60

Tyr Asp Asp Ala Thr Lys Thr Phe Thr Val Thr Glu Lys Pro Glu Val
65                  70                  75                  80

Ile Asp Ala Ser Glu Leu Thr Pro Ala Val Thr Thr Tyr Lys Leu Val
                85                  90                  95

Ile Asn Gly Lys Thr Leu Lys Gly Glu Thr Thr Thr Glu Ala Val Asp
            100                 105                 110

Ala Ala Thr Ala Glu Lys Val Phe Lys Gln Tyr Ala Asn Asp Asn Gly
        115                 120                 125

Val Asp Gly Glu Trp Thr Tyr Asp Asp Ala Thr Lys Thr Phe Thr Val
    130                 135                 140

Thr Glu Lys Pro Glu Val Ile Asp Ala Ser Glu Leu Thr Pro Ala Val
145                 150                 155                 160

Thr Gly Ser Ala Ser Gly Ser Gly Gln Ser Phe Gly Leu Leu Asp Pro
                165                 170                 175

Lys Leu Cys Tyr Leu Leu Asp Gly Ile Leu Phe Ile Tyr Gly Val Ile
            180                 185                 190
```

-continued

```
Leu Thr Ala Leu Phe Leu Arg Val Lys Phe Ser Arg Ser Asp Ala
            195                 200                 205

Pro Ala Tyr Gln Gln Gly Gln Asn Gln Leu Tyr Asn Glu Leu Asn Leu
    210                 215                 220

Gly Arg Arg Glu Glu Tyr Asp Val Leu Asp Lys Arg Arg Gly Arg Asp
225                 230                 235                 240

Pro Glu Met Gly Gly Lys Pro Gln Arg Arg Lys Asn Pro Gln Glu Gly
                245                 250                 255

Leu Tyr Asn Glu Leu Gln Lys Asp Lys Met Ala Glu Ala Tyr Ser Glu
            260                 265                 270

Ile Gly Met Lys Gly Glu Arg Arg Arg Gly Lys Gly His Asp Gly Leu
        275                 280                 285

Tyr Gln Gly Leu Ser Thr Ala Thr Lys Asp Thr Tyr Asp Ala Leu His
    290                 295                 300

Met Gln Ala Leu Pro Pro Arg
305                 310

<210> SEQ ID NO 7
<211> LENGTH: 2340
<212> TYPE: DNA
<213> ORGANISM: Artificial Sequence
<220> FEATURE:
<223> OTHER INFORMATION: Chimeric Protein: FcgammaR1-IgM
<220> FEATURE:
<221> NAME/KEY: CDS
<222> LOCATION: (1)..(2340)

<400> SEQUENCE: 7 atg att ctt acc agc ttt gga gat gac atg tgg ctt cta aca act ctg      48
Met Ile Leu Thr Ser Phe Gly Asp Asp Met Trp Leu Leu Thr Thr Leu
 1               5                  10                  15 cta ctt tgg gtt cca gtc ggt ggg gaa gtg gtt aat gcc acc aag gct      96
Leu Leu Trp Val Pro Val Gly Gly Glu Val Val Asn Ala Thr Lys Ala
            20                  25                  30 gtg atc acc ttg cag cct cca tgg gtc agt att ttc cag aag gaa aat     144
Val Ile Thr Leu Gln Pro Pro Trp Val Ser Ile Phe Gln Lys Glu Asn
        35                  40                  45 gtc act tta tgg tgt gag ggg cct cac ctg cct gga gac agt tcc aca     192
Val Thr Leu Trp Cys Glu Gly Pro His Leu Pro Gly Asp Ser Ser Thr
    50                  55                  60 caa tgg ttt atc aac gga aca gcc gtt cag atc tcc acg cct agt tat     240
Gln Trp Phe Ile Asn Gly Thr Ala Val Gln Ile Ser Thr Pro Ser Tyr
65                  70                  75                  80 agc atc cca gag gcc agt ttt cag gac agt ggc gaa tac agg tgt cag     288
Ser Ile Pro Glu Ala Ser Phe Gln Asp Ser Gly Glu Tyr Arg Cys Gln
                85                  90                  95 ata ggt tcc tca atg cca agt gac cct gtg cag ttg caa atc cac aat     336
Ile Gly Ser Ser Met Pro Ser Asp Pro Val Gln Leu Gln Ile His Asn
            100                 105                 110 gat tgg ctg cta ctc cag gcc tcc cgc aga gtc ctc aca gaa gga gaa     384
Asp Trp Leu Leu Leu Gln Ala Ser Arg Arg Val Leu Thr Glu Gly Glu
        115                 120                 125 ccc ctg gcc ttg agg tgt cac gga tgg aag aat aaa ctg gtg tac aat     432
Pro Leu Ala Leu Arg Cys His Gly Trp Lys Asn Lys Leu Val Tyr Asn
    130                 135                 140 gtg gtt ttc tat aga aat gga aaa tcc ttt cag ttt tct tca gat tcg     480
Val Val Phe Tyr Arg Asn Gly Lys Ser Phe Gln Phe Ser Ser Asp Ser
145                 150                 155                 160 gag gtc gcc att ctg aaa acc aac ctg agt cac agc ggc atc tac cac     528
Glu Val Ala Ile Leu Lys Thr Asn Leu Ser His Ser Gly Ile Tyr His
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
|     |     |     |     | 165 |     |     |     |     | 170 |     |     |     |     | 175 |     |      |
| tgc | tca | ggc | acg | gga | aga | cac | cgc | tac | aca | tct | gca | gga | gtg | tcc | atc | 576  |
| Cys | Ser | Gly | Thr | Gly | Arg | His | Arg | Tyr | Thr | Ser | Ala | Gly | Val | Ser | Ile |      |
|     |     |     | 180 |     |     |     |     | 185 |     |     |     |     | 190 |     |     |      |
| acg | gtg | aaa | gag | ctg | ttt | acc | acg | cca | gtg | ctg | aga | gca | tcc | gtg | tca | 624  |
| Thr | Val | Lys | Glu | Leu | Phe | Thr | Thr | Pro | Val | Leu | Arg | Ala | Ser | Val | Ser |      |
|     |     |     | 195 |     |     |     |     | 200 |     |     |     |     | 205 |     |     |      |
| tct | ccc | ttc | ccg | gag | ggg | agt | ctg | gtc | acc | ctg | aac | tgt | gag | acg | aat | 672  |
| Ser | Pro | Phe | Pro | Glu | Gly | Ser | Leu | Val | Thr | Leu | Asn | Cys | Glu | Thr | Asn |      |
|     |     |     | 210 |     |     |     |     | 215 |     |     |     |     | 220 |     |     |      |
| ttg | ctc | ctg | cag | aga | ccc | ggc | tta | cag | ctt | cac | ttc | tcc | ttc | tac | gtg | 720  |
| Leu | Leu | Leu | Gln | Arg | Pro | Gly | Leu | Gln | Leu | His | Phe | Ser | Phe | Tyr | Val |      |
| 225 |     |     |     |     | 230 |     |     |     |     | 235 |     |     |     |     | 240 |      |
| ggc | agc | aag | atc | ctg | gag | tac | agg | aac | aca | tcc | tca | gag | tac | cat | ata | 768  |
| Gly | Ser | Lys | Ile | Leu | Glu | Tyr | Arg | Asn | Thr | Ser | Ser | Glu | Tyr | His | Ile |      |
|     |     |     |     | 245 |     |     |     |     | 250 |     |     |     |     | 255 |     |      |
| gca | agg | gcg | gaa | aga | gaa | gat | gct | gga | ttc | tac | tgg | tgt | gag | gta | gcc | 816  |
| Ala | Arg | Ala | Glu | Arg | Glu | Asp | Ala | Gly | Phe | Tyr | Trp | Cys | Glu | Val | Ala |      |
|     |     |     | 260 |     |     |     |     | 265 |     |     |     |     | 270 |     |     |      |
| acg | gag | gac | agc | agt | gtc | ctt | aag | cgc | agc | cct | gag | ttg | gag | ctc | caa | 864  |
| Thr | Glu | Asp | Ser | Ser | Val | Leu | Lys | Arg | Ser | Pro | Glu | Leu | Glu | Leu | Gln |      |
|     |     |     | 275 |     |     |     |     | 280 |     |     |     |     | 285 |     |     |      |
| gtg | ctt | ggt | ccc | cag | tca | tca | gct | cct | ggt | tct | gct | tct | ggt | tct | ggt | 912  |
| Val | Leu | Gly | Pro | Gln | Ser | Ser | Ala | Pro | Gly | Ser | Ala | Ser | Gly | Ser | Gly |      |
|     |     |     | 290 |     |     |     |     | 295 |     |     |     |     | 300 |     |     |      |
| ggt | tca | gca | tca | gca | cca | act | ttg | ttt | cca | ctt | gtc | tca | tgt | gag | aac | 960  |
| Gly | Ser | Ala | Ser | Ala | Pro | Thr | Leu | Phe | Pro | Leu | Val | Ser | Cys | Glu | Asn |      |
| 305 |     |     |     |     | 310 |     |     |     |     | 315 |     |     |     |     | 320 |      |
| tcg | cca | tcg | gat | acc | tcg | agc | gta | gcg | gtc | gga | tgt | ctc | gct | caa | gac | 1008 |
| Ser | Pro | Ser | Asp | Thr | Ser | Ser | Val | Ala | Val | Gly | Cys | Leu | Ala | Gln | Asp |      |
|     |     |     |     | 325 |     |     |     |     | 330 |     |     |     |     | 335 |     |      |
| ttt | ctt | ccg | gac | agc | atc | acg | ttt | tca | tgg | aag | tat | aag | aac | aat | tcg | 1056 |
| Phe | Leu | Pro | Asp | Ser | Ile | Thr | Phe | Ser | Trp | Lys | Tyr | Lys | Asn | Asn | Ser |      |
|     |     |     | 340 |     |     |     |     | 345 |     |     |     |     | 350 |     |     |      |
| gat | att | tcg | agc | acg | cga | gga | ttt | ccc | agc | gta | ttg | aga | ggg | gga | aag | 1104 |
| Asp | Ile | Ser | Ser | Thr | Arg | Gly | Phe | Pro | Ser | Val | Leu | Arg | Gly | Gly | Lys |      |
|     |     |     | 355 |     |     |     |     | 360 |     |     |     |     | 365 |     |     |      |
| tac | gcg | gca | aca | agc | cag | gtg | ctg | ctc | cca | agc | aag | gat | gtg | atg | cag | 1152 |
| Tyr | Ala | Ala | Thr | Ser | Gln | Val | Leu | Leu | Pro | Ser | Lys | Asp | Val | Met | Gln |      |
| 370 |     |     |     |     | 375 |     |     |     |     | 380 |     |     |     |     |     |      |
| ggc | act | gac | gag | cat | gta | gta | tgc | aag | gta | cag | cac | ccc | aat | gga | aac | 1200 |
| Gly | Thr | Asp | Glu | His | Val | Val | Cys | Lys | Val | Gln | His | Pro | Asn | Gly | Asn |      |
| 385 |     |     |     |     | 390 |     |     |     |     | 395 |     |     |     |     | 400 |      |
| aag | gaa | aag | aat | gtc | cct | ctg | cct | gta | att | gcc | gag | ctc | cct | cct | aaa | 1248 |
| Lys | Glu | Lys | Asn | Val | Pro | Leu | Pro | Val | Ile | Ala | Glu | Leu | Pro | Pro | Lys |      |
|     |     |     |     | 405 |     |     |     |     | 410 |     |     |     |     | 415 |     |      |
| gtg | tca | gtg | ttc | gtg | ccg | ccc | aga | gat | ggg | ttc | ttt | gga | aac | ccg | cga | 1296 |
| Val | Ser | Val | Phe | Val | Pro | Pro | Arg | Asp | Gly | Phe | Phe | Gly | Asn | Pro | Arg |      |
|     |     |     | 420 |     |     |     |     | 425 |     |     |     |     | 430 |     |     |      |
| tcg | aag | tcg | aaa | ctg | atc | tgc | cag | gcc | acg | gga | ttc | agc | cct | cgg | cag | 1344 |
| Ser | Lys | Ser | Lys | Leu | Ile | Cys | Gln | Ala | Thr | Gly | Phe | Ser | Pro | Arg | Gln |      |
|     |     |     | 435 |     |     |     |     | 440 |     |     |     |     | 445 |     |     |      |
| att | caa | gtg | tcg | tgg | ttg | cgg | gag | gga | aaa | cag | gtg | gga | tcg | ggg | gtg | 1392 |
| Ile | Gln | Val | Ser | Trp | Leu | Arg | Glu | Gly | Lys | Gln | Val | Gly | Ser | Gly | Val |      |
|     |     |     | 450 |     |     |     |     | 455 |     |     |     |     | 460 |     |     |      |
| acc | aca | gac | cag | gtg | cag | gcg | gag | gct | aaa | gaa | agc | ggt | ccc | acc | aca | 1440 |
| Thr | Thr | Asp | Gln | Val | Gln | Ala | Glu | Ala | Lys | Glu | Ser | Gly | Pro | Thr | Thr |      |
| 465 |     |     |     |     | 470 |     |     |     |     | 475 |     |     |     |     | 480 |      |
| tat | aag | gtc | act | tcc | acc | ctt | act | att | aag | gaa | tcg | gat | tgg | ttg | tca | 1488 |

```
                    Tyr Lys Val Thr Ser Thr Leu Thr Ile Lys Glu Ser Asp Trp Leu Ser
                                    485                 490                 495 cag tcg atg ttc aca tgt aga gtc gat cat cgc gga ctc acg ttt caa            1536
Gln Ser Met Phe Thr Cys Arg Val Asp His Arg Gly Leu Thr Phe Gln
            500                 505                 510 cag aac gcg tca tca atg tgt gta ccc gat caa gat acg gcg atc aga            1584
Gln Asn Ala Ser Ser Met Cys Val Pro Asp Gln Asp Thr Ala Ile Arg
        515                 520                 525 gta ttc gcc att ccg cct agc ttc gca tcc att ttt ctc acc aaa agc            1632
Val Phe Ala Ile Pro Pro Ser Phe Ala Ser Ile Phe Leu Thr Lys Ser
    530                 535                 540 aca aag ctg aca tgt ctt gtg aca gac ctc aca acg tac gat tca gtc            1680
Thr Lys Leu Thr Cys Leu Val Thr Asp Leu Thr Thr Tyr Asp Ser Val
545                 550                 555                 560 aca att tca tgg acc agg cag aat ggg gag gcg gta aag acg cac acc            1728
Thr Ile Ser Trp Thr Arg Gln Asn Gly Glu Ala Val Lys Thr His Thr
                565                 570                 575 aac att tcg gaa agc cat ccc aac gcc acg ttt tcg gcg gtc ggg gag            1776
Asn Ile Ser Glu Ser His Pro Asn Ala Thr Phe Ser Ala Val Gly Glu
            580                 585                 590 gca tcg att tgt gag gac gat tgg aat tca ggg gag cgc ttc aca tgc            1824
Ala Ser Ile Cys Glu Asp Asp Trp Asn Ser Gly Glu Arg Phe Thr Cys
        595                 600                 605 acg gtc act cac acg gat ctc cca tcc ccg ttg aag cag aca atc tcg            1872
Thr Val Thr His Thr Asp Leu Pro Ser Pro Leu Lys Gln Thr Ile Ser
    610                 615                 620 cga ccc aaa ggt gtc gca ctg cac agg ccc gac gtc tac ctc ctg cct            1920
Arg Pro Lys Gly Val Ala Leu His Arg Pro Asp Val Tyr Leu Leu Pro
625                 630                 635                 640 cct gcc agg gaa cag ctc aac ctc cgg gaa tca gca acg atc acg tgt            1968
Pro Ala Arg Glu Gln Leu Asn Leu Arg Glu Ser Ala Thr Ile Thr Cys
                645                 650                 655 ctt gta acc ggg ttt tca ccg gct gac gtc ttt gtc caa tgg atg cag            2016
Leu Val Thr Gly Phe Ser Pro Ala Asp Val Phe Val Gln Trp Met Gln
            660                 665                 670 cgg gga caa ccc ttg tca cca gag aag tat gtg aca tca gcg ccc atg            2064
Arg Gly Gln Pro Leu Ser Pro Glu Lys Tyr Val Thr Ser Ala Pro Met
        675                 680                 685 ccc gag cca cag gct ccg ggt agg tat ttt gcc cat tcc atc ctc act            2112
Pro Glu Pro Gln Ala Pro Gly Arg Tyr Phe Ala His Ser Ile Leu Thr
    690                 695                 700 gtg tcc gag gaa gag tgg aac acc ggc gaa acg tac acg tgc gtc gta            2160
Val Ser Glu Glu Glu Trp Asn Thr Gly Glu Thr Tyr Thr Cys Val Val
705                 710                 715                 720 gca cac gaa gcg ttg ccc aat aga gtg act gag aga act gta gat aag            2208
Ala His Glu Ala Leu Pro Asn Arg Val Thr Glu Arg Thr Val Asp Lys
                725                 730                 735 tcc act gag ggc gaa gta agc gcg gat gaa gaa ggt ttc gaa aac ttg            2256
Ser Thr Glu Gly Glu Val Ser Ala Asp Glu Glu Gly Phe Glu Asn Leu
            740                 745                 750 tgg gct aca gcg agc acg ttt atc gtg ttg ttc ttg ctt tca ctc ttc            2304
Trp Ala Thr Ala Ser Thr Phe Ile Val Leu Phe Leu Leu Ser Leu Phe
        755                 760                 765 tac tcc aca act gta acc ctg ttc aag gtc aag tag                            2340
Tyr Ser Thr Thr Val Thr Leu Phe Lys Val Lys
    770                 775

<210> SEQ ID NO 8
<211> LENGTH: 779
<212> TYPE: PRT
```

<213> ORGANISM: Artificial Sequence
<220> FEATURE:
<223> OTHER INFORMATION: Synthetic Construct

<400> SEQUENCE: 8

Met Ile Leu Thr Ser Phe Gly Asp Asp Met Trp Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
            35                  40                  45

Val Thr Leu Trp Cys Glu Gly Pro His Leu Pro Gly Asp Ser Ser Thr
        50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125

Pro Leu Ala Leu Arg Cys His Gly Trp Lys Asn Lys Leu Val Tyr Asn
    130                 135                 140

Val Val Phe Tyr Arg Asn Gly Lys Ser Phe Gln Phe Ser Ser Asp Ser
145                 150                 155                 160

Glu Val Ala Ile Leu Lys Thr Asn Leu Ser His Ser Gly Ile Tyr His
                165                 170                 175

Cys Ser Gly Thr Gly Arg His Arg Tyr Thr Ser Ala Gly Val Ser Ile
            180                 185                 190

Thr Val Lys Glu Leu Phe Thr Thr Pro Val Leu Arg Ala Ser Val Ser
        195                 200                 205

Ser Pro Phe Pro Glu Gly Ser Leu Val Thr Leu Asn Cys Glu Thr Asn
    210                 215                 220

Leu Leu Leu Gln Arg Pro Gly Leu Gln Leu His Phe Ser Phe Tyr Val
225                 230                 235                 240

Gly Ser Lys Ile Leu Glu Tyr Arg Asn Thr Ser Ser Glu Tyr His Ile
                245                 250                 255

Ala Arg Ala Glu Arg Glu Asp Ala Gly Phe Tyr Trp Cys Glu Val Ala
            260                 265                 270

Thr Glu Asp Ser Ser Val Leu Lys Arg Ser Pro Glu Leu Glu Leu Gln
        275                 280                 285

Val Leu Gly Pro Gln Ser Ser Ala Pro Gly Ser Ala Ser Gly Ser Gly
    290                 295                 300

Gly Ser Ala Ser Ala Pro Thr Leu Phe Pro Leu Val Ser Cys Glu Asn
305                 310                 315                 320

Ser Pro Ser Asp Thr Ser Ser Val Ala Val Gly Cys Leu Ala Gln Asp
                325                 330                 335

Phe Leu Pro Asp Ser Ile Thr Phe Ser Trp Lys Tyr Lys Asn Asn Ser
            340                 345                 350

Asp Ile Ser Ser Thr Arg Gly Phe Pro Ser Val Leu Arg Gly Gly Lys
        355                 360                 365

Tyr Ala Ala Thr Ser Gln Val Leu Leu Pro Ser Lys Asp Val Met Gln
    370                 375                 380

Gly Thr Asp Glu His Val Val Cys Lys Val Gln His Pro Asn Gly Asn

```
            385                 390                 395                 400
Lys Glu Lys Asn Val Pro Leu Pro Val Ile Ala Glu Leu Pro Pro Lys
                405                 410                 415

Val Ser Val Phe Val Pro Pro Arg Asp Gly Phe Phe Gly Asn Pro Arg
            420                 425                 430

Ser Lys Ser Lys Leu Ile Cys Gln Ala Thr Gly Phe Ser Pro Arg Gln
        435                 440                 445

Ile Gln Val Ser Trp Leu Arg Glu Gly Lys Gln Val Gly Ser Gly Val
450                 455                 460

Thr Thr Asp Gln Val Gln Ala Glu Ala Lys Glu Ser Gly Pro Thr Thr
465                 470                 475                 480

Tyr Lys Val Thr Ser Thr Leu Thr Ile Lys Glu Ser Asp Trp Leu Ser
                485                 490                 495

Gln Ser Met Phe Thr Cys Arg Val Asp His Arg Gly Leu Thr Phe Gln
                500                 505                 510

Gln Asn Ala Ser Ser Met Cys Val Pro Asp Gln Asp Thr Ala Ile Arg
        515                 520                 525

Val Phe Ala Ile Pro Pro Ser Phe Ala Ser Ile Phe Leu Thr Lys Ser
530                 535                 540

Thr Lys Leu Thr Cys Leu Val Thr Asp Leu Thr Thr Tyr Asp Ser Val
545                 550                 555                 560

Thr Ile Ser Trp Thr Arg Gln Asn Gly Glu Ala Val Lys Thr His Thr
                565                 570                 575

Asn Ile Ser Glu Ser His Pro Asn Ala Thr Phe Ser Ala Val Gly Glu
                580                 585                 590

Ala Ser Ile Cys Glu Asp Asp Trp Asn Ser Gly Glu Arg Phe Thr Cys
        595                 600                 605

Thr Val Thr His Thr Asp Leu Pro Ser Pro Leu Lys Gln Thr Ile Ser
610                 615                 620

Arg Pro Lys Gly Val Ala Leu His Arg Pro Asp Val Tyr Leu Leu Pro
625                 630                 635                 640

Pro Ala Arg Glu Gln Leu Asn Leu Arg Glu Ser Ala Thr Ile Thr Cys
                645                 650                 655

Leu Val Thr Gly Phe Ser Pro Ala Asp Val Phe Val Gln Trp Met Gln
                660                 665                 670

Arg Gly Gln Pro Leu Ser Pro Glu Lys Tyr Val Thr Ser Ala Pro Met
        675                 680                 685

Pro Glu Pro Gln Ala Pro Gly Arg Tyr Phe Ala His Ser Ile Leu Thr
690                 695                 700

Val Ser Glu Glu Glu Trp Asn Thr Gly Glu Thr Tyr Thr Cys Val Val
705                 710                 715                 720

Ala His Glu Ala Leu Pro Asn Arg Val Thr Glu Arg Thr Val Asp Lys
                725                 730                 735

Ser Thr Glu Gly Glu Val Ser Ala Asp Glu Glu Gly Phe Glu Asn Leu
            740                 745                 750

Trp Ala Thr Ala Ser Thr Phe Ile Val Leu Phe Leu Leu Ser Leu Phe
            755                 760                 765

Tyr Ser Thr Thr Val Thr Leu Phe Lys Val Lys
        770                 775

<210> SEQ ID NO 9
<211> LENGTH: 2259
<212> TYPE: DNA
<213> ORGANISM: Artificial Sequence
```

```
<220> FEATURE:
<223> OTHER INFORMATION: Chimeric Protein: FcgammaR1-IgAB
<220> FEATURE:
<221> NAME/KEY: CDS
<222> LOCATION: (1)..(2259)

<400> SEQUENCE: 9 atg att ctt acc agc ttt gga gat gac atg tgg ctt cta aca act ctg      48
Met Ile Leu Thr Ser Phe Gly Asp Asp Met Trp Leu Leu Thr Thr Leu
1               5                   10                  15 cta ctt tgg gtt cca gtc ggt ggg gaa gtg gtt aat gcc acc aag gct      96
Leu Leu Trp Val Pro Val Gly Gly Glu Val Val Asn Ala Thr Lys Ala
            20                  25                  30 gtg atc acc ttg cag cct cca tgg gtc agt att ttc cag aag gaa aat     144
Val Ile Thr Leu Gln Pro Pro Trp Val Ser Ile Phe Gln Lys Glu Asn
        35                  40                  45 gtc act tta tgg tgt gag ggg cct cac ctg cct gga gac agt tcc aca     192
Val Thr Leu Trp Cys Glu Gly Pro His Leu Pro Gly Asp Ser Ser Thr
    50                  55                  60 caa tgg ttt atc aac gga aca gcc gtt cag atc tcc acg cct agt tat     240
Gln Trp Phe Ile Asn Gly Thr Ala Val Gln Ile Ser Thr Pro Ser Tyr
65                  70                  75                  80 agc atc cca gag gcc agt ttt cag gac agt ggc gaa tac agg tgt cag     288
Ser Ile Pro Glu Ala Ser Phe Gln Asp Ser Gly Glu Tyr Arg Cys Gln
                85                  90                  95 ata ggt tcc tca atg cca agt gac cct gtg cag ttg caa atc cac aat     336
Ile Gly Ser Ser Met Pro Ser Asp Pro Val Gln Leu Gln Ile His Asn
            100                 105                 110 gat tgg ctg cta ctc cag gcc tcc cgc aga gtc ctc aca gaa gga gaa     384
Asp Trp Leu Leu Leu Gln Ala Ser Arg Arg Val Leu Thr Glu Gly Glu
        115                 120                 125 ccc ctg gcc ttg agg tgt cac gga tgg aag aat aaa ctg gtg tac aat     432
Pro Leu Ala Leu Arg Cys His Gly Trp Lys Asn Lys Leu Val Tyr Asn
    130                 135                 140 gtg gtt ttc tat aga aat gga aaa tcc ttt cag ttt tct tca gat tcg     480
Val Val Phe Tyr Arg Asn Gly Lys Ser Phe Gln Phe Ser Ser Asp Ser
145                 150                 155                 160 gag gtc gcc att ctg aaa acc aac ctg agt cac agc ggc atc tac cac     528
Glu Val Ala Ile Leu Lys Thr Asn Leu Ser His Ser Gly Ile Tyr His
                165                 170                 175 tgc tca ggc acg gga aga cac cgc tac aca tct gca gga gtg tcc atc     576
Cys Ser Gly Thr Gly Arg His Arg Tyr Thr Ser Ala Gly Val Ser Ile
            180                 185                 190 acg gtg aaa gag ctg ttt acc acg cca gtg ctg aga gca tcc gtg tca     624
Thr Val Lys Glu Leu Phe Thr Thr Pro Val Leu Arg Ala Ser Val Ser
        195                 200                 205 tct ccc ttc ccg gag ggg agt ctg gtc acc ctg aac tgt gag acg aat     672
Ser Pro Phe Pro Glu Gly Ser Leu Val Thr Leu Asn Cys Glu Thr Asn
    210                 215                 220 ttg ctc ctg cag aga ccc ggc tta cag ctt cac ttc tcc ttc tac gtg     720
Leu Leu Leu Gln Arg Pro Gly Leu Gln Leu His Phe Ser Phe Tyr Val
225                 230                 235                 240 ggc agc aag atc ctg gag tac agg aac aca tcc tca gag tac cat ata     768
Gly Ser Lys Ile Leu Glu Tyr Arg Asn Thr Ser Ser Glu Tyr His Ile
                245                 250                 255 gca agg gcg gaa aga gaa gat gct gga ttc tac tgg tgt gag gta gcc     816
Ala Arg Ala Glu Arg Glu Asp Ala Gly Phe Tyr Trp Cys Glu Val Ala
            260                 265                 270 acg gag gac agc agt gtc ctt aag cgc agc cct gag ttg gag ctc caa     864
Thr Glu Asp Ser Ser Val Leu Lys Arg Ser Pro Glu Leu Glu Leu Gln
        275                 280                 285
```

| | | | | | | | | | | | | | | | | |
|---|---|---|---|---|---|---|---|---|---|---|---|---|---|---|---|---|
| gtg | ctt | ggt | ccc | cag | tca | tca | gct | cct | ggt | tct | gct | tcg | ggc | tca | gga | 912 |
| Val | Leu | Gly | Pro | Gln | Ser | Ser | Ala | Pro | Gly | Ser | Ala | Ser | Gly | Ser | Gly | |
| | | 290 | | | | 295 | | | | 300 | | | | | | |
| ctg | tgg | atg | cat | aag | gtg | cct | gca | tcg | ctc | atg | gtg | agc | ctg | ggc | gaa | 960 |
| Leu | Trp | Met | His | Lys | Val | Pro | Ala | Ser | Leu | Met | Val | Ser | Leu | Gly | Glu | |
| 305 | | | | | 310 | | | | | 315 | | | | | 320 | |
| gat | gca | cat | ttt | cag | tgt | ccc | cat | aac | agc | tcc | aac | aac | gcg | aac | gtg | 1008 |
| Asp | Ala | His | Phe | Gln | Cys | Pro | His | Asn | Ser | Ser | Asn | Asn | Ala | Asn | Val | |
| | | | | 325 | | | | | 330 | | | | | 335 | | |
| acc | tgg | tgg | cgg | gtg | ctc | cat | ggc | aat | tac | acc | tgg | ccg | cct | gaa | ttt | 1056 |
| Thr | Trp | Trp | Arg | Val | Leu | His | Gly | Asn | Tyr | Thr | Trp | Pro | Pro | Glu | Phe | |
| | | | 340 | | | | | 345 | | | | | 350 | | | |
| ctc | gga | ccg | gga | gag | gac | ccg | aat | ggg | acc | ctt | atc | atc | cag | aac | gtg | 1104 |
| Leu | Gly | Pro | Gly | Glu | Asp | Pro | Asn | Gly | Thr | Leu | Ile | Ile | Gln | Asn | Val | |
| | | 355 | | | | | 360 | | | | | 365 | | | | |
| aat | aag | tcc | cac | gga | gga | atc | tac | gtc | tgc | cgc | gtg | caa | gag | gga | aat | 1152 |
| Asn | Lys | Ser | His | Gly | Gly | Ile | Tyr | Val | Cys | Arg | Val | Gln | Glu | Gly | Asn | |
| | 370 | | | | | 375 | | | | | 380 | | | | | |
| gag | agc | tac | caa | cag | tca | tgc | gga | acg | tac | ctc | cgc | gtc | cgg | cag | cca | 1200 |
| Glu | Ser | Tyr | Gln | Gln | Ser | Cys | Gly | Thr | Tyr | Leu | Arg | Val | Arg | Gln | Pro | |
| 385 | | | | | 390 | | | | | 395 | | | | | 400 | |
| cca | ccg | agg | ccg | ttc | ctc | gat | atg | gga | gag | gga | act | aag | aac | cgg | atc | 1248 |
| Pro | Pro | Arg | Pro | Phe | Leu | Asp | Met | Gly | Glu | Gly | Thr | Lys | Asn | Arg | Ile | |
| | | | | 405 | | | | | 410 | | | | | 415 | | |
| att | acc | gcc | gaa | ggc | atc | atc | ctc | ctc | ttc | tgc | gcc | gtc | gtg | ccg | ggg | 1296 |
| Ile | Thr | Ala | Glu | Gly | Ile | Ile | Leu | Leu | Phe | Cys | Ala | Val | Val | Pro | Gly | |
| | | | 420 | | | | | 425 | | | | | 430 | | | |
| act | ctg | ctt | ctg | ttc | cgg | aaa | agg | tgg | caa | aac | gaa | aag | ctg | ggt | ctg | 1344 |
| Thr | Leu | Leu | Leu | Phe | Arg | Lys | Arg | Trp | Gln | Asn | Glu | Lys | Leu | Gly | Leu | |
| | | 435 | | | | | 440 | | | | | 445 | | | | |
| gac | gct | ggg | gac | gaa | tac | gag | gat | gaa | aac | ttg | tac | gag | ggc | ctg | aat | 1392 |
| Asp | Ala | Gly | Asp | Glu | Tyr | Glu | Asp | Glu | Asn | Leu | Tyr | Glu | Gly | Leu | Asn | |
| | 450 | | | | | 455 | | | | | 460 | | | | | |
| ctg | gac | gat | tgc | tcg | atg | tat | gag | gac | att | agc | aga | gga | ctg | cag | ggt | 1440 |
| Leu | Asp | Asp | Cys | Ser | Met | Tyr | Glu | Asp | Ile | Ser | Arg | Gly | Leu | Gln | Gly | |
| 465 | | | | | 470 | | | | | 475 | | | | | 480 | |
| acc | tac | caa | gac | gtg | gga | agc | ctg | aac | atc | ggg | gat | gtg | cag | ctc | gag | 1488 |
| Thr | Tyr | Gln | Asp | Val | Gly | Ser | Leu | Asn | Ile | Gly | Asp | Val | Gln | Leu | Glu | |
| | | | | 485 | | | | | 490 | | | | | 495 | | |
| aaa | cca | agg | aaa | aga | aga | gct | agc | gaa | gga | cgc | gga | tca | ctg | ctt | act | 1536 |
| Lys | Pro | Arg | Lys | Arg | Arg | Ala | Ser | Glu | Gly | Arg | Gly | Ser | Leu | Leu | Thr | |
| | | | 500 | | | | | 505 | | | | | 510 | | | |
| tgc | ggc | gat | gtc | gaa | gaa | aat | ccc | gga | cca | atg | gcc | aga | ttg | gcg | ctg | 1584 |
| Cys | Gly | Asp | Val | Glu | Glu | Asn | Pro | Gly | Pro | Met | Ala | Arg | Leu | Ala | Leu | |
| | | 515 | | | | | 520 | | | | | 525 | | | | |
| tcg | ccg | gtc | cct | tcg | cac | tgg | atg | gtg | gcc | ctg | ctc | ttg | ctt | tcg | | 1632 |
| Ser | Pro | Val | Pro | Ser | His | Trp | Met | Val | Ala | Leu | Leu | Leu | Leu | Ser | | |
| | 530 | | | | | 535 | | | | | 540 | | | | | |
| gcg | gct | gag | ccg | gtg | cca | gcg | gct | aga | tcg | gag | gac | cgc | tac | aga | aat | 1680 |
| Ala | Ala | Glu | Pro | Val | Pro | Ala | Ala | Arg | Ser | Glu | Asp | Arg | Tyr | Arg | Asn | |
| 545 | | | | | 550 | | | | | 555 | | | | | 560 | |
| ccg | aag | ggt | tcc | gct | tgc | tca | cgc | atc | tgg | caa | tca | cca | cgc | ttc | atc | 1728 |
| Pro | Lys | Gly | Ser | Ala | Cys | Ser | Arg | Ile | Trp | Gln | Ser | Pro | Arg | Phe | Ile | |
| | | | | 565 | | | | | 570 | | | | | 575 | | |
| gcg | cgc | aaa | cgc | ggc | ttc | act | gtc | aag | atg | cac | tgc | tat | atg | aac | tcg | 1776 |
| Ala | Arg | Lys | Arg | Gly | Phe | Thr | Val | Lys | Met | His | Cys | Tyr | Met | Asn | Ser | |
| | | | 580 | | | | | 585 | | | | | 590 | | | |
| gcc | agc | ggg | aat | gtg | tcg | tgg | ctg | tgg | aag | cag | gaa | atg | gac | gag | aat | 1824 |
| Ala | Ser | Gly | Asn | Val | Ser | Trp | Leu | Trp | Lys | Gln | Glu | Met | Asp | Glu | Asn | |

```
                     595                 600                 605
ccg cag caa ctg aaa ctg gag aag ggc cgg atg gaa gaa tcc cag aat      1872
Pro Gln Gln Leu Lys Leu Glu Lys Gly Arg Met Glu Glu Ser Gln Asn
610                 615                 620 gag tcg ctg gcc acc ctt act atc caa ggt atc cgg ttt gaa gat aac      1920
Glu Ser Leu Ala Thr Leu Thr Ile Gln Gly Ile Arg Phe Glu Asp Asn
625                 630                 635                 640 ggg atc tac ttc tgt caa cag aag tgt aac aac act tca gag gtg tac      1968
Gly Ile Tyr Phe Cys Gln Gln Lys Cys Asn Asn Thr Ser Glu Val Tyr
                645                 650                 655 cag gga tgc ggc acc gaa ctc cgc gtc atg gga ttc tcc acc ctc gcc      2016
Gln Gly Cys Gly Thr Glu Leu Arg Val Met Gly Phe Ser Thr Leu Ala
            660                 665                 670 caa ctg aag cag cgc aac acg ctg aag gac ggc atc att atg atc cag      2064
Gln Leu Lys Gln Arg Asn Thr Leu Lys Asp Gly Ile Ile Met Ile Gln
        675                 680                 685 acc ctg ctg atc atc ctg ttc atc att gtg ccg atc ttt ctc ctc ttg      2112
Thr Leu Leu Ile Ile Leu Phe Ile Ile Val Pro Ile Phe Leu Leu Leu
690                 695                 700 gat aag gac gac tcg aaa gcc gga atg gaa gag gac cac acg tac gaa      2160
Asp Lys Asp Asp Ser Lys Ala Gly Met Glu Glu Asp His Thr Tyr Glu
705                 710                 715                 720 ggt ctg gac atc gac caa act gcg act tac gag gac att gtg acc ctc      2208
Gly Leu Asp Ile Asp Gln Thr Ala Thr Tyr Glu Asp Ile Val Thr Leu
                725                 730                 735 cgg act ggc gaa gtc aag tgg tcc gtg ggt gaa cac cct gga cag gaa      2256
Arg Thr Gly Glu Val Lys Trp Ser Val Gly Glu His Pro Gly Gln Glu
            740                 745                 750 tag                                                                  2259

<210> SEQ ID NO 10
<211> LENGTH: 752
<212> TYPE: PRT
<213> ORGANISM: Artificial Sequence
<220> FEATURE:
<223> OTHER INFORMATION: Synthetic Construct

<400> SEQUENCE: 10

Met Ile Leu Thr Ser Phe Gly Asp Asp Met Trp Leu Thr Thr Leu
1               5                   10                  15

Leu Leu Trp Val Pro Val Gly Gly Glu Val Val Asn Ala Thr Lys Ala
            20                  25                  30

Val Ile Thr Leu Gln Pro Pro Trp Val Ser Ile Phe Gln Lys Glu Asn
        35                  40                  45

Val Thr Leu Trp Cys Glu Gly Pro His Leu Pro Gly Asp Ser Ser Thr
    50                  55                  60

Gln Trp Phe Ile Asn Gly Thr Ala Val Gln Ile Ser Thr Pro Ser Tyr
65                  70                  75                  80

Ser Ile Pro Glu Ala Ser Phe Gln Asp Ser Gly Glu Tyr Arg Cys Gln
                85                  90                  95

Ile Gly Ser Ser Met Pro Ser Asp Pro Val Gln Leu Gln Ile His Asn
            100                 105                 110

Asp Trp Leu Leu Leu Gln Ala Ser Arg Arg Val Leu Thr Glu Gly Glu
        115                 120                 125

Pro Leu Ala Leu Arg Cys His Gly Trp Lys Asn Lys Leu Val Tyr Asn
    130                 135                 140

Val Val Phe Tyr Arg Asn Gly Lys Ser Phe Gln Phe Ser Ser Asp Ser
145                 150                 155                 160
```

```
Glu Val Ala Ile Leu Lys Thr Asn Leu Ser His Ser Gly Ile Tyr His
                165                 170                 175
Cys Ser Gly Thr Gly Arg His Arg Tyr Thr Ser Ala Gly Val Ser Ile
            180                 185                 190
Thr Val Lys Glu Leu Phe Thr Thr Pro Val Leu Arg Ala Ser Val Ser
        195                 200                 205
Ser Pro Phe Pro Glu Gly Ser Leu Val Thr Leu Asn Cys Glu Thr Asn
    210                 215                 220
Leu Leu Leu Gln Arg Pro Gly Leu Gln Leu His Phe Ser Phe Tyr Val
225                 230                 235                 240
Gly Ser Lys Ile Leu Glu Tyr Arg Asn Thr Ser Ser Glu Tyr His Ile
                245                 250                 255
Ala Arg Ala Glu Arg Glu Asp Ala Gly Phe Tyr Trp Cys Glu Val Ala
            260                 265                 270
Thr Glu Asp Ser Ser Val Leu Lys Arg Ser Pro Glu Leu Glu Leu Gln
        275                 280                 285
Val Leu Gly Pro Gln Ser Ser Ala Pro Gly Ser Ala Ser Gly Ser Gly
    290                 295                 300
Leu Trp Met His Lys Val Pro Ala Ser Leu Met Val Ser Leu Gly Glu
305                 310                 315                 320
Asp Ala His Phe Gln Cys Pro His Asn Ser Ser Asn Asn Ala Asn Val
                325                 330                 335
Thr Trp Trp Arg Val Leu His Gly Asn Tyr Thr Trp Pro Pro Glu Phe
            340                 345                 350
Leu Gly Pro Gly Glu Asp Pro Asn Gly Thr Leu Ile Ile Gln Asn Val
        355                 360                 365
Asn Lys Ser His Gly Gly Ile Tyr Val Cys Arg Val Gln Glu Gly Asn
    370                 375                 380
Glu Ser Tyr Gln Gln Ser Cys Gly Thr Tyr Leu Arg Val Arg Gln Pro
385                 390                 395                 400
Pro Pro Arg Pro Phe Leu Asp Met Gly Glu Gly Thr Lys Asn Arg Ile
                405                 410                 415
Ile Thr Ala Glu Gly Ile Ile Leu Leu Phe Cys Ala Val Val Pro Gly
            420                 425                 430
Thr Leu Leu Leu Phe Arg Lys Arg Trp Gln Asn Glu Lys Leu Gly Leu
        435                 440                 445
Asp Ala Gly Asp Glu Tyr Glu Asp Glu Asn Leu Tyr Glu Gly Leu Asn
    450                 455                 460
Leu Asp Asp Cys Ser Met Tyr Glu Asp Ile Ser Arg Gly Leu Gln Gly
465                 470                 475                 480
Thr Tyr Gln Asp Val Gly Ser Leu Asn Ile Gly Asp Val Gln Leu Glu
                485                 490                 495
Lys Pro Arg Lys Arg Arg Ala Ser Glu Gly Arg Gly Ser Leu Leu Thr
            500                 505                 510
Cys Gly Asp Val Glu Glu Asn Pro Gly Pro Met Ala Arg Leu Ala Leu
        515                 520                 525
Ser Pro Val Pro Ser His Trp Met Val Ala Leu Leu Leu Leu Leu Ser
    530                 535                 540
Ala Ala Glu Pro Val Pro Ala Ala Arg Ser Glu Asp Arg Tyr Arg Asn
545                 550                 555                 560
Pro Lys Gly Ser Ala Cys Ser Arg Ile Trp Gln Ser Pro Arg Phe Ile
                565                 570                 575
```

```
Ala Arg Lys Arg Gly Phe Thr Val Lys Met His Cys Tyr Met Asn Ser
            580                 585                 590

Ala Ser Gly Asn Val Ser Trp Leu Trp Lys Gln Glu Met Asp Glu Asn
            595                 600                 605

Pro Gln Gln Leu Lys Leu Glu Lys Gly Arg Met Glu Glu Ser Gln Asn
            610                 615                 620

Glu Ser Leu Ala Thr Leu Thr Ile Gln Gly Ile Arg Phe Glu Asp Asn
625                 630                 635                 640

Gly Ile Tyr Phe Cys Gln Gln Lys Cys Asn Asn Thr Ser Glu Val Tyr
            645                 650                 655

Gln Gly Cys Gly Thr Glu Leu Arg Val Met Gly Phe Ser Thr Leu Ala
            660                 665                 670

Gln Leu Lys Gln Arg Asn Thr Leu Lys Asp Gly Ile Ile Met Ile Gln
            675                 680                 685

Thr Leu Leu Ile Ile Leu Phe Ile Ile Val Pro Ile Phe Leu Leu Leu
            690                 695                 700

Asp Lys Asp Asp Ser Lys Ala Gly Met Glu Glu Asp His Thr Tyr Glu
705                 710                 715                 720

Gly Leu Asp Ile Asp Gln Thr Ala Thr Tyr Glu Asp Ile Val Thr Leu
            725                 730                 735

Arg Thr Gly Glu Val Lys Trp Ser Val Gly Glu His Pro Gly Gln Glu
            740                 745                 750

<210> SEQ ID NO 11
<211> LENGTH: 1335
<212> TYPE: DNA
<213> ORGANISM: Artificial Sequence
<220> FEATURE:
<223> OTHER INFORMATION: Chimeric Protein:  FcgammaR1-CD3Z
<220> FEATURE:
<221> NAME/KEY: CDS
<222> LOCATION: (1)..(1335)

<400> SEQUENCE: 11 atg aag tgg aag gcg ctt ttc acc gcg gcc atc ctg cag gca cag ttg      48
Met Lys Trp Lys Ala Leu Phe Thr Ala Ala Ile Leu Gln Ala Gln Leu
1               5                  10                  15 ccg att aca gag gca gaa gtg gtt aat gcc acc aag gct gtg atc acc      96
Pro Ile Thr Glu Ala Glu Val Val Asn Ala Thr Lys Ala Val Ile Thr
            20                  25                  30 ttg cag cct cca tgg gtc agt att ttc cag aag gaa aat gtc act tta     144
Leu Gln Pro Pro Trp Val Ser Ile Phe Gln Lys Glu Asn Val Thr Leu
        35                  40                  45 tgg tgt gag ggg cct cac ctg cct gga gac agt tcc aca caa tgg ttt     192
Trp Cys Glu Gly Pro His Leu Pro Gly Asp Ser Ser Thr Gln Trp Phe
    50                  55                  60 atc aac gga aca gcc gtt cag atc tcc acg cct agt tat agc atc cca     240
Ile Asn Gly Thr Ala Val Gln Ile Ser Thr Pro Ser Tyr Ser Ile Pro
65                  70                  75                  80 gag gcc agt ttt cag gac agt ggc gaa tac agg tgt cag ata ggt tcc     288
Glu Ala Ser Phe Gln Asp Ser Gly Glu Tyr Arg Cys Gln Ile Gly Ser
            85                  90                  95 tca atg cca agt gac cct gtg cag ttg caa atc cac aat gat tgg ctg     336
Ser Met Pro Ser Asp Pro Val Gln Leu Gln Ile His Asn Asp Trp Leu
            100                 105                 110 cta ctc cag gcc tcc cgc aga gtc ctc aca gaa gga gaa ccc ctg gcc     384
Leu Leu Gln Ala Ser Arg Arg Val Leu Thr Glu Gly Glu Pro Leu Ala
        115                 120                 125 ttg agg tgt cac gga tgg aag aat aaa ctg gtg tac aat gtg gtt ttc     432
```

```
                Leu Arg Cys His Gly Trp Lys Asn Lys Leu Val Tyr Asn Val Val Phe
                    130                 135                 140 tat aga aat gga aaa tcc ttt cag ttt tct tca gat tcg gag gtc gcc        480
Tyr Arg Asn Gly Lys Ser Phe Gln Phe Ser Ser Asp Ser Glu Val Ala
145                 150                 155                 160 att ctg aaa acc aac ctg agt cac agc ggc atc tac cac tgc tca ggc        528
Ile Leu Lys Thr Asn Leu Ser His Ser Gly Ile Tyr His Cys Ser Gly
                    165                 170                 175 acg gga aga cac cgc tac aca tct gca gga gtg tcc atc acg gtg aaa        576
Thr Gly Arg His Arg Tyr Thr Ser Ala Gly Val Ser Ile Thr Val Lys
                180                 185                 190 gag ctg ttt acc acg cca gtg ctg aga gca tcc gtg tca tct ccc ttc        624
Glu Leu Phe Thr Thr Pro Val Leu Arg Ala Ser Val Ser Ser Pro Phe
            195                 200                 205 ccg gag ggg agt ctg gtc acc ctg aac tgt gag acg aat ttg ctc ctg        672
Pro Glu Gly Ser Leu Val Thr Leu Asn Cys Glu Thr Asn Leu Leu Leu
        210                 215                 220 cag aga ccc ggc tta cag ctt cac ttc tcc ttc tac gtg ggc agc aag        720
Gln Arg Pro Gly Leu Gln Leu His Phe Ser Phe Tyr Val Gly Ser Lys
225                 230                 235                 240 atc ctg gag tac agg aac aca tcc tca gag tac cat ata gca agg gcg        768
Ile Leu Glu Tyr Arg Asn Thr Ser Ser Glu Tyr His Ile Ala Arg Ala
                    245                 250                 255 gaa aga gaa gat gct gga ttc tac tgg tgt gag gta gcc acg gag gac        816
Glu Arg Glu Asp Ala Gly Phe Tyr Trp Cys Glu Val Ala Thr Glu Asp
                260                 265                 270 agc agt gtc ctt aag cgc agc cct gag ttg gag ctc caa gtg ctt ggt        864
Ser Ser Val Leu Lys Arg Ser Pro Glu Leu Glu Leu Gln Val Leu Gly
            275                 280                 285 ccc cag tca tca gct cct ggt tct gct tct ggt tct ggt cag agc ttt        912
Pro Gln Ser Ser Ala Pro Gly Ser Ala Ser Gly Ser Gly Gln Ser Phe
        290                 295                 300 ggc ctg ctg gat ccc aaa ctc tgc tac ctg ctg gat gga atc ctc ttc        960
Gly Leu Leu Asp Pro Lys Leu Cys Tyr Leu Leu Asp Gly Ile Leu Phe
305                 310                 315                 320 atc tat ggt gtc att ctc act gcc ttg ttc ctg aga gtg aag ttc agc       1008
Ile Tyr Gly Val Ile Leu Thr Ala Leu Phe Leu Arg Val Lys Phe Ser
                    325                 330                 335 agg agc gca gac gcc ccc gcg tac cag cag ggc cag aac cag ctc tat       1056
Arg Ser Ala Asp Ala Pro Ala Tyr Gln Gln Gly Gln Asn Gln Leu Tyr
                340                 345                 350 aac gag ctc aat cta gga cga aga gag gag tac gat gtt ttg gac aag       1104
Asn Glu Leu Asn Leu Gly Arg Arg Glu Glu Tyr Asp Val Leu Asp Lys
            355                 360                 365 aga cgt ggc cgg gac cct gag atg ggg gga aag ccg cag aga agg aag       1152
Arg Arg Gly Arg Asp Pro Glu Met Gly Gly Lys Pro Gln Arg Arg Lys
        370                 375                 380 aac cct cag gaa ggc ctg tac aat gaa ctg cag aaa gat aag atg gcg       1200
Asn Pro Gln Glu Gly Leu Tyr Asn Glu Leu Gln Lys Asp Lys Met Ala
385                 390                 395                 400 gag gcc tac agt gag att ggg atg aaa ggc gag cgc cgg agg ggc aag       1248
Glu Ala Tyr Ser Glu Ile Gly Met Lys Gly Glu Arg Arg Arg Gly Lys
                    405                 410                 415 ggg cac gat ggc ctt tac cag ggt ctc agt aca gcc acc aag gac acc       1296
Gly His Asp Gly Leu Tyr Gln Gly Leu Ser Thr Ala Thr Lys Asp Thr
                420                 425                 430 tac gac gcc ctt cac atg cag gcc ctg ccc cct cgc taa                   1335
Tyr Asp Ala Leu His Met Gln Ala Leu Pro Pro Arg
            435                 440
```

<210> SEQ ID NO 12
<211> LENGTH: 444
<212> TYPE: PRT
<213> ORGANISM: Artificial Sequence
<220> FEATURE:
<223> OTHER INFORMATION: Synthetic Construct

<400> SEQUENCE: 12

```
Met Lys Trp Lys Ala Leu Phe Thr Ala Ala Ile Leu Gln Ala Gln Leu
1               5                   10                  15

Pro Ile Thr Glu Ala Glu Val Val Asn Ala Thr Lys Ala Val Ile Thr
            20                  25                  30

Leu Gln Pro Pro Trp Val Ser Ile Phe Gln Lys Glu Asn Val Thr Leu
        35                  40                  45

Trp Cys Glu Gly Pro His Leu Pro Gly Asp Ser Ser Thr Gln Trp Phe
50                  55                  60

Ile Asn Gly Thr Ala Val Gln Ile Ser Thr Pro Ser Tyr Ser Ile Pro
65                  70                  75                  80

Glu Ala Ser Phe Gln Asp Ser Gly Glu Tyr Arg Cys Gln Ile Gly Ser
                85                  90                  95

Ser Met Pro Ser Asp Pro Val Gln Leu Gln Ile His Asn Asp Trp Leu
            100                 105                 110

Leu Leu Gln Ala Ser Arg Arg Val Leu Thr Glu Gly Glu Pro Leu Ala
        115                 120                 125

Leu Arg Cys His Gly Trp Lys Asn Lys Leu Val Tyr Asn Val Val Phe
130                 135                 140

Tyr Arg Asn Gly Lys Ser Phe Gln Phe Ser Ser Asp Ser Glu Val Ala
145                 150                 155                 160

Ile Leu Lys Thr Asn Leu Ser His Ser Gly Ile Tyr His Cys Ser Gly
                165                 170                 175

Thr Gly Arg His Arg Tyr Thr Ser Ala Gly Val Ser Ile Thr Val Lys
            180                 185                 190

Glu Leu Phe Thr Thr Pro Val Leu Arg Ala Ser Val Ser Ser Pro Phe
        195                 200                 205

Pro Glu Gly Ser Leu Val Thr Leu Asn Cys Glu Thr Asn Leu Leu Leu
210                 215                 220

Gln Arg Pro Gly Leu Gln Leu His Phe Ser Phe Tyr Val Gly Ser Lys
225                 230                 235                 240

Ile Leu Glu Tyr Arg Asn Thr Ser Ser Glu Tyr His Ile Ala Arg Ala
                245                 250                 255

Glu Arg Glu Asp Ala Gly Phe Tyr Trp Cys Glu Val Ala Thr Glu Asp
            260                 265                 270

Ser Ser Val Leu Lys Arg Ser Pro Glu Leu Glu Leu Gln Val Leu Gly
        275                 280                 285

Pro Gln Ser Ser Ala Pro Gly Ser Ala Ser Gly Ser Gly Gln Ser Phe
290                 295                 300

Gly Leu Leu Asp Pro Lys Leu Cys Tyr Leu Leu Asp Gly Ile Leu Phe
305                 310                 315                 320

Ile Tyr Gly Val Ile Leu Thr Ala Leu Phe Leu Arg Val Lys Phe Ser
                325                 330                 335

Arg Ser Ala Asp Ala Pro Ala Tyr Gln Gln Gly Gln Asn Gln Leu Tyr
            340                 345                 350

Asn Glu Leu Asn Leu Gly Arg Arg Glu Glu Tyr Asp Val Leu Asp Lys
        355                 360                 365
```

```
Arg Arg Gly Arg Asp Pro Glu Met Gly Gly Lys Pro Gln Arg Arg Lys
370             375                 380

Asn Pro Gln Glu Gly Leu Tyr Asn Glu Leu Gln Lys Asp Lys Met Ala
385             390                 395                 400

Glu Ala Tyr Ser Glu Ile Gly Met Lys Gly Glu Arg Arg Arg Gly Lys
                405                 410                 415

Gly His Asp Gly Leu Tyr Gln Gly Leu Ser Thr Ala Thr Lys Asp Thr
                420                 425                 430

Tyr Asp Ala Leu His Met Gln Ala Leu Pro Pro Arg
            435                 440
```

<210> SEQ ID NO 13
<211> LENGTH: 1848
<212> TYPE: DNA
<213> ORGANISM: Artificial Sequence
<220> FEATURE:
<223> OTHER INFORMATION: Chimeric Protein: FcgammaR1-IgE
<220> FEATURE:
<221> NAME/KEY: CDS
<222> LOCATION: (1)..(1848)

<400> SEQUENCE: 13

```
cat atg gaa gtg gtt aat gcc acc aag gct gtg atc acc ttg cag cct      48
His Met Glu Val Val Asn Ala Thr Lys Ala Val Ile Thr Leu Gln Pro
1               5                   10                  15 cca tgg gtc agt att ttc cag aag gaa aat gtc act tta tgg tgt gag      96
Pro Trp Val Ser Ile Phe Gln Lys Glu Asn Val Thr Leu Trp Cys Glu
                20                  25                  30 ggg cct cac ctg cct gga gac agt tcc aca caa tgg ttt atc aac gga     144
Gly Pro His Leu Pro Gly Asp Ser Ser Thr Gln Trp Phe Ile Asn Gly
            35                  40                  45 aca gcc gtt cag atc tcc acg cct agt tat agc atc cca gag gcc agt     192
Thr Ala Val Gln Ile Ser Thr Pro Ser Tyr Ser Ile Pro Glu Ala Ser
        50                  55                  60 ttt cag gac agt ggc gaa tac agg tgt cag ata ggt ccc tca atg cca     240
Phe Gln Asp Ser Gly Glu Tyr Arg Cys Gln Ile Gly Ser Ser Met Pro
65                  70                  75                  80 agt gac cct gtg cag ttg caa atc cac aat gat tgg ctg cta ctc cag     288
Ser Asp Pro Val Gln Leu Gln Ile His Asn Asp Trp Leu Leu Leu Gln
                85                  90                  95 gcc tcc cgc aga gtc ctc aca gaa gga gaa ccc ctg gcc ttg agg tgt     336
Ala Ser Arg Arg Val Leu Thr Glu Gly Glu Pro Leu Ala Leu Arg Cys
                100                 105                 110 cac gga tgg aag aat aaa ctg gtg tac aat gtg gtt ttc tat aga aat     384
His Gly Trp Lys Asn Lys Leu Val Tyr Asn Val Val Phe Tyr Arg Asn
            115                 120                 125 gga aaa tcc ttt cag ttt tct tca gat tcg gag gtc gcc att ctg aaa     432
Gly Lys Ser Phe Gln Phe Ser Ser Asp Ser Glu Val Ala Ile Leu Lys
        130                 135                 140 acc aac ctg agt cac agc ggc atc tac cac tgc tca ggc acg gga aga     480
Thr Asn Leu Ser His Ser Gly Ile Tyr His Cys Ser Gly Thr Gly Arg
145                 150                 155                 160 cac cgc tac aca tct gca gga gtg tcc atc acg gtg aaa gag ctg ttt     528
His Arg Tyr Thr Ser Ala Gly Val Ser Ile Thr Val Lys Glu Leu Phe
                165                 170                 175 acc acg cca gtg ctg aga gca tcc gtg tca tct ccc ttc ccg gag ggg     576
Thr Thr Pro Val Leu Arg Ala Ser Val Ser Ser Pro Phe Pro Glu Gly
                180                 185                 190 agt ctg gtc acc ctg aac tgt gag acg aat ttg ctc ctg cag aga ccc     624
Ser Leu Val Thr Leu Asn Cys Glu Thr Asn Leu Leu Leu Gln Arg Pro
            195                 200                 205
```

-continued

| | |
|---|---|
| ggc tta cag ctt cac ttc tcc ttc tac gtg ggc agc aag atc ctg gag<br>Gly Leu Gln Leu His Phe Ser Phe Tyr Val Gly Ser Lys Ile Leu Glu<br>210                              215                       220 | 672 |
| tac agg aac aca tcc tca gag tac cat ata gca agg gcg gaa aga gaa<br>Tyr Arg Asn Thr Ser Ser Glu Tyr His Ile Ala Arg Ala Glu Arg Glu<br>225                       230                     235                   240 | 720 |
| gat gct gga ttc tac tgg tgt gag gta gcc acg gag gac agc agt gtc<br>Asp Ala Gly Phe Tyr Trp Cys Glu Val Ala Thr Glu Asp Ser Ser Val<br>                       245                     250                   255 | 768 |
| ctt aag cgc agc cct gag ttg gag ctc caa gtg ctt ggt ccc cag tca<br>Leu Lys Arg Ser Pro Glu Leu Glu Leu Gln Val Leu Gly Pro Gln Ser<br>               260                     265                   270 | 816 |
| tca gct cct ggt tct gct tct ggt tct ggt gtt cga cca gtt aac atc<br>Ser Ala Pro Gly Ser Ala Ser Gly Ser Gly Val Arg Pro Val Asn Ile<br>275                       280                     285 | 864 |
| acc gag ccc aca ctg gaa ctg ctg cac agc agc tgc gac ccc aac gcc<br>Thr Glu Pro Thr Leu Glu Leu Leu His Ser Ser Cys Asp Pro Asn Ala<br>                       290                     295                   300 | 912 |
| ttc cac agc acc atc cag ctg tat tgc ttc atc tac ggc cac atc ctg<br>Phe His Ser Thr Ile Gln Leu Tyr Cys Phe Ile Tyr Gly His Ile Leu<br>305                              310                     315                   320 | 960 |
| aac gac gtg tcc gtg tcc tgg ctg atg gac gac aga gag atc acc gac<br>Asn Asp Val Ser Val Ser Trp Leu Met Asp Asp Arg Glu Ile Thr Asp<br>                       325                     330                   335 | 1008 |
| acc ctg gcc cag acc gtg ctg atc aaa gag gaa ggc aag ctg gcc tct<br>Thr Leu Ala Gln Thr Val Leu Ile Lys Glu Glu Gly Lys Leu Ala Ser<br>                       340                     345                   350 | 1056 |
| acc tgc agc aag ctg aat atc aca gag cag cag tgg atg agc gag agc<br>Thr Cys Ser Lys Leu Asn Ile Thr Glu Gln Gln Trp Met Ser Glu Ser<br>                   355                     360                   365 | 1104 |
| acc ttc acc tgt aaa gtg acc tcc cag ggc gtg gac tac ctg gcc cac<br>Thr Phe Thr Cys Lys Val Thr Ser Gln Gly Val Asp Tyr Leu Ala His<br>370                              375                     380 | 1152 |
| acc aga aga tgc ccc gac cac gaa ccc aga ggc gtg atc acc tac ctg<br>Thr Arg Arg Cys Pro Asp His Glu Pro Arg Gly Val Ile Thr Tyr Leu<br>385                              390                     395                   400 | 1200 |
| atc ccc cct agc ccc ctg gac ctg tac cag aac ggc gct cct aag ctg<br>Ile Pro Pro Ser Pro Leu Asp Leu Tyr Gln Asn Gly Ala Pro Lys Leu<br>                       405                     410                   415 | 1248 |
| acc tgc ctg gtg gtg gac ctg gaa agc gag aag aac gtg aac gtg aca<br>Thr Cys Leu Val Val Asp Leu Glu Ser Glu Lys Asn Val Asn Val Thr<br>                       420                     425                   430 | 1296 |
| tgg aac cag gaa aag aaa acc agc gtg tcc gcc agc cag tgg tac acc<br>Trp Asn Gln Glu Lys Lys Thr Ser Val Ser Ala Ser Gln Trp Tyr Thr<br>                   435                     440                   445 | 1344 |
| aag cac cac aac aac gcc acc acc tcc atc acc agc atc ctg ccc gtg<br>Lys His His Asn Asn Ala Thr Thr Ser Ile Thr Ser Ile Leu Pro Val<br>                       450                     455                   460 | 1392 |
| gtg gcc aag gac tgg atc gag ggc tac ggc tac cag tgc atc gtg gac<br>Val Ala Lys Asp Trp Ile Glu Gly Tyr Gly Tyr Gln Cys Ile Val Asp<br>465                              470                     475                   480 | 1440 |
| cac ccc gac ttc cct aag ccc atc gtg cgg agc atc acc aag acc cct<br>His Pro Asp Phe Pro Lys Pro Ile Val Arg Ser Ile Thr Lys Thr Pro<br>                       485                     490                   495 | 1488 |
| ggc cag aga tct gcc ccc gag gtg tac gtg ttc ccc cca cct gag gaa<br>Gly Gln Arg Ser Ala Pro Glu Val Tyr Val Phe Pro Pro Pro Glu Glu<br>                       500                     505                   510 | 1536 |
| gag tcc gag gac aag aga acc ctg acc tgt ctg atc cag aac ttc ttc<br>Glu Ser Glu Asp Lys Arg Thr Leu Thr Cys Leu Ile Gln Asn Phe Phe | 1584 |

```
                515                 520                 525
cca gag gac atc agc gtg cag tgg ctg ggc gac ggc aag ctg atc tcc    1632
Pro Glu Asp Ile Ser Val Gln Trp Leu Gly Asp Gly Lys Leu Ile Ser
    530                 535                 540 aac agc cag cac agc aca acc acc cct ctg aag tcc aac ggc agc aac    1680
Asn Ser Gln His Ser Thr Thr Thr Pro Leu Lys Ser Asn Gly Ser Asn
545                 550                 555                 560 cag ggc ttc ttc atc ttc agc aga ctg gaa gtg gcc aag acc ctg tgg    1728
Gln Gly Phe Phe Ile Phe Ser Arg Leu Glu Val Ala Lys Thr Leu Trp
                565                 570                 575 acc cag aga aag cag ttt aca tgc caa gtg atc cat gag gcc ctg cag    1776
Thr Gln Arg Lys Gln Phe Thr Cys Gln Val Ile His Glu Ala Leu Gln
            580                 585                 590 aag ccc aga aag ctg gaa aag acc atc agc acc agc ctg ggc aac acc    1824
Lys Pro Arg Lys Leu Glu Lys Thr Ile Ser Thr Ser Leu Gly Asn Thr
        595                 600                 605 tcc ctg cgc cct agt tag ctc gag                                    1848
Ser Leu Arg Pro Ser Leu Glu
    610             615
```

<210> SEQ ID NO 14
<211> LENGTH: 613
<212> TYPE: PRT
<213> ORGANISM: Artificial Sequence
<220> FEATURE:
<223> OTHER INFORMATION: Synthetic Construct

<400> SEQUENCE: 14

```
His Met Glu Val Val Asn Ala Thr Lys Ala Val Ile Thr Leu Gln Pro
1               5                   10                  15

Pro Trp Val Ser Ile Phe Gln Lys Glu Asn Val Thr Leu Trp Cys Glu
            20                  25                  30

Gly Pro His Leu Pro Gly Asp Ser Ser Thr Gln Trp Phe Ile Asn Gly
        35                  40                  45

Thr Ala Val Gln Ile Ser Thr Pro Ser Tyr Ser Ile Pro Glu Ala Ser
    50                  55                  60

Phe Gln Asp Ser Gly Glu Tyr Arg Cys Gln Ile Gly Ser Ser Met Pro
65                  70                  75                  80

Ser Asp Pro Val Gln Leu Gln Ile His Asn Asp Trp Leu Leu Leu Gln
                85                  90                  95

Ala Ser Arg Arg Val Leu Thr Glu Gly Glu Pro Leu Ala Leu Arg Cys
            100                 105                 110

His Gly Trp Lys Asn Lys Leu Val Tyr Asn Val Phe Tyr Arg Asn
        115                 120                 125

Gly Lys Ser Phe Gln Phe Ser Ser Asp Ser Glu Val Ala Ile Leu Lys
    130                 135                 140

Thr Asn Leu Ser His Ser Gly Ile Tyr His Cys Ser Gly Thr Gly Arg
145                 150                 155                 160

His Arg Tyr Thr Ser Ala Gly Val Ser Ile Thr Val Lys Glu Leu Phe
                165                 170                 175

Thr Thr Pro Val Leu Arg Ala Ser Val Ser Ser Pro Phe Pro Glu Gly
            180                 185                 190

Ser Leu Val Thr Leu Asn Cys Glu Thr Asn Leu Leu Leu Gln Arg Pro
        195                 200                 205

Gly Leu Gln Leu His Phe Ser Phe Tyr Val Gly Ser Lys Ile Leu Glu
    210                 215                 220

Tyr Arg Asn Thr Ser Ser Glu Tyr His Ile Ala Arg Ala Glu Arg Glu
```

```
            225                 230                 235                 240
Asp Ala Gly Phe Tyr Trp Cys Glu Val Ala Thr Glu Asp Ser Ser Val
                245                 250                 255

Leu Lys Arg Ser Pro Glu Leu Glu Leu Gln Val Leu Gly Pro Gln Ser
                260                 265                 270

Ser Ala Pro Gly Ser Ala Ser Gly Ser Gly Val Arg Pro Val Asn Ile
                275                 280                 285

Thr Glu Pro Thr Leu Glu Leu Leu His Ser Ser Cys Asp Pro Asn Ala
                290                 295                 300

Phe His Ser Thr Ile Gln Leu Tyr Cys Phe Ile Tyr Gly His Ile Leu
305                 310                 315                 320

Asn Asp Val Ser Val Ser Trp Leu Met Asp Asp Arg Glu Ile Thr Asp
                325                 330                 335

Thr Leu Ala Gln Thr Val Leu Ile Lys Glu Glu Gly Lys Leu Ala Ser
                340                 345                 350

Thr Cys Ser Lys Leu Asn Ile Thr Glu Gln Gln Trp Met Ser Glu Ser
                355                 360                 365

Thr Phe Thr Cys Lys Val Thr Ser Gln Gly Val Asp Tyr Leu Ala His
                370                 375                 380

Thr Arg Arg Cys Pro Asp His Glu Pro Arg Gly Val Ile Thr Tyr Leu
385                 390                 395                 400

Ile Pro Pro Ser Pro Leu Asp Leu Tyr Gln Asn Gly Ala Pro Lys Leu
                405                 410                 415

Thr Cys Leu Val Val Asp Leu Glu Ser Glu Lys Asn Val Asn Val Thr
                420                 425                 430

Trp Asn Gln Glu Lys Lys Thr Ser Val Ser Ala Ser Gln Trp Tyr Thr
                435                 440                 445

Lys His His Asn Asn Ala Thr Thr Ser Ile Thr Ser Ile Leu Pro Val
                450                 455                 460

Val Ala Lys Asp Trp Ile Glu Gly Tyr Gly Tyr Gln Cys Ile Val Asp
465                 470                 475                 480

His Pro Asp Phe Pro Lys Pro Ile Val Arg Ser Ile Thr Lys Thr Pro
                485                 490                 495

Gly Gln Arg Ser Ala Pro Glu Val Tyr Val Phe Pro Pro Glu Glu
                500                 505                 510

Glu Ser Glu Asp Lys Arg Thr Leu Thr Cys Leu Ile Gln Asn Phe Phe
                515                 520                 525

Pro Glu Asp Ile Ser Val Gln Trp Leu Gly Asp Gly Lys Leu Ile Ser
                530                 535                 540

Asn Ser Gln His Ser Thr Thr Pro Leu Lys Ser Asn Gly Ser Asn
545                 550                 555                 560

Gln Gly Phe Phe Ile Phe Ser Arg Leu Glu Val Ala Lys Thr Leu Trp
                565                 570                 575

Thr Gln Arg Lys Gln Phe Thr Cys Gln Val Ile His Glu Ala Leu Gln
                580                 585                 590

Lys Pro Arg Lys Leu Glu Lys Thr Ile Ser Thr Ser Leu Gly Asn Thr
                595                 600                 605

Ser Leu Arg Pro Ser
        610

<210> SEQ ID NO 15
<211> LENGTH: 1449
<212> TYPE: DNA
<213> ORGANISM: Artificial Sequence
```

```
<220> FEATURE:
<223> OTHER INFORMATION: Chimeric Protein: BBP-IgE
<220> FEATURE:
<221> NAME/KEY: CDS
<222> LOCATION: (1)..(1449)

<400> SEQUENCE: 15 cat atg act tac aag ctg gtg atc aac ggt aaa acc ttg aag ggt gag      48
His Met Thr Tyr Lys Leu Val Ile Asn Gly Lys Thr Leu Lys Gly Glu
1               5                   10                  15 acc acc act gag gca gtc gac gcc gcc act gcc gag aag gtc ttt aaa      96
Thr Thr Thr Glu Ala Val Asp Ala Ala Thr Ala Glu Lys Val Phe Lys
                20                  25                  30 cag tat gcc aat gat aac ggc gtg gac ggc gag tgg acc tac gat gac     144
Gln Tyr Ala Asn Asp Asn Gly Val Asp Gly Glu Trp Thr Tyr Asp Asp
            35                  40                  45 gcc act aag aca ttc act gtg act gaa aag ccc gag gtg att gac gcg     192
Ala Thr Lys Thr Phe Thr Val Thr Glu Lys Pro Glu Val Ile Asp Ala
        50                  55                  60 tcc gaa ttg aca cct gcg gtg acc acc tac aaa ctg gtt atc aac ggc     240
Ser Glu Leu Thr Pro Ala Val Thr Thr Tyr Lys Leu Val Ile Asn Gly
65                  70                  75                  80 aag act ctg aag ggc gag acc acc aca gag gca gtc gat gcc gcc acc     288
Lys Thr Leu Lys Gly Glu Thr Thr Thr Glu Ala Val Asp Ala Ala Thr
                85                  90                  95 gcc gag aag gtc ttc aag caa tat gcc aac gac aac ggg gtg gac ggg     336
Ala Glu Lys Val Phe Lys Gln Tyr Ala Asn Asp Asn Gly Val Asp Gly
                100                 105                 110 gag tgg acc tac gat gat gcc acc aag acc ttc acc gtg acc gag aag     384
Glu Trp Thr Tyr Asp Asp Ala Thr Lys Thr Phe Thr Val Thr Glu Lys
            115                 120                 125 ccc gaa gtg atc gat gcg agt gaa ctg act ccc gcc gtg aca ggt tct     432
Pro Glu Val Ile Asp Ala Ser Glu Leu Thr Pro Ala Val Thr Gly Ser
        130                 135                 140 gct tct ggt tct ggt gtt cga cca gtt aac atc acc gag ccc aca ctg     480
Ala Ser Gly Ser Gly Val Arg Pro Val Asn Ile Thr Glu Pro Thr Leu
145                 150                 155                 160 gaa ctg ctg cac agc agc tgc gac ccc aac gcc ttc cac agc acc atc     528
Glu Leu Leu His Ser Ser Cys Asp Pro Asn Ala Phe His Ser Thr Ile
                165                 170                 175 cag ctg tat tgc ttc atc tac ggc cac atc ctg aac gac gtg tcc gtg     576
Gln Leu Tyr Cys Phe Ile Tyr Gly His Ile Leu Asn Asp Val Ser Val
            180                 185                 190 tcc tgg ctg atg gac gac aga gag atc acc gac acc ctg gcc cag acc     624
Ser Trp Leu Met Asp Asp Arg Glu Ile Thr Asp Thr Leu Ala Gln Thr
        195                 200                 205 gtg ctg atc aaa gag gaa ggc aag ctg gcc tct acc tgc agc aag ctg     672
Val Leu Ile Lys Glu Glu Gly Lys Leu Ala Ser Thr Cys Ser Lys Leu
    210                 215                 220 aat atc aca gag cag cag tgg atg agc gag agc acc ttc acc tgt aaa     720
Asn Ile Thr Glu Gln Gln Trp Met Ser Glu Ser Thr Phe Thr Cys Lys
225                 230                 235                 240 gtg acc tcc cag ggc gtg gac tac ctg gcc cac acc aga aga tgc ccc     768
Val Thr Ser Gln Gly Val Asp Tyr Leu Ala His Thr Arg Arg Cys Pro
                245                 250                 255 gac cac gaa ccc aga ggc gtg atc acc tac ctg atc ccc cct agc ccc     816
Asp His Glu Pro Arg Gly Val Ile Thr Tyr Leu Ile Pro Pro Ser Pro
            260                 265                 270 ctg gac ctg tac cag aac ggc gct cct aag ctg acc tgc ctg gtg gtg     864
Leu Asp Leu Tyr Gln Asn Gly Ala Pro Lys Leu Thr Cys Leu Val Val
        275                 280                 285
```

```
gac ctg gaa agc gag aag aac gtg aac gtg aca tgg aac cag gaa aag      912
Asp Leu Glu Ser Glu Lys Asn Val Asn Val Thr Trp Asn Gln Glu Lys
        290                 295                 300 aaa acc agc gtg tcc gcc agc cag tgg tac acc aag cac cac aac aac      960
Lys Thr Ser Val Ser Ala Ser Gln Trp Tyr Thr Lys His His Asn Asn
305                 310                 315                 320 gcc acc acc tcc atc acc agc atc ctg ccc gtg gtg gcc aag gac tgg     1008
Ala Thr Thr Ser Ile Thr Ser Ile Leu Pro Val Val Ala Lys Asp Trp
                325                 330                 335 atc gag ggc tac ggc tac cag tgc atc gtg gac cac ccc gac ttc cct     1056
Ile Glu Gly Tyr Gly Tyr Gln Cys Ile Val Asp His Pro Asp Phe Pro
            340                 345                 350 aag ccc atc gtg cgg agc atc acc aag acc cct ggc cag aga tct gcc     1104
Lys Pro Ile Val Arg Ser Ile Thr Lys Thr Pro Gly Gln Arg Ser Ala
        355                 360                 365 ccc gag gtg tac gtg ttc ccc cca cct gag gaa gag tcc gag gac aag     1152
Pro Glu Val Tyr Val Phe Pro Pro Pro Glu Glu Glu Ser Glu Asp Lys
    370                 375                 380 aga acc ctg acc tgt ctg atc cag aac ttc ttc cca gag gac atc agc     1200
Arg Thr Leu Thr Cys Leu Ile Gln Asn Phe Phe Pro Glu Asp Ile Ser
385                 390                 395                 400 gtg cag tgg ctg ggc gac ggc aag ctg atc tcc aac agc cag cac agc     1248
Val Gln Trp Leu Gly Asp Gly Lys Leu Ile Ser Asn Ser Gln His Ser
                405                 410                 415 aca acc acc cct ctg aag tcc aac ggc agc aac cag ggc ttc ttc atc     1296
Thr Thr Thr Pro Leu Lys Ser Asn Gly Ser Asn Gln Gly Phe Phe Ile
            420                 425                 430 ttc agc aga ctg gaa gtg gcc aag acc ctg tgg acc cag aga aag cag     1344
Phe Ser Arg Leu Glu Val Ala Lys Thr Leu Trp Thr Gln Arg Lys Gln
        435                 440                 445 ttt aca tgc caa gtg atc cat gag gcc ctg cag aag ccc aga aag ctg     1392
Phe Thr Cys Gln Val Ile His Glu Ala Leu Gln Lys Pro Arg Lys Leu
    450                 455                 460 gaa aag acc atc agc acc agc ctg ggc aac acc tcc ctg cgc cct agt     1440
Glu Lys Thr Ile Ser Thr Ser Leu Gly Asn Thr Ser Leu Arg Pro Ser
465                 470                 475                 480 tag ctc gag                                                         1449
Leu Glu <210> SEQ ID NO 16
<211> LENGTH: 480
<212> TYPE: PRT
<213> ORGANISM: Artificial Sequence
<220> FEATURE:
<223> OTHER INFORMATION: Synthetic Construct

<400> SEQUENCE: 16

His Met Thr Tyr Lys Leu Val Ile Asn Gly Lys Thr Leu Lys Gly Glu
1               5                   10                  15

Thr Thr Thr Glu Ala Val Asp Ala Ala Thr Ala Glu Lys Val Phe Lys
            20                  25                  30

Gln Tyr Ala Asn Asp Asn Gly Val Asp Gly Glu Trp Thr Tyr Asp Asp
        35                  40                  45

Ala Thr Lys Thr Phe Thr Val Thr Glu Lys Pro Glu Val Ile Asp Ala
    50                  55                  60

Ser Glu Leu Thr Pro Ala Val Thr Thr Tyr Lys Leu Val Ile Asn Gly
65                  70                  75                  80

Lys Thr Leu Lys Gly Glu Thr Thr Thr Glu Ala Val Asp Ala Ala Thr
                85                  90                  95
```

Ala Glu Lys Val Phe Lys Gln Tyr Ala Asn Asp Asn Gly Val Asp Gly
            100                 105                 110

Glu Trp Thr Tyr Asp Asp Ala Thr Lys Thr Phe Thr Val Thr Glu Lys
            115                 120                 125

Pro Glu Val Ile Asp Ala Ser Glu Leu Thr Pro Ala Val Thr Gly Ser
            130                 135                 140

Ala Ser Gly Ser Gly Val Arg Pro Val Asn Ile Thr Glu Pro Thr Leu
145                 150                 155                 160

Glu Leu Leu His Ser Ser Cys Asp Pro Asn Ala Phe His Ser Thr Ile
                165                 170                 175

Gln Leu Tyr Cys Phe Ile Tyr Gly His Ile Leu Asn Asp Val Ser Val
            180                 185                 190

Ser Trp Leu Met Asp Asp Arg Glu Ile Thr Asp Thr Leu Ala Gln Thr
            195                 200                 205

Val Leu Ile Lys Glu Glu Gly Lys Leu Ala Ser Thr Cys Ser Lys Leu
210                 215                 220

Asn Ile Thr Glu Gln Gln Trp Met Ser Glu Ser Thr Phe Thr Cys Lys
225                 230                 235                 240

Val Thr Ser Gln Gly Val Asp Tyr Leu Ala His Thr Arg Arg Cys Pro
            245                 250                 255

Asp His Glu Pro Arg Gly Val Ile Thr Tyr Leu Ile Pro Pro Ser Pro
            260                 265                 270

Leu Asp Leu Tyr Gln Asn Gly Ala Pro Lys Leu Thr Cys Leu Val Val
            275                 280                 285

Asp Leu Glu Ser Glu Lys Asn Val Asn Val Thr Trp Asn Gln Glu Lys
            290                 295                 300

Lys Thr Ser Val Ser Ala Ser Gln Trp Tyr Thr Lys His His Asn Asn
305                 310                 315                 320

Ala Thr Thr Ser Ile Thr Ser Ile Leu Pro Val Val Ala Lys Asp Trp
            325                 330                 335

Ile Glu Gly Tyr Gly Tyr Gln Cys Ile Val Asp His Pro Asp Phe Pro
            340                 345                 350

Lys Pro Ile Val Arg Ser Ile Thr Lys Thr Pro Gly Gln Arg Ser Ala
            355                 360                 365

Pro Glu Val Tyr Val Phe Pro Pro Glu Glu Ser Glu Asp Lys
            370                 375                 380

Arg Thr Leu Thr Cys Leu Ile Gln Asn Phe Phe Pro Glu Asp Ile Ser
385                 390                 395                 400

Val Gln Trp Leu Gly Asp Gly Lys Leu Ile Ser Asn Ser Gln His Ser
            405                 410                 415

Thr Thr Thr Pro Leu Lys Ser Asn Gly Ser Asn Gln Gly Phe Phe Ile
            420                 425                 430

Phe Ser Arg Leu Glu Val Ala Lys Thr Leu Trp Thr Gln Arg Lys Gln
            435                 440                 445

Phe Thr Cys Gln Val Ile His Glu Ala Leu Gln Lys Pro Arg Lys Leu
            450                 455                 460

Glu Lys Thr Ile Ser Thr Ser Leu Gly Asn Thr Ser Leu Arg Pro Ser
465                 470                 475                 480

<210> SEQ ID NO 17
<211> LENGTH: 864
<212> TYPE: DNA
<213> ORGANISM: Artificial Sequence
<220> FEATURE:

<223> OTHER INFORMATION: Chimeric Protein: mSa-CD3Z
<220> FEATURE:
<221> NAME/KEY: CDS
<222> LOCATION: (1)..(864)

<400> SEQUENCE: 17

| | | | | | | | | | | | | | | | | |
|---|---|---|---|---|---|---|---|---|---|---|---|---|---|---|---|---|
| atg | aag | tgg | aaa | gcc | ctt | ttt | acc | gcc | gcc | att | ctg | caa | gcg | caa | ttg | 48 |
| Met | Lys | Trp | Lys | Ala | Leu | Phe | Thr | Ala | Ala | Ile | Leu | Gln | Ala | Gln | Leu | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccg | atc | act | gaa | gcc | gca | tcg | gcc | gag | gcc | ggt | atc | act | gga | acc | tgg | 96 |
| Pro | Ile | Thr | Glu | Ala | Ala | Ser | Ala | Glu | Ala | Gly | Ile | Thr | Gly | Thr | Trp | |
| | | | 20 | | | | | 25 | | | | | 30 | | | |

| | | | | | | | | | | | | | | | | |
|---|---|---|---|---|---|---|---|---|---|---|---|---|---|---|---|---|
| tac | aac | cag | cac | gga | tcc | aca | ttc | acc | gtg | acc | gcc | ggt | gct | gac | gga | 144 |
| Tyr | Asn | Gln | His | Gly | Ser | Thr | Phe | Thr | Val | Thr | Ala | Gly | Ala | Asp | Gly | |
| | | 35 | | | | | 40 | | | | | 45 | | | | |

| | | | | | | | | | | | | | | | | |
|---|---|---|---|---|---|---|---|---|---|---|---|---|---|---|---|---|
| aat | ctg | acc | gga | cag | tac | gag | aat | cgg | gct | cag | ggc | acc | ggt | tgt | cag | 192 |
| Asn | Leu | Thr | Gly | Gln | Tyr | Glu | Asn | Arg | Ala | Gln | Gly | Thr | Gly | Cys | Gln | |
| | 50 | | | | | 55 | | | | | 60 | | | | | |

| | | | | | | | | | | | | | | | | |
|---|---|---|---|---|---|---|---|---|---|---|---|---|---|---|---|---|
| aac | tcc | cct | tac | acc | ctc | act | ggg | aga | tac | aac | ggc | acc | aag | ctg | gaa | 240 |
| Asn | Ser | Pro | Tyr | Thr | Leu | Thr | Gly | Arg | Tyr | Asn | Gly | Thr | Lys | Leu | Glu | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| tgg | agg | gtg | gaa | tgg | aac | aac | tcc | acc | gaa | aac | tgc | cat | tcc | cgc | act | 288 |
| Trp | Arg | Val | Glu | Trp | Asn | Asn | Ser | Thr | Glu | Asn | Cys | His | Ser | Arg | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| gag | tgg | cgc | gga | cag | tat | cag | ggg | gga | gcc | gaa | gcg | cgg | atc | aac | acc | 336 |
| Glu | Trp | Arg | Gly | Gln | Tyr | Gln | Gly | Gly | Ala | Glu | Ala | Arg | Ile | Asn | Thr | |
| | | | 100 | | | | | 105 | | | | | 110 | | | |

| | | | | | | | | | | | | | | | | |
|---|---|---|---|---|---|---|---|---|---|---|---|---|---|---|---|---|
| caa | tgg | aac | ctg | acc | tac | gag | ggc | ggg | agc | gga | ccc | gcg | act | gag | cag | 384 |
| Gln | Trp | Asn | Leu | Thr | Tyr | Glu | Gly | Gly | Ser | Gly | Pro | Ala | Thr | Glu | Gln | |
| | | 115 | | | | | 120 | | | | | 125 | | | | |

| | | | | | | | | | | | | | | | | |
|---|---|---|---|---|---|---|---|---|---|---|---|---|---|---|---|---|
| ggc | cag | gat | acg | ttc | act | aag | gtc | aag | ggc | agc | gca | tca | ggc | tcg | gga | 432 |
| Gly | Gln | Asp | Thr | Phe | Thr | Lys | Val | Lys | Gly | Ser | Ala | Ser | Gly | Ser | Gly | |
| | 130 | | | | | 135 | | | | | 140 | | | | | |

| | | | | | | | | | | | | | | | | |
|---|---|---|---|---|---|---|---|---|---|---|---|---|---|---|---|---|
| cag | agc | ttt | ggc | ctg | ctg | gat | ccc | aaa | ctc | tgc | tac | ctg | ctg | gat | gga | 480 |
| Gln | Ser | Phe | Gly | Leu | Leu | Asp | Pro | Lys | Leu | Cys | Tyr | Leu | Leu | Asp | Gly | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| atc | ctc | ttc | atc | tat | ggt | gtc | att | ctc | act | gcc | ttg | ttc | ctg | aga | gtg | 528 |
| Ile | Leu | Phe | Ile | Tyr | Gly | Val | Ile | Leu | Thr | Ala | Leu | Phe | Leu | Arg | Val | |
| | | | | 165 | | | | | 170 | | | | | 175 | | |

| | | | | | | | | | | | | | | | | |
|---|---|---|---|---|---|---|---|---|---|---|---|---|---|---|---|---|
| aag | ttc | agc | agg | agc | gca | gac | gcc | ccc | gcg | tac | cag | cag | ggc | cag | aac | 576 |
| Lys | Phe | Ser | Arg | Ser | Ala | Asp | Ala | Pro | Ala | Tyr | Gln | Gln | Gly | Gln | Asn | |
| | | | 180 | | | | | 185 | | | | | 190 | | | |

| | | | | | | | | | | | | | | | | |
|---|---|---|---|---|---|---|---|---|---|---|---|---|---|---|---|---|
| cag | ctc | tat | aac | gag | ctc | aat | cta | gga | cga | aga | gag | gag | tac | gat | gtt | 624 |
| Gln | Leu | Tyr | Asn | Glu | Leu | Asn | Leu | Gly | Arg | Arg | Glu | Glu | Tyr | Asp | Val | |
| | | 195 | | | | | 200 | | | | | 205 | | | | |

| | | | | | | | | | | | | | | | | |
|---|---|---|---|---|---|---|---|---|---|---|---|---|---|---|---|---|
| ttg | gac | aag | aga | cgt | ggc | cgg | gac | cct | gag | atg | ggg | gga | aag | ccg | cag | 672 |
| Leu | Asp | Lys | Arg | Arg | Gly | Arg | Asp | Pro | Glu | Met | Gly | Gly | Lys | Pro | Gln | |
| | 210 | | | | | 215 | | | | | 220 | | | | | |

| | | | | | | | | | | | | | | | | |
|---|---|---|---|---|---|---|---|---|---|---|---|---|---|---|---|---|
| aga | agg | aag | aac | cct | cag | gaa | ggc | ctg | tac | aat | gaa | ctg | cag | aaa | gat | 720 |
| Arg | Arg | Lys | Asn | Pro | Gln | Glu | Gly | Leu | Tyr | Asn | Glu | Leu | Gln | Lys | Asp | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| aag | atg | gcg | gag | gcc | tac | agt | gag | att | ggg | atg | aaa | ggc | gag | cgc | cgg | 768 |
| Lys | Met | Ala | Glu | Ala | Tyr | Ser | Glu | Ile | Gly | Met | Lys | Gly | Glu | Arg | Arg | |
| | | | | 245 | | | | | 250 | | | | | 255 | | |

| | | | | | | | | | | | | | | | | |
|---|---|---|---|---|---|---|---|---|---|---|---|---|---|---|---|---|
| agg | ggc | aag | ggg | cac | gat | ggc | ctt | tac | cag | ggt | ctc | agt | aca | gcc | acc | 816 |
| Arg | Gly | Lys | Gly | His | Asp | Gly | Leu | Tyr | Gln | Gly | Leu | Ser | Thr | Ala | Thr | |
| | | | 260 | | | | | 265 | | | | | 270 | | | |

| | | | | | | | | | | | | | | | | |
|---|---|---|---|---|---|---|---|---|---|---|---|---|---|---|---|---|
| aag | gac | acc | tac | gac | gcc | ctt | cac | atg | cag | gcc | ctg | ccc | cct | cgc | taa | 864 |
| Lys | Asp | Thr | Tyr | Asp | Ala | Leu | His | Met | Gln | Ala | Leu | Pro | Pro | Arg | | |
| | | 275 | | | | | 280 | | | | | 285 | | | | |

```
<210> SEQ ID NO 18
<211> LENGTH: 287
<212> TYPE: PRT
<213> ORGANISM: Artificial Sequence
<220> FEATURE:
<223> OTHER INFORMATION: Synthetic Construct

<400> SEQUENCE: 18

Met Lys Trp Lys Ala Leu Phe Thr Ala Ala Ile Leu Gln Ala Gln Leu
1               5                   10                  15

Pro Ile Thr Glu Ala Ala Ser Ala Glu Ala Gly Ile Thr Gly Thr Trp
                20                  25                  30

Tyr Asn Gln His Gly Ser Thr Phe Thr Val Thr Ala Gly Ala Asp Gly
            35                  40                  45

Asn Leu Thr Gly Gln Tyr Glu Asn Arg Ala Gln Gly Thr Gly Cys Gln
        50                  55                  60

Asn Ser Pro Tyr Thr Leu Thr Gly Arg Tyr Asn Gly Thr Lys Leu Glu
65                  70                  75                  80

Trp Arg Val Glu Trp Asn Asn Ser Thr Glu Asn Cys His Ser Arg Thr
                85                  90                  95

Glu Trp Arg Gly Gln Tyr Gln Gly Gly Ala Glu Ala Arg Ile Asn Thr
            100                 105                 110

Gln Trp Asn Leu Thr Tyr Glu Gly Gly Ser Gly Pro Ala Thr Glu Gln
        115                 120                 125

Gly Gln Asp Thr Phe Thr Lys Val Lys Gly Ser Ala Ser Gly Ser Gly
130                 135                 140

Gln Ser Phe Gly Leu Leu Asp Pro Lys Leu Cys Tyr Leu Leu Asp Gly
145                 150                 155                 160

Ile Leu Phe Ile Tyr Gly Val Ile Leu Thr Ala Leu Phe Leu Arg Val
                165                 170                 175

Lys Phe Ser Arg Ser Ala Asp Ala Pro Ala Tyr Gln Gln Gly Gln Asn
            180                 185                 190

Gln Leu Tyr Asn Glu Leu Asn Leu Gly Arg Arg Glu Glu Tyr Asp Val
        195                 200                 205

Leu Asp Lys Arg Arg Gly Arg Asp Pro Glu Met Gly Gly Lys Pro Gln
210                 215                 220

Arg Arg Lys Asn Pro Gln Glu Gly Leu Tyr Asn Glu Leu Gln Lys Asp
225                 230                 235                 240

Lys Met Ala Glu Ala Tyr Ser Glu Ile Gly Met Lys Gly Glu Arg Arg
                245                 250                 255

Arg Gly Lys Gly His Asp Gly Leu Tyr Gln Gly Leu Ser Thr Ala Thr
            260                 265                 270

Lys Asp Thr Tyr Asp Ala Leu His Met Gln Ala Leu Pro Pro Arg
        275                 280                 285

<210> SEQ ID NO 19
<211> LENGTH: 7
<212> TYPE: PRT
<213> ORGANISM: Artificial Sequence
<220> FEATURE:
<223> OTHER INFORMATION: Linker

<400> SEQUENCE: 19

Gly Ser Ala Ser Gly Ser Gly
1               5
```

BIOSENSOR SYSTEM FOR THE RAPID DETECTION OF ANALYTES

CROSS-REFERENCE TO RELATED APPLICATIONS

This patent application is a divisional of U.S. patent application Ser. No. 15/086,769 filed on Mar. 31, 2016 and entitled "Biosensor System for Rapid Detection of Analytes", which claimed the benefit of U.S. Provisional Patent Application Ser. No. 62/140,920 filed on Mar. 31, 2015 and entitled "System for Rapid Detection of Analytes" and U.S. Provisional Patent Application Ser. No. 62/245,595 filed on Oct. 23, 2015 and entitled "Systems and Devices for the Rapid Detection of Analytes", the disclosures of which are incorporated by reference herein in their entirety and made part of the present U.S. utility patent application for all purposes.

BACKGROUND OF THE INVENTION

The described invention relates in general to systems, devices, and methods for detecting various analytes in biological samples or other sample types, and more specifically to a biosensor-based system for detecting and identifying analytes of interest in real time based on the emission of a detectable signal when the biosensor reacts with an analyte of interest in a sample being tested.

In generic terms, a biosensor is a system or device for the detection of an analyte that combines a sensitive biological component with a physicochemical detector component. The components of a typical biosensor system include a biological element, a transducer or detector element, and associated electronics or signal processors that display test results in a meaningful and useful manner. The biological element typically includes biological material such as tissue, microorganisms, organelles, cell receptors, enzymes, antibodies, nucleic acids, and the like that may be created by known biological engineering processes. The transducer or detector element works in a physicochemical manner (e.g., optical, piezoelectric, and/or electrochemical) that transforms the signal resulting from the interaction of the analyte with the biological element into another signal that can be more easily measured and quantified. Biosensors originated from the integration of molecular biology and information technology (e.g., microcircuits, optical fibers, etc.) to qualify or quantify biomolecule-analyte interactions such as antibody-antigen interactions. Considering that there is great demand for rapid, sensitive, easy-to-handle, and cost-effective detection tools for detecting infectious agents, pathogens or/and toxins in food (see, for example, Mead et al., *Food Related Illness and Death in the United States*, Emerging Infectious Diseases; Vol. 5, No. 5, September-October 1999 (607-625), which is incorporated by reference herein, in its entirety), there is an ongoing need for the utilization of biosensors in real-time, field-portable devices and instruments for the detection and identification of infectious agents, pathogenic microorganisms, toxins, and other contaminants in foods and many other items.

SUMMARY OF THE INVENTION

The following provides a summary of certain exemplary embodiments of the present invention. This summary is not an extensive overview and is not intended to identify key or critical aspects or elements of the present invention or to delineate its scope.

In accordance with one aspect of the present invention, a first system for the rapid detection of analytes is provided. An exemplary embodiment of this first system includes a living, engineered biosensor cell that is derived from a cellular component of the mammalian immune system; a reporter protein that is engineered into and produced by the living, engineered biosensor cell and that emits a detectable signal in response to certain predetermined changes in the cytosol of the living, engineered biosensor cell; a signal transduction pathway engineered into or occurring naturally within the living, engineered biosensor cell that controls a biological process within the cytosol of the living, engineered biosensor cell, wherein the biological process, when it occurs, causes the reporter protein to emit a detectable signal; at least one type of detector molecule, wherein each detector molecule is adapted to bind to a specific analyte; at least one analyte that binds to the detector molecule and that is specific to that analyte; a plurality of transmembrane, non-antibody signal transducing elements expressed by the living, engineered biosensor cell, wherein each signal transducing element is adapted to receive a detector molecule; and wherein upon the binding of a sufficient number of analytes to a sufficient number of detector molecules that are themselves bound to transmembrane non-antibody signal transducing elements, an aggregation of signal transducing elements occurs on the biosensor cell surface, the signal transduction pathway is activated, the biological process occurs, and the detectable signal is emitted by the reporter protein.

In accordance with another aspect of the present invention, a second system for the rapid detection of analytes is provided. An exemplary embodiment of this second system includes a living, engineered biosensor cell, wherein the living, engineered biosensor cell is derived from a cellular component of the mammalian immune system, and wherein the living, engineered biosensor cell expresses a plurality of at least one predetermined type of receptor molecule on the surface thereof; a reporter protein, wherein the reporter protein is engineered into and expressed by the living, engineered biosensor cell, and wherein the reporter protein emits a detectable signal in response to certain predetermined changes in the cytosol of the living, engineered cell; a signal transduction pathway engineered into or occurring naturally within the living, engineered biosensor cell, wherein the signal transduction pathway controls a biological process within the cytosol of the living, engineered biosensor cell, and wherein the biological process, when it occurs, causes the reporter protein to emit a detectable signal; at least one type of detector molecule, wherein each detector molecule is adapted to bind to a specific analyte; at least one analyte, wherein the at least one analyte binds to the detector molecule that is specific to that analyte; a plurality of soluble non-antibody signal transducing elements, wherein each soluble signal transducing element is adapted to bind to a receptor molecule and to a detector molecule; and wherein upon the binding of a sufficient number of analytes to a sufficient number of detector molecules to a sufficient number of non-antibody signal transducing elements that are themselves bound to the cell surface receptor molecules, an aggregation of the receptor molecules occurs, the signal transduction pathway is activated, the biological process occurs, and the detectable signal is emitted by the reporter protein.

In accordance with still another aspect of the present invention, a biosensor for the rapid detection of analytes in a sample is provided. This biosensor includes a living, engineered cell, wherein the living, engineered cell is derived from a cellular component of the mammalian immune system (i.e., an immunocyte); a reporter protein, wherein the reporter protein is engineered into and expressed by the living, engineered cell, and wherein the reporter protein emits a detectable signal in response to certain predetermined changes in the cytosol of the living, engineered cell; a signal transduction pathway engineered into or occurring naturally within the living, engineered cell, wherein the signal transduction pathway controls a biological process within the cytosol of the living, engineered biosensor cell, and wherein the biological process, when it occurs, causes the reporter protein to emit a detectable signal; and a plurality of non-antibody signal transducing elements that directly or indirectly bind to an analyte in a sample to be analyzed, wherein the bound non-antibody signal transducing elements then cooperate with the biosensor cell to directly or indirectly activate the signal transduction pathway.

Additional features and aspects of the present invention will become apparent to those of ordinary skill in the art upon reading and understanding the following detailed description of the exemplary embodiments. As will be appreciated by the skilled artisan, further embodiments of the invention are possible without departing from the scope and spirit of the invention. Accordingly, the drawings and associated descriptions are to be regarded as illustrative and not restrictive in nature.

BRIEF DESCRIPTION OF THE DRAWINGS

The accompanying drawings, which are incorporated into and form a part of the specification, schematically illustrate one or more exemplary embodiments of the invention and, together with the general description given above and detailed description given below, serve to explain the principles of the invention, and wherein:

FIGS. 2a-b are illustrations of a second biosensor in accordance with an exemplary embodiment of the present invention, wherein MC/9 mast cells have been engineered to produce aequorin, and wherein the MC/9 cells express the native receptor FcεRI, which binds to the soluble non-antibody signal transducing element IgGbp-IgE;

FIGS. 3a-b are illustrations of a third biosensor in accordance with an exemplary embodiment of the present invention, wherein MC/9 mast cells have been engineered to produce aequorin, and wherein the MC/9 cells express the native receptor FcεRI, which binds to the soluble non-antibody signal transducing element IgGbp-IgE, which has been excreted by the MC/9 mast cells;

DETAILED DESCRIPTION OF THE INVENTION

Figure 1A:
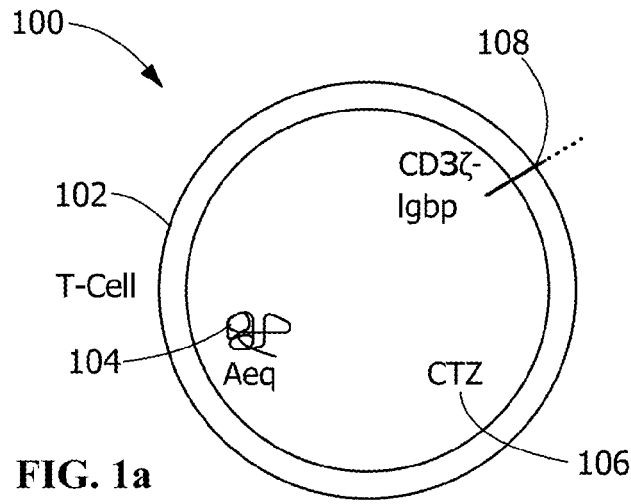
FIGS. 1a-b are illustrations of a first biosensor in accordance with an exemplary embodiment of the present invention, wherein Jurkat T cells have been engineered to produce aequorin and to express the transmembrane non-antibody signal transducing element IgGbp-CD3ζ.

Exemplary embodiments of the present invention are now described with reference to the Figures. Although the following detailed description contains many specifics for purposes of illustration, a person of ordinary skill in the art will appreciate that many variations and alterations to the following details are within the scope of the invention. Accordingly, the following embodiments of the invention are set forth without any loss of generality to, and without imposing limitations upon, the claimed invention.

The present invention relates in general to systems, devices, and methods for detecting various analytes in biological samples or other sample types, and more specifically to a biosensor-based system for detecting and identifying analytes of interest in real time based on the emission of a detectable signal when the biosensor reacts with an analyte of interest in a sample being tested. The engineered cells of the present invention are extremely sensitive and effective biosensors and because these biosensor cells have an intrinsic detection capacity, they provide a versatile system that can be readily adapted to detect a wide variety of different infectious agents or other targets by simply selecting alternative soluble detector (e.g., antibody) molecules with specificity for a particular pathogen or other target of interest. Furthermore, the system of this invention can be readily configured for multiplex detection of several infectious agents or other analytes in a single assay, providing for great flexibility and utility. The versatility of the present invention is derived from a unique combination of elements and in particular from the combination of a universal biosensor cell with a specific soluble detector (e.g., antibody). The universal biosensor cell has the capacity to respond to the presence of essentially any target molecule that can be recognized by the detector molecule. Because, in some embodiments, the detector or detector antibody is added to the system as a soluble factor, the system may be configured to detect an alternative target by simply selecting an appropriate alternate detector or detector antibody. The specificity of the disclosed system is determined by the detector molecule, which is selected based on its specificity and affinity for a target molecule that is characteristic of an infectious agent or other target analyte. The combination of this universal biosensor cell and soluble detector also enables the construction of multiplex assays by simply including a plurality of detector molecules (e.g., antibodies) within the test system, wherein the target molecules are selected based on their specificity for alternative infectious agents or other analytes.

Genetic manipulation and modification of the biosensor cell types used with this invention typically involve the use of appropriately selected gene delivery vehicles that contain genetic elements that function efficiently in the cell type of choice. For example, it is useful to employ a promoter element that directs high level expression of introduced transgenes in the specific biosensor cell of choice. In an exemplary embodiment of this invention, such a promoter element may be derived directly from the biosensor cell itself and then used to express a transgene of interest. In another embodiment of this invention, an appropriate element may be determined empirically by comparing the function of alternative promoter elements in the context of alternative gene delivery vehicles in order to identify effective promoter, transgene, vector combinations for the cell type of choice. Transgenes such as the gene encoding a luminescent reporter protein may be introduced into the biosensor cell using standard techniques such as electroporation or chemical transfection reagents such as, for example, lipofectamine. Other genetic engineering methods known to those of ordinary skill in the art are also compatible with the present invention.

In a generic embodiment, the present invention provides a system and method for rapid detection of analytes that includes the following components: (i) a living, engineered biosensor cell, wherein the living engineered biosensor cell is a component of the mammalian immune system; (ii) a reporter protein, wherein the reporter protein is expressed by the living, engineered biosensor cell, and wherein the reporter protein emits a detectable signal in response to certain predetermined changes in the cytosol of the living, engineered cell; (iii) a signal transduction pathway expressed by the living, engineered biosensor cell, wherein the signal transduction pathway controls a biological or biochemical process within the cytosol of the living, engineered biosensor cell, and wherein the biological or biochemical process, when it occurs, causes the reporter protein to emit a detectable signal; (iv) at least one type of detector molecule, wherein each detector molecule is adapted to bind to a specific analyte; (v) at least one analyte, wherein the at least one analyte binds to the detector molecule that is specific to that analyte; (vi) a plurality of non-antibody signal transducing elements that are either expressed by the living, engineered biosensor cell or that actively bind to a receptor or a receptor component expressed by the living, engineered biosensor cell, wherein each signal transducing element is adapted to receive a detector molecule. Upon the binding of a sufficient number of analytes to a sufficient number of detector molecules that are themselves bound to the non-antibody signal transducing elements, an aggregation of signal transducing elements occurs on the cell surface, the signal transduction pathway is activated, the biochemical process occurs, and the detectable signal is emitted by the reporter protein. This system may also include a device for mixing the living cells together with soluble components and a sample containing an analyte or infectious agent of interest while maintaining the viability and functionality of the living biosensor cell, and a detector for detecting the signal emitted by the biosensor cell.

Living, Engineered Biosensor Cell

Exemplary embodiments of this invention include a living, engineered biosensor cell that is typically a component of the mammalian immune system, e.g., an immunocyte. In certain embodiments of this invention, the biosensor cell is a human or mouse B cell. B cells or B lymphocytes, are a type of white blood cell of the lymphocyte subtype that function in the humoral immunity component of the adaptive immune system by secreting antibodies. In other embodiments of this invention, the biosensor cell is a human or mouse T cell. T cells or T lymphocytes are another type of lymphocyte that play a central role in cell-mediated immunity as part of the adaptive immune system. T cells are distinguishable from other lymphocytes due to the presence of a T-cell receptor on the cell surface. In other embodiments of this invention, the biosensor cell is a mast cell. A mast cell is also a type of white blood cell known as a granulocyte that is derived from the myeloid stem cell that is a part of the immune and neuroimmune systems. Other types of cells are compatible with this invention, including basophils, which are another type of white blood cell, and which are similar in both appearance and function to mast cells.

Reporter Protein

Exemplary embodiments of this invention include a reporter element, such as a reporter protein or enzyme that is produced or expressed by the living, engineered biosensor cell. The reporter protein emits a detectable signal in response to certain predetermined changes in the cytosol of the living, engineered biosensor cell. In certain embodiments of this invention, the reporter protein is a bioluminescent photoprotein such as aequorin, which is derived from the hydrozoan *Aequorea Victoria*. Aequorin has been previously used for engineering living biosensor cells to produce light signals in response to activation of a wide variety of signal transduction pathways; thus, various methods for manipulating the production of aequorin in living cells are well known to the skilled artisan. In particular, a skilled artisan may selected and employ any appropriate gene delivery vehicle such as, for example, bacterial plasmid vectors or viral vectors, for introducing the appropriate genetic material into the biosensor cells. Production of the reporter protein within the biosensor cell will then be controlled by expression of the introduced genetic material. One having ordinary skill in the art will also appreciate that other photoproteins or other types of reporter proteins, enzymes, and molecules may be incorporated into and utilized with various alternate embodiments of the present invention.

Signal Transduction Pathway

Exemplary embodiments of this invention include a signal transduction pathway expressed by the living, engineered biosensor cell. The signal transduction pathway controls at least one biological process within the cytosol of the living, engineered cell, and the at least one biological process, when it occurs, causes the reporter protein to emit a detectable signal. In certain embodiments of this invention, the signal transduction pathway is any biochemical pathway in which an increase in intracellular $Ca2+$ concentration is induced in response to activation of a cell surface signal transducing molecule, such as a receptor protein. The biosensor cells used with this invention may be selected from a set of living cells that are capable of producing an increase in cytoplasmic $Ca2+$ in response to activation of a cell surface signal transduction molecule. For example, B cells, T cells, and mast cells have the capacity to induce an increase in $Ca2+$ concentration in response to activation of cell surface signal transducing molecules such as the B cell receptor, the T cell receptor, and the Fc epsilon receptor (mast cells), respectively.

Because mammalian cells growing in culture typically generate populations of cells in which specific individual cells may have differing capacities to induce an increase in $Ca2+$ concentration, it is useful to select for or screen for subpopulations of cells or clonal cell lines that have a robust ability to generate the $Ca2+$ signal. This may be accomplished by analyzing induction of an aequorin induced flash, for example. In particular, the transfectants created by the introduction of transgenes into a cell are a mixed population of cells derived from a large number of independent gene insertion events. Thus, when constructing a biosensor cell it is useful to screen or select specific subsets of cells or clonal cell lines that have efficient signal transduction capabilities together with useful levels of expression of introduced transgenes. It is particularly useful to use fluorescence-activated cell sorting (FACS) technology to select for subpopulations of high expressing cells or to generate clonal cell lines for this purpose.

As previously stated, aequorin has been used previously for engineering living biosensor cells to produce light signals in response to activation of a wide variety of signal transduction pathways, particularly wherein such signal transduction pathways lead to an increase in cytoplasmic Ca2+ ions within a living cell. In certain embodiments of this invention, biosensor cells that produce aequorin as the reporter protein are charged with coelenterazine (CTZ) prior to their use in a detection assay. This charging step covalently links the aequorin to a hydrophobic prosthetic group (e.g., CTZ) and upon calcium (Ca2+) binding, the CTZ undergoes an irreversible reaction that includes a conformation change, and emits blue light (at 469 nm).

Detector Molecule

Exemplary embodiments of this invention include at least one type of detector element such as a detector molecule, wherein each detector molecule is adapted to bind to a specific target analyte. The detector molecule may a soluble antibody that is not in any way expressed by the biosensor cells. The particular detector molecule used with the present invention is selected based on its ability to unambiguously identify the target analyte of interest. In an exemplary embodiment, the detector molecule is a soluble antibody such as a commercially available IgG that is specific for a particular analyte, such as an infectious agent. In another exemplary embodiment, the detector molecule is a biotinylated molecule (or streptavidin-based molecule) that is specific for a predetermined analyte such as, for example, a biotinylated autoantigen molecule that is specific for an anti-autoantigen antibody. A detector or target molecule according to this invention may include an autoantigen or an autoantibody associated with an autoimmune disease. Representative autoimmune diseases or disorders include rheumatoid arthritis (RA), juvenile RA (JRA), diabetes mellitus type 1, systemic lupus erythematosus, Hashimoto's thyroiditis, Graves' disease, scleroderma, celiac disease, Crohn's disease, ulcerative colitis, Sjogren's syndrome, multiple sclerosis, Goodpasture's syndrome, Addison's disease, Wegener's granulomatosis, primary biliary cirrhosis, sclerosing cholangitis, autoimmune hepatitis, polymyalgia rheumatica, temporal arteritis/giant cell arteritis, and Guillain-Barre syndrome. Detector or target molecules may also comprise tumor-specific or tumor-associated antigens or antibodies to such antigens; or biologically active molecules, such as EGF, peptide hormones, including insulin and growth hormone, cytokines, interleukins, interferons, TNF, etc. or antibodies to such biologically active molecules.

Analyte and Test Sample

An intended use of the present invention is the detection of various analytes that are or might be present within samples to be tested. In an exemplary embodiment of this invention, an analyte that is to be detected will bind to a detector molecule, such as a soluble antibody, that is specific to that analyte. A sample to be tested may be taken from a large number of food sources, including: (i) meats such as beef, pork, lamb, bison, poultry, and seafood; and (ii) plants and vegetables. A sample to be tested may also be taken from many other sources such as water, consumable fluids, preservative fluids, and bodily fluids such as blood. Analytes that may be detected include virtually anything that will bind with specificity to the detector or detector molecule such as chemicals, toxins, and infectious agents such as viruses, bacteria, and other biological materials or agents. In an exemplary embodiment of this invention, the specific infectious agent is *Escherichia coli*, although other infectious agents (such as *Salmonella*, *Listeria*, and *Campylobacter*) and contaminants may be detected with the present invention. *Escherichia coli* O157 H7, O26, O45, O103, O111, O121, and O145, in either separate assays or multiplexed assays, may all potentially be detected using this invention.

The present invention is capable of detecting many different analytes including meat pathogens, and those found on spinach, lettuce, and other vegetables and foods. An analyte may contain one or more epitopes of an antigen or allergen, including both linear or conformation epitopes; it may also contain one or more ligands or receptors recognized by reciprocal receptors or ligands. Exemplary analytes include a bacterium, such as *Bacillus* (e.g., *B. anthracis*), Enterobacteriaceae (e.g., *Salmonella, Escherichia coli, Yersinia pestis, Klebsiella,* and *Shigella*), *Yersinia* (e.g., *Y. pestis* or *Y. enterocolitica*), *Staphylococcus* (e.g., *S. aureus*), *Streptococcus, Gonorrheae, Enterococcus* (e.g., *E. faecalis*), *Listeria* (e.g., *L. monocytogenes*), *Brucella* (e.g., *B. abortus, B. melitensis,* or *B. suis*), *Vibrio* (e.g., *V. cholerae*), *Corynebacterium diphtheria, Pseudomonas* (e.g., *P. pseudomallei* or *P. aeruginosa*), *Burkholderia* (e.g., *B. mallei* or *B. pseudomallei*), *Shigella* (e.g., *S. dysenteriae*), *Rickettsia* (e.g., *R. rickettsii, R. prowazekii,* or *R. typhi*), *Francisella tularensis, Chlamydia psittaci, Coxiella burnetii, Mycoplasma* (e.g., *M. mycoides*), etc.; allergens, such as peanut dust, mycotoxins, mold spores, or bacterial spores such as *Clostridium botulinum* and *C. perfringens*; toxins, such as ricin, mycotoxin, tetrodotoxin, anthrax toxin, botulinum toxin, staphylococcal entertoxin B, or saxitoxin; a virus, such as Adenoviridae (e.g., adenovirus), Arenaviridae (e.g., Machupo virus), Bunyaviridae (e.g., Hantavirus or Rift Valley fever virus), Coronaviridae, Orthomyxoviridae (e.g., influenza viruses), Filoviridae (e.g., Ebola virus and Marburg virus), Flaviviridae (e.g., Japanese encephalitis virus and Yellow fever virus), Hepadnaviridae (e.g., hepatitis B virus), Herpesviridae (e.g., herpes simplex viruses), Papovaviridae (e.g., papilloma viruses), Paramyxoviridae (e.g., respiratory syncytial virus, measles virus, mumps virus, or parainfluenza virus), Parvoviridae, Picornaviridae (e.g., polioviruses), Poxviridae (e.g., *variola* viruses), Reoviridae (e.g., rotaviruses), Retroviridae (e.g., human T cell lymphotropic viruses (HTLV) and human immunodeficiency viruses (HIV)), Rhabdoviridae (e.g., rabies virus), and Togaviridae (e.g., encephalitis viruses, yellow fever virus, and rubella virus)); a protozoon, such as *Cryptosporidium parvum, Encephalitozoa, Plasmodium, Toxoplasma gondii, Acanthamoeba, Entamoeba histolytica, Giardia lamblia, Trichomonas vaginalis, Leishmania,* or *Trypanosoma* (e.g., *T. brucei* and *T. Cruzi*); a helminth, such as cestodes (tapeworms), trematodes (flukes), or nematodes (roundworms, e.g., *Ascaris lumbricoides, Trichuris trichiura, Necator americanus,* or *Ancylostoma duodenale*); a parasite (e.g., any protozoa or helminths described herein); a fungus, such as Aspergilli, Candidae, *Coccidioides immitis*, and Cryptococci; an environmental contaminant; a water additive; an agricultural marker; a nucleic acid (e.g., oligonucleotides, polynucleotides, nucleotides, nucleosides, molecules of DNA, or molecules of RNA, including a chromosome, a plasmid, a viral genome, a primer, or a gene); a protein (e.g., a glycoprotein, a metalloprotein, an enzyme, a prion, or an immunoglobulin); a metabolite; a sugar; a lipid; a lipopolysaccharide; a salt; or an ion. Targets also include foodborne pathogens, such as *Salmonella* (e.g., *Salmonella Typhimurium*), pathogenic *E. coli* (e.g., O157:H7), *Bacillus* (e.g., *B. cereus*), *Clostridium botulinum, Listeria monocytogenes, Yersinia* (e.g., *Y. enterocolitica*), Norovirus (e.g., Norwalk virus), *Shigella, Staphylococcus aureus, Toxoplasma gondii, Vibrio* (e.g., *V. vulnificus, V. cholera, V. parahaemolyticus*), *Campylobacter jejuni*, and *Clostridium perfringens*; and weaponized pathogens, such as *Bacillus anthracis, Yersinia pestis, Francisella tularensis, Brucella* (e.g., *B. suis*), *Burkholderia mallei, Burkholderia pseudomallei, Shigella, Clostridium botulinum, Variola* (e.g., *V. major*), Filoviridae (e.g., Ebola virus and Marburg virus), Arenaviridae (e.g., Lassa virus and Machupo virus), *Clostridium perfringens*, any food-borne pathogen (e.g., *Salmonella* species, *Escherichia coli* O157:H7, or *Shigella*), *Chlamydia psittaci, Coxiella burnetii, Staphylococcal aureus, Rickettsia* (e.g., *R. prowazekii* or *R. rickettsii*), Alphavirus (e.g., Venezuelan equine encephalitis virus, eastern equine encephalitis virus, or western equine encephalitis virus), *Vibrio cholerae, Cryptosporidium parvum, Henipavirus* (e.g., Nipah virus), Bunyaviridae (e.g., Hantavirus or Rift Valley fever virus), Flaviviridae (e.g., Japanese encephalitis virus and Yellow fever virus), and *Coccidioides* spp.

Epitopes that can be detected as analytes or portions of an analyte are typically antigenic determinant sites on an antigen to which an immunogolublin (or antigen binding fragment thereof) can specifically bind. Epitopes can be formed both from contiguous amino acids or noncontiguous amino acids juxtaposed by tertiary folding of a protein. Epitopes can be found on the Fab (variable) region of immunoglobulins (referred to as "idiotypic determinants") and comprise the immunoglobulin's "idiotype". The epitope and antigen can be naturally occurring or artificially produced. Depending on the nature of the epitope or antigen, the epitope or antigen can be isolated or purified from a matrix or substance of origin, synthesized, or recombinantly produced, for example. Epitopes and antigens useful as analytes can be from a human or non-human animal, plant, bacteria, protozoan, parasite, virus, etc. In some embodiments, the analyte is a polypeptide, nucleic acid molecule, carbohydrate, glycoprotein, lipid, lipoprotein, glycolipid, or small molecule. In some embodiments, the analyte is selected from among a cancer antigen, autoantigen, allergen, endogenous antigen, infectious agent antigen, drug (small molecule) antigen, toxin, venom, biologic antigen, environmental antigen, transplant antigen, and implant antigen.

An analyte may comprise an epitope of a cancer antigen. In some embodiments, the analyte is a tumor-associated antigen. In some embodiments, the analyte is a tumor-specific antigen. In some embodiments of the invention, the analyte is a tumor-associated antigen (TAA), and the TAA is a carbohydrate antigen having one or more post-translational modifications that differ from the wild-type protein, comprises a fusion region of a protein resulting from a gene fusion that is present in malignant cells but not present in non-malignant cells, and/or wherein the TAA comprises a receptor tyrosine kinase (RTK) that is deregulated and/or dysfunctional in tumor cells due to autocrine activation, chromosomal translocations, RTK overexpression, or gain-of-function mutations in the RTK gene or protein. In some embodiments of the invention, the analyte is an immunoglobulin expressed by a B-cell malignancy. Examples of B-cell malignancies include, but are not limited to, non-Hodgkin's lymphoma, Hodgkin's lymphoma, chronic lymphocytic leukemia, mantle cell lymphoma and multiple myeloma. Additional B-cell malignancies include, for example. B-cell prolymphocytic leukemia, lymphoplasmocytic leukemia, splenic marginal zone lymphoma, marginal zone lymphoma (extra-nodal and nodal), plasma cell neoplasms (e.g., plasma cell myeloma, plasmacytoma, monoclonal immunoglobulin deposition diseases, heavy chain diseases), and follicular lymphoma (e.g., Grades I, II, III, or IV).

In some embodiments, the analyte is a tumor-associated antigen derived from tumor cells obtained from the subject. In some embodiments, the tumor-associated antigen is one or more antigens selected from among 17-1A, 707-AP, AFP, Annexin II, ART-4, BAGE, BAGE-1, .beta.-catenin, BCG, bcr/abl, Bcr/abl e14a2 fusion junction, bcr-abl (b3a2), bcr-abl (b3a2), bcr-abl p190 (e1a2), bcr-abl p210 (b2a2), bcr-abl p210 (b3a2), bcr-abl p210 (b3a2), bullous pemphigoid antigen-1, CA19-9, CA125, CA215, CAG-3, CAMEL, Cancer-testis antigen, Caspase-8, CCL3, CCL4, CD16, CD20, CD3, CD30, CD55, CD63, CDC27, CDK-4, CDR3, CEA, cluster 5, cluster-5A, cyclin-dependent kinase-4, Cyp-B, DAM-10, DAM-6, Dek-cain, E7, EGFR, EGFRvIII, EGP40, ELF2 M, EpCAM, FucGM1, G250, GA733, GAGE, GAGE-1-8, gastrin cancer associated antigen, GD2, GD3, globoH, glycophorin, GM1, GM2, GM3, GnTV, Gn-T-V, gp100, Her-2/neu, HERV-K-ME, high molecular weight-associated antigen, high molecular weight proteo-glycan (HMPG), HPV-16 E6, HPV-16 E7, HPVE6, HSP70-2M, HST-2, hTERT, human chorionic gonadotropin (HCG), Human milk fat globule (HMFG), iCE, KIAA0205, KK-LC-1, KM-HN-1, L6, LAGE-1, Lcose4Cer, LDLR/FUT, Lewis A, Lewis v/b, M protein, MAGE-1, MVC, MAGE-A1-12, MAGE-C2, MAHGE-3, MART-1/Melan-A, MC1R, ME491, MUC1, MUC2, mucin, MUM-1, MUM-2, MUM-3, mutated p53, Myosin, MZ2-E, N9 neuraminidase, NA88, NA88-A, nasopharyngeal carcinoma antigen, NGA, NK1/c-3, Novel bcr/ablk fusion BCR exons 1, 13, 14 with ABL exons 4, NY-ESO-1/LAGE-2, NY-ESO-1b, OC125, osteosarcoma associated antigen-1, P15, p190 mimor bcr-abl (e1a2), p53, Pm1/RARa, Polysialic acid, PRAME, PSA, PSM, RU1, RU2, SAGE, SART-1, SART-2, SART-3, Sialyl LeA, Sp17, SSX-2, SSX-4, surface immunoglobulin, TAG-1, TAG-2, TEL/AML1, TPI, TRAG-3, TRP-1 (gp75), TRP-2, TRP2-INT2, hTRT, tumor associated glycoprotein-72 (TAG-72), tyrosinase, u-PA, WT1, and XAGE-1b, or an immunogenic fragment of any of the foregoing antigens. In some embodiments, the tumor associated antigen is identified by the SEREX (serological analysis of recombinant cDNA expression library) approach or based on the serological screening of cDNA expression library generated from tumor tissues of various origin or cancer cell lines, and identifying immunogenic tumor proteins based on their reactivity with autologous patient sera. In some embodiments, the analyte is a tumor-associated antigen that is acarbohydrate antigen having one or more post-translational modifications that differ from the wild-type protein. In some embodiments, the tumor-associated antigen comprises a fusion region of a protein resulting from a gene fusion that is resent in malignant cells but not present in non-malignant cells. In some embodiments, the tumor-associated antigen comprises a receptor tyrosine kinase that is deregulated and/or dysfunctional in tumor cells due to autocrine activation, chromosomal translocations, RTK overexpression, or gain-of-function mutations in the RTK gene or protein.

The analyte may comprise an epitope of an antigen of an infectious or noninfectious agent that can be either pathogenic or non-pathogenic to the subject. The analyte can be derived from a mutualistic, parasitic, or commensal microorganism, including any microorganism in a animal or plant biome, such as probiotic or commensal microorganisms in the human digestive tract, mucosal surfaces, or epithelium. In some embodiments, the bacterial pathogen is selected from among *Acinetobacter baumannii* (formerly *Acinetobacter calcoaceticus*), *Actinobacillus*, *Actinomyces pyogenes* (formerly *Corynebacterium pyogenes*), *Actinomyces israelii, nocardia asteroids, N. brasiliensis, Aeromonas hydrophila, Amycolata autotrophica, Archanobacterium haemolyticum* (formerly *Corynebacterium haemolyticum*), Arizona hinshawii—all serotypes, *Bacillus anthracis, Bacteroides fragilis, Bartonella henselae, B. quintana, B. vinsonii, Bordetella* including *B. pertussis, Borrelia recurrentis, B. burgdorferi, Burkholderia* (formerly *Pseudomonas* species) except those listed in BSL III), *Campylobacter coli, C. fetus, C. jejuni, Chlamydia psittaci, C. trachomatis, C. pneumonia, Clostridium botulinum* (neurotoxin producing species), *Clostridium botulinum* neurotoxins, *Cl. chauvoei, Cl. haemolyticum, Cl. histolyticum, Cl. novyi, Cl. septicum, Cl. Tetani, Cl. Perfirngens* epsilon toxin, *Corynebacterium diphtheriae, C. pseudotuberculosis, C. renale, Dermatophilus congolensis, Edwardsiella tarda, Erysipelothrix rhusiopathiae, Escherichia coli*—all enteropathogenic, enterotoxigenic, enteroinvasive and strains bearing K1 antigen, including *E. coli* O157:H7, *Haemophilus ducreyi, H. influenzae, Helicobacter pylori, Klebsiella*—all species except *K. oxytoca* (RG1), *Legionella* including *L. pneumophila, Leptospira interrogans*—all serotypes, *Listeria, Moraxella, Mycobacterium* (except those listed in BSL III) including *M. avium complex, M. asiaticum, M. bovis* BCG vaccine strain, *M. chelonei, M. fortuitum, M. kansasii, M. leprae, M. malmoense, M. marinum, M. paratuberculosis, M. scrofulaceum, M. simiae, M. szulgai, M. ulcerans, M. xenopi, Mycoplasma, Neisseria gonorrhoeae, N. meningitides, Nocardia asteroides, N. brasiliensis, N. otitidiscaviarum, N. transvalensis, Proteus mirabilis, P. vulgaris, Rhodococcus equi, Salmonella* including *S. arizonae, S. cholerasuis, S. enteritidis, S. gallinarum-pullorum, S. meleagridis, S. paratyphi,* A, B, C, *S. typhi, S. typhimurium, Shigella* including *S. boydii, S. dysenteriae,* type 1, *S. flexneri, S. sonnei, Sphaerophorus necrophorus, Staphylococcus aureus, Streptobacillus moniliformis, Streptococcus* including *S. pneumoniae, S. pyogenes, Treponema pallidum, T. carateum, Vibrio cholerae, V. parahemolyticus, V. vulnificus, Yersinia enterocolitica, Bartonella, Brucella* including *B. abortus, B. canis, B. suis, B. melitensis, Burkholderia (Pseudomonas) mallei, B. pseudomallei, Coxiella burnetii, Francisella tularensis, Mycobacterium bovis* (except BCG strain, BSL II—Bacterial Agents Including *Chlamydia*), *M. tuberculosis,* Mycobacteria other than tuberculosis (MOTT), *Pasteurella multocida* type B—"buffalo" and other virulent strains. *Rickettsia akari, R. australis, R. canada, R. conorii, R. prowazekii, R. rickettsii, R, siberica, R. tsutsugamushi, R. typhi (R. mooseri), Yersinia pestis.*

The analyte can be derived from a viral pathogen. For example, in some embodiments, the analyte is derived from a viral pathogen selected from among Adenoviruses, human—all types, Alphaviruses (Togaviruses), Eastern equine encephalitis virus, Eastern equine encephalomyelitis virus, Venezuelan equine encephalomyelitis vaccine strain TC-83, Western equine encephalomyelitis virus, Arenaviruses, Lymphocytic choriomeningitis virus (non-neurotropic strains), Tacaribe virus complex, Bunyaviruses, Bunyamwera virus, Rift Valley fever virus vaccine strain MP-12, Calciviruses, Coronaviruses. Flaviviruses (Togaviruses)— Group B Arboviruses, Dengue virus serotypes 1, 2, 3, and 4, Yellow fever virus vaccine strain 17D, Hepatitis A, B, C, D, and E viruses, the Cytomegalovirus, Epstein Barr virus, Herpes simplex types 1 and 2, Herpes zoster, Human herpesvirus types 6 and 7, Influenza viruses types A, B, and C, Papovaviruses, Papilloma viruses, Newcastle disease virus, Measles virus, Mumps virus, Parainfluenza viruses types 1, 2, 3, and 4, polyomaviruses (JC virus, BK virus), Respiratory syncytial virus, Human parvovirus (B 19), Coxsackie viruses types A and B, Echoviruses, Polioviruses, Rhinoviruses, Alastrim (*Variola minor* virus), Smallpox (*Variola major* virus), Whitepox Reoviruses, Coltivirus, human Rotavirus, and Orbivirus (Colorado tick fever virus), Rabies virus, Vesicular stomatitis virus, Rubivirus (rubella), Semliki Forest virus, St. Louis encephalitis virus, Venezuelan equine encephalitis virus, Venezuelan equine encephalomyelitis virus, Arenaviruses (a.k.a. South American Haemorrhagic Fever virus), Flexal, Lymphocytic choriomeningitis virus (LCM) (neurotropic strains), Hantaviruses including Hantaan virus, Rift Valley fever virus, Japanese encephalitis virus, Yellow fever virus, Monkeypox virus, Human immunodeficiency virus (HIV) types 1 and 2, Human T cell lymphotropic virus (HTLV) types 1 and 2, Simian immunodeficiency virus (SIV), Vesicular stomatitis virus, Guanarito virus, Lassa fever virus, Junin virus, Machupo virus, Sabia, Crimean-Congo hemorrhagic fever virus, Ebola viruses, Marburg virus, Tick-borne encephalitis virus complex (flavi) including Central European tick-borne encephalitis, Far Eastern tick-borne encephalitis, Hanzalova, Hypr, Kumlinge, Kyasanur Forest disease, Omsk hemorrhagic fever, and Russian Spring Summer encephalitis viruses, Herpesvirus simiae (Herpes B or Monkey B virus), Cercopithecine herpesvirus 1 (Herpes B virus), Equine morbillivirus (Hendra and Hendra-like viruses), Nipah virus, *Variola major* virus (Smallpox virus), *Variola minor* virus (Alastrim), African swine fever virus, African horse sickness virus, Akabane virus, Avian influenza virus (highly pathogenic), Blue tongue virus, Camel pox virus, Classical swine fever virus, Cowdria ruminantium (heartwater), Foot and mouth disease virus, Goat pox virus, Japanese encephalitis virus, Lumpy skin disease virus, Malignant catarrhal fever virus, Menangle virus, Newcastle disease virus (VVND), Peste Des Petits Ruminants virus, Rinderpest virus, Sheep pox virus, Swine vesicular disease virus, Vesicular stomatitis virus (exotic).

The analyte can be derived from a parasite. For example, in some embodiments, the analyte is derived from a parasite selected from among *Ancylostoma* human hookworms including *A. duodenale, A. ceylanicum, Ascaris* including *Ascaris lumbricoides suum, Babesia* including *B. divergens, B. microti, Brugia filaria* worms including *B. malayi, B. timori, Coccidia, Cryptosporidium* including *C. parvum, Cysticercus cellulosae* (hydatid cyst, larva of *T. solium*), *Echinococcus* including *E. granulosis, E. multilocularis, E. vogeli, Entamoeba histolytica, Enterobius, Fasciola* including *F. gigantica, F. hepatica, Giardia* including *G. lamblia, Heterophyes, Hymenolepis* including *H. diminuta, H. nana, Isospora, Leishmania* including *L. braziliensis, L. donovani, L. ethiopia, L. major, L. mexicana, L. peruvania, L. tropica, Loa loa filaria* worms, *Microsporidium, Naegleria fowleri, Necator* human hookworms including *N. americanus, Onchocerca filaria* worms including, *O. volvulus, Plasmodium cynomologi, P. falciparum, P. malariae, P. ovale, P. vivax, Sarcocystis* including *S. sui hominis, Schistosoma* including *S. haematobium, S. intercalatum, S. japonicum, S. mansoni, S. mekongi, Strongyloides* including *S. stercoralis, Taenia solium, Toxocara* including *T. canis, Toxoplasma* including *T. gondii, Trichinella spiralis, Trypanosoma* including *T. brucei brucei*, *T. brucei gambiense*, *T. brucei rhodesiense*, *T. cruzi*, or *Wuchereria bancrofti filaria* worms.

The analyte can be a fungal pathogen. For example, in some embodiments, the analyte is derived from a fungal pathogen selected from among *Aspergillus fumigates*, *Blastomyces dermatitidis*, *Cladosporium bantianum*, *Candida albicans*, *C. (Xylohypha) trichoides*, *Cryptococcus neoformans*, *Dactylaria galopava* (*Ochroconis gallopavum*), *Epidermophyton*, *Exophiala* (*Wangiella*) *dermatitidis*, *Fonsecaea pedrosoi*, *Microsporum*, *Paracoccidioides braziliensis*, *Penicillium marneffei*, *Pneumocystis carinii*, *Sporothrix schenckii*, *Trichophyton*, *Coccidioides immitis*, *Coccidioides posadasii*, *Histoplasma capsulatum*, *H. capsulatum* var. *duboisii*.

The analyte can be a toxin. In some embodiments, the analyte is a toxin selected from among Abrin, *Botulinum* neurotoxins, *Clostridium perfringens* epsilon toxin, Conotoxins, Diacetoxyscirpenol, Ricin, Saxitoxin, Shiga-like ribosome inactivating proteins, Shigatoxin, Staphylococcal enterotoxins, T-2 toxin, and tetrodotoxin.

In some embodiments, the analyte is selected from among Hepatitis B surface antigen (HBsAg), *B. burgdorferi* OspA, HPV L1, RSV F protein, Influenza hamagglutanin, Influenza stem-loop region, Influenza M2, *P. falciparum* merozoite surface protein 1-10, GLURP, SERA, S-antigen, 6-cys family, AMA1, EBA175, 140, 181, MTRAP, PTRAMP, ASP, Rh1, 2a, 2b, 4, 5, RAP1, 2, 3, RAMA, RHOPH1, 2, 3, *P. vivax* circumsporozoite protein, sporozoite surface proetin2, SSP2/TRAP, CSP-N, CSP-R, CSP-C, MSP-1, MSP-9, DBPRIII, AMA-1, Pvs25, Pvs28, *S. aureus* capsular polysaccharide, poly-N-acetyl glucosamine, HIV gp120, gp41, and Dengue virus conserved regions.

In another embodiment the analyte comprises at least one epitope of an allergen. Allergens can be naturally occurring, or artificial such as allergens contained in allergy vaccines. Examples of allergens include, but are not limited to, animal products (for example, Fel d 1, fur dander, cockroach calyx, wool, dust mite excretion), drugs (for example, penicillin, sulfonamides, salicylates, local anaesthetic), food (for example, celery and celeriac, corn, eggs (e.g., albumin), fruit, legumes (for example, beans, peas, peanuts, soybeans), milk, seafood (e.g., shellfish), sesame, soy, tree nuts (for example, pecans, almonds), wheat, insect venom (for example, fire ants, bee sting venom, wasp sting venom), latex, metal, plant pollen (for example, grass (e.g., ryegrass, timothy-grass, weeds (e.g., ragweed, plantago, nettle, *Artemisia vulgaris*, *chenopodium album*, sorrel), and trees (e.g., birch, alder, hazel, hornbeam, aesculus, willow, poplar, platanus, tilia, olea, Ashe juniper).

In some embodiments, the analyte is an allergen derived from a latex protein, for example, unprocessed latex sap, raw latex containing ammonia, or finished latex product in which the proteins have been exposed to chemicals and high temperatures. In some embodiments, the allergen is the allergen of a mite, for example, *Dermatophagoides farinae*, *Dermatophagoides pteronyssinus*, *Acarus siro*, *Blomia tropicalis*, *Chortoglyphus arcuatas*, *Euroglyphus cannei*, *Lepidoglyphus destructor*, *Tyrophagus putrescentiae*, or *Glyphagus demesticus*. In some embodiments, the allergen is from venom, for example, *Bombus* spp., *Vespa crabro*, *Apis mellifera*, *Dolichovespula* spp., *Polistes* spp., *Vespula* spp., *Dolichovespula maculata*, or *Dolichovespula arenaria*. In some embodiments, the analyte is an allergen from an insect, for example, *Camponotus pennsylvanicus*, *Solenopsis invicta*, *Solenopsis richteri*, *Periplaneta americana*, *Blattella germanica*, *Blatta orientails*, *Tebanus* spp., *Musca domestica*, *Ephemeroptera* spp., *Culicidae* sp., or *Heterocera* spp.

In some embodiments, the allergen analyte is epithelia, dander, or hair from an organism, for example, *Serinus canaria*, *Felis catus* (*domesticus*), *Bos taurus*, *Gallus gallus* (*domesticus*), *Canis familiaris*, *Arias platyrhynchos*, *Meriones unguiculatus*, *Capra hircus*, *Anser domesticus*, *Cavia porcellus* (*cobaya*), *Mesocrietus auratus*, *Sus scrofa*, *Equus caballus*, *Mus musculus*, *Psittacidae*, *Columba fasciata*, *Oryctolagus cuniculus*, *Rattus norvegicus*, or *Ovis aries*.

In some embodiments, the allergen analyteis from fungi, for example, *Cephalosporium acremonium*, *Alternaria tenuis*, *Aspergillus glaucus*, *Aspergillus flavus*, *Aspergillus fumigatus*, *Aspergillus nidulans*, *Aspergillus niger*, *Aspergillus terreus*, *Aspergillus versicolor*, *Aureobasidium pullulan* (*Pullularia pullulans*), *Drechslera sorokiniana*, *Helminthosporium sativum*, *Botrytis cinerea*, *Candida albicans*, *Chaetomium globosum*, *Cladosporium herbarum*, *Cladosporium sphaerospennum* (*Homodendrum hordei*), *Drechslera spicifera* (*Curvularia spicifera*), *Epicoccum nigrum* (*Epicoccum purpurascens*), *Epidermophyton floccosum*, *Fusarium moniliforme*, *Fusarium solani*, *Geotrichum candidum*, *Gliocladium viride*, *Helminthosporium solani*, *Microsporum canis*, *Mucor circinelloidesf circinelloides*, *Mucor circinelloidesf lusitanicus*, *Mucor plumbous*, *Mycogone perniciosa*, *Neurospora intermedia*, *Nigrospora oryzae*, *Paecilomyces variotii*, *Penicillum brevicompactum*, *Penicillum camembertii*, *Penicillum chrysogenum*, *Penicillum digitatum*, *Penicillum expansum*, *Penicillum notatum*, *Penicillum roquefortii*, *Phoma betae*, *Phoma herbarum*, *Rhizopus oryzae*, *Rhizopus stolonifer*, *Rhodotorula mucilaginosa*, *Saccharomyces cerevisiae*, *Scopulariopsis brevicaulis*, *Serpula lacrymans*, *Setosphaeria rostrata*, *Stemphylium botryosum*, *Stemphylium solani*, *Trichoderma harzianum*, *Trichophyton mentagrophytes*, *Trichophyton rubrum*, or *Trichothecium roseum*. In some embodiments, the allergen is from a smut, for example, *Ustilago nuda*, *Ustilago cynodontis*, *Ustilago candis*, *Sporisorium cruentum*, *Ustilago avenae*, or *Ustilago tritici*.

In some embodiments, the allergen analyte is from a grass, for example, *Paspalum notatum*, *Cynodon dactylon*, *Poa compressa*, *Bromus inennis*, *Phalaris arundinacea*, *Zea cans*, *Elytrigia repens* (*Agropyron repens*), *Sorghum haelpense*, *Poa pratensis*, *Festuca pratensis* (*elatior*), *Avena sativa*, *Dactylis glomerata*, *Agrostis gigantea* (*alba*), *Secale cereale*, *Leymus* (*Elymus*) *condensatus*, *Lolium perenne* ssp. *multiflorum*, *Lolium perenne*, *Anthoxanthum odoratum*, *Phleum pratense*, *Holcus lanatus*, *Triticum aestivum*, or *Elymus* (*Agropyron*) *smithii*.

In some embodiments, the allergen analyte is from a weed, for example, *Atriplex polycarpa*, *Baccharis halimifolia*, *Baccharis sarothroides*, *Hymenoclea salsola*, *Amaranthus hybridus*, *Xanthium strumarium* (*commune*), *Rumex crispus*, *Eupathium capillifolium*, *Solidago* spp., *Amaranthus tuberculatus* (*Acnida tamariscina*), *Allenrolfea occidentalis*, *Chenopodium botrys*, *Kochia scoparia*, *Chenopodium album*, *Iva xanthifolia*, *Iva angustifolia*, *Chenopodium ambrosioides*, *Artemisia vulgaris*, *Artemisia ludoviciana*, *Urtica dioica*, *Amaranthus spinosus*, *Plantago lanceolata*, *Iva axillaris*, *Atriplex lentiformis*, *Ambrosia dumosa*, *Ambrosia acanthicarpa*, *Ambrosia trifida*, *Ambrosia artemisiifolia*, *Ambrosia confertiflora*, *Ambrosia bidentata*, *Ambrosia psilostachya*, *Salsola kali* (*pestifer*), *Artemisia californica*, *Artemisiafrigida*, *Artemisia tridentata*, *Atriplex wrightii*, *Atriplex confertifolia*, or *Artemisia annua*.

In some embodiments, the allergen analyte is from a tree, for example, *Acasia* spp., *Alnus glutinosa, Alnus rubra, Alnus incana* ssp. *rugosa, Alnus rhombifolia, Fraxinus velutina, Fraxinus pennsylvanica, Fraxinus latifolia, Fraxinus americana, Populus tremuloides, Myrica cerifera, Fagus grandifolia (americana), Casuarina equisetifolia, Betula lenta, Betula pendula, Betula nigra, Betula occudentalis (fontinalis), Betula populifolia, Acer negundo, Cryptomeria japonica, Juniperus ashei (sabinoides), Juniperus virginiana, Tamarix gallica, Populus balsamifera* ssp. *trichocarpa, Populus deltoides, Populusfremontii, Populus wislizeni, Populus monilifera (sargentii), Cupressus arizonoca, Taxodium distichum, Cupressus sempervirens, Ulmus americana, Ulmus crassifolia, Ulmus pumila, Eucalyptus globulus, Celtis occidentalis, Corylus americana, Corylus avellana, Carya ovata, Carya laciniosa, Carya alba, Juniferus monosperma, Juniperus princhotii, Juniperus scopulorum, Juniperus occidentalis, Robinia pseudoacacia, Mangifera indica, Acer macrophyllum, Acer rubrum, Acer saccharum, Melaleuca quinquenervia (leucadendron), Prosopis glandulosa (juliflora), Broussonetia papyrifera, Morus rubra, Morums alba, Quercus gambelii, Quercus velutina, Quercus macrocarpa, Quercus kelloggii, Quercus agrifolia, Quercus lobata, Quercus ilex, Quercus stellata, Quercus rubra, Quercus dumosa, Quercus virginiana, Quercus nigra, Quercus garryana, Quercus alba, Olea europaea, Elaegnus angustifolia, Citrus sinensis, Arecastrum romanzoffianum (Cocos plumosa), Carya illnoensis, Schinus molle, Schinus terebinthifolius, Pinus taeda, Pinus strobus, Pinus palustris, Pinus ponderosa, Pinus elliottii, Pinus virginiana, Pinus monticola, Pinus echinata, Populus nigra, Populus alba, Ligustrum vulgare, Liquidambar styraciflua, Platanus occidentalis, Platanus orientalis, Platanus racemosa, Platanus acerifolia, Juglans nigra, Juglans californica, Juglans regia, Salix lasiolepsis, Salix nigra,* or *Salix discolor*. In some embodiments, the allergen is from a flower, for example, *Chrysanthemum leucanthemum, Taraxacum officinale,* or *Helianthus annuus*. In some embodiments, the allergen is from a farm plant, for example, *Medicago sativa, Ricinus communis, Trifolium pratense, Brassica* spp., or *Beta vulgaris*.

In some embodiments, the allergen analyte is from plant food (an edible plant), for example, *Prunus dulcis, Malus pumila, Prunus armeniaca, Musa paradisiaca (sapientum), Hordeum vulgare, Phaseolus lanatus, Phaseolus vulgaris, Phaseolus* sp., *Phaseolus* sp., *Phaseolus vulgaris, Rubus allegheniensis, Vaccinium* sp., *Brassica oleracea* var. *botrytis, Fagopyrum esculentum, Brassica oleracea* var. *capitata, Theobroma cacao, Cucumis melo, Daucus carota, Brassica oleracea* var. *botrytis, Apium graveolens* var. *dulce, Prunus* sp., *Cinnamomum verum, Coffea arabic, Zea cans, Vaccinium macrocarpon, Cucumis sativus, Allium sativum, Zingiber officinale, Vitis* sp., *Citrus paradisi, Humulus lupulus, Citrus limon, Lactuca sativa, Agaricus campestris, Brassica* sp., *Myristica fragrans, Avena sativa, Olea europaea, Allium cepa* var. *cepa, Citrus sinensis, Vigna unguiculata, Pisum sativum, Prunus persica, Pyrus communis, Piper nigrum, Capsicum annuum* var. *annuum, Ananas comosus, Ipomoea batatas, Solanum tuberosum, Rubus idaeus* var. *idaeus, Oryza sativa, Secale cereale, Sesamum orientale (indicum), Glycine max, Spinacia oleracea, Cucurbita pepo* var. *melopepo, Fragaria chiloensis, Lycopersicon esculentum (lycopersicum), Brassica rapa* var. *rapa, Vanilla planifolia, Citrullus lanatus* var. *lanatus,* or *Triticun aestivum*.

In some embodiments the allergen analyte is from fish or shellfish, for example, *Micropterus* sp., *Ictalurus punctatus, Mercenaria mercenaria, Gadus morhua, Callinectes sapidus, Platichthys* sp., *Hippoglossus* sp., *Homarus americanus, Scomber scombrus, Crassostrea virginica, Sebastes marinus, Salmo salar, Clupeiformes, Pecten magellanicus, Penaeus* sp., *Salvelinus* sp., or *Thunnus* sp. In some embodiments, the allergen is an animal food product, for example, from *Bos taurus, Ovis aries,* or *Sus scrofa*. In some embodiments, the allergen is a poultry product, for example, chicken (*Gallus gallus*) products or turkey (*Meleagris gallopavo*) products. In some embodiments, the allergen is from a dairy product, for example, bovine casein or bovine milk. In some embodiments, the allergen is a nut, for example, *Bertholletia excelsa, Anacardium oceidentale, Cocos nucifera, Corylus americana, Arachis hypogaea, Carya illinoensis, Juglans nigra,* or *Juglans regia*. In some embodiments, the allergen is dust, for example, barley grain dust, corn grain dust, house dust, mattress dust, oat grain dust, wheat grain dust, upholstery dust, or latex dust.

In some embodiments, the antigen analyte is an autoantigen associated with an autoimmune disorder. In some embodiments, the autoimmune disorder is a cell or organ-specific autoimmune disorder, and the autoantigen analyte is selected from among: acetylcholine receptor (myasthenia gravis), actin (chronic active hepatitis, primary biliary cirrhosis), adenine nucleotide translocator (ANT) (dilated cardiomyoapthy, myocarditis), beta-adrenoreceptor (dilated .degree. cardiomyopathy), aromatic L-amino acid decarboxylase (autoimmune polyendocrine syndrome type I (APS-1)), asialoglycoprotein receptor (autoimmune hepatitis), bactericidal/permeability-increasing protein (Bpi) (cystic fibrosis vasculitides), calcium-sensing receptor (acquired hypoparathyroidism), cholesterol side-chain cleavage enzyme (CYPIIa) (APS-1), collagen type IV alpha3-chain (Goodpasture syndrome), cytochrome P450 2D6 (CYP2D6) (autoimmune hepatitis), desmin (Crohn disease, coronary artery disease), desmoglein 1 (pemphigus foliaceus), desmoglein 3 (pemphigus vulgaris), F-actin (autoimmune hepatitis), GM ganglioside (Guillain-Barre syndrome), glutamate decarboxylase (GAD65) (type 1 diabetes, stiff man syndrome), glutamate receptor (GLUR) (Rasmussen encephalitis), H/K ATPase (autoimmune gastritis), 17-alpha-hydroxylase (CYP17) (APS-1), 21-hydroxylase (CYP21) (Addison disease), IA-2 (ICA512) (type 1 diabetes), insulin (type 1 diabetes, insulin hypoglycemic syndrome (Hirata disease), type B insulin resistance, acanthosis, systemic lupus erythematosus (SLE)), intrinsic factor type 1 (pernicious anemia), leukocyte function-associated antigen (LFA-1) (treatment-resistant lyme arthritis), myelin-associated glycoprotein (MAG) (polyneuropathy), myelin basic protein (multiple sclerosis, demyelinating disease), myelin oligodendrocyte glycoprotein (MOG) (multiple sclerosis), myosin (rheumatic fever), p-80-Coilin (atopic dermatitis), pyruvae dehydrogenase complex-E2 (PDC E2) (primary biliary cirrhosis), sodium iodide symporter (NIS) (Graves disease, autoimmune hypothyroidism), SOX-10 (vitiligo), thyroid and eye muscle shared protein (autoimmune thyroiditis), thyroid peroxidase (autoimmune Hashimoto thyroiditis), thyrotropin receptor (Graves disease), tissue transglutaminase (celiac disease), transcription coactivator p75 (atopic dermatitis), tryptophan hydroxylase (APS-1), tyroisinase (vitiligo, metastatic melanoma), and tyrosine hydroxylase (APS-1), wherein the associated autoimmune disorder(s) is listed parenthetically immediately after each autoantigen analyte.

In some embodiments, the autoimmune disorder is a systemic autoimmune disorder, and the autoantigen analyte is selected from among: ACTH (ACTH deficiency), aminoacyl-tRNA histidyl synthetase (myositis, dermatomyositis), aminoacyl-tRNA synthetase (polymyositis, dermatomyositis), cardiolipin (SLE), carbonic anhydrase II (SLE, Sjogren syndrome, systemic sclerosis), collagen (rheumatoid arthritis (RA), SLE, progressive systemic sclerosis), centromere-associated protein (systemic sclerosis), DNA-dependent nucleosome-stimulated ATPase (dermatomyositis), fibrillarin (scleroderma), fibronectin (SLE, RA, morphea), glucose-6-phosphate isomerase (RA), Beta2-glycoprotein I (Beta2-GPI) (primary antiphospholipid syndrome), golgin (95, 97, 160, and/or 180) (Sjogren syndrome, SLE, RA), heat shock protein (various immune related disorders), hemidesmosomal protein 180 (bullous pemphigoid, herpes gestationis, cicatricial pemphigoid, histone H2A-H2B-DNA (SLE), IgE receptor (chronic idiopathic urticaria), keratin (RA), Ku-DNA-protein kinase (SLE), Ku-nucleoprotein (connective tissue syndromes), La phosphoprotein (La 55-B) (Sjoren syndrome), myeloperoxidase (necrotizing and cescentic glomerulonephritis (NCGN), system vasculitis), proteinase 3 (PR3) (Wegener granulomatosis, Churg-Strauss syndrome), RNA polymerase I-III (RNP) (systemic sclerosis, SLE), signal recognition protein (SRP54) (polymyositis), topoisomerase-1 (Scl-70) (scleroderma, Raynaud syndrome), tubulin (chronic liver disease, visceral leishmaniasis), and vimentin (systemic autoimmune disease), wherein the associated autoimmune disorder(s) is listed parenthetically immediately after each autoantigen.

In some embodiments, the autoimmune disorder is a plasma protein autoimmune disorder or cytokine autoimmune disorder, and the autoantigen analyte is selected from among: C1 inhibitor (autoimmune C1 deficiency), C1q (SLE, membrane proliferative glomerulonephritis (MPGN)), cytokine (e.g., IL-1 alpha, IL-1beta, IL-, IL-10, LIF) (RA, systemic sclerosis), factor II (prolonged coagulation time), factor V (prolonged coagulation time), factor VII (prolonged coagulation time), factor VIII (prolonged coagulation time), factor IX (prolonged coagulation time), factor X (prolonged coagulation time), factor XI (prolonged coagulation time), factor XII (prolonged coagulation time), thrombin (prolonged coagulation time), vWF (prolonged coagulation time), glycoprotein IIb/IIIg and Ib/IX (autoimmune thrombocytopenia purpura), IgA (immunodeficiency), and oxidized LDL (OxLDL) (atherosclerosis), wherein the associated autoimmune disorder(s) is listed parenthetically immediately after each autoantigen analyte.

In some embodiments, the autoimmune disorder is a cancer or paraneoplastic autoimmune disorder, and the autoantigen analyte is selected from among: amphiphysin (neuropathy, small lung cell cancer), cyclin B 1 (hepatocellular carcinoma), DNA topoisomerase II (liver cancer), desmoplakin (paraneoplastic pemphigus), gephyrin (paraneoplastic stiff man syndrome), Hu protein (paraneoplastic encephalomyelitis), neuronal nicotinic acetylcholine receptor (subacute autonomic neuropathy, cancer), p53 (cancer, SLE), p62 (IGF-II mRNA-binding protein) (hepatocellular carcinoma), recoverin (cancer-associated retinopathy), R1 protein (paraneoplastic opsoclonus myoclonus ataxia), beta IV spectrin (lower motor neuron syndrome), synaptotagmin (Lambert-Eaton myasthenic syndrome), voltage-gated calcium channels (Lambert-Eaton myasthenic syndrome) and Yo protein (paraneoplastic cerebellar degeneration).

In some embodiments, the antigen analyte is an endogenous antigen that is an aberrantly expressed polypeptide. Examples of such endogenous antigens include, but are not limited to, amyloid beta (A-beta or A.beta.), alpha synuclein, cystatin C, tau, ABri, ADan, superoxide dismutase (SOD), mutant Huntington, PrP.sup.sc or a fragment of any of the foregoing.

In some embodiments of the invention, the analyte comprises at least one epitope of an implant to be introduced into a subject, metabolic or degradation products of an implant material, or substances that specifically bind to an epitope of an implant material, such as antibodies developed to an implant material or its degradation products Such implants can include, for example, electrically powered implants (for example, artificial pacemakers), bioimplants (biomaterial surgically implanted in a subject's body to replace damaged tissue (for example, orthopedic reconstructive prosthesis), cardiac prostheses (artificial valves), skin, and cornea), contraceptive implants, dental implants, orthopedic implants, and adhesion prevention devices. Examples of implant materials that can bear epitopes include latex; silicone; metals, such as cobalt chrome (Co—Cr) alloys, titanium, and titanium alloys; polymers, such as ultra-high molecular weight polyethylene (UHMWPE) and polymethyl methacrylate cement (PMMA); and bioceramics, such as hydroxyapatite and Bioglass.

Non-Antibody Signal Transducing Element

Exemplary embodiments of the present invention include various non-antibody signal transducing elements. Each signal transducing element is adapted to receive, i.e., bind, a detector molecule that is itself adapted to receive, i.e., bind, a specific analyte of interest. In one embodiment, the signal transducing element is a transmembrane chimeric fusion protein that is engineered into and expressed on the surface of the biosensor cell, and that is adapted to activate the signal transduction pathway that ultimately results in the reporter protein emitting a detectable signal. In another embodiment, the signal transducing element is a soluble chimeric fusion protein that is adapted to bind to a cell surface signal transducer, such as a native receptor or receptor protein that is adapted to activate the signal transduction pathway that ultimately results in the reporter protein emitting a detectable signal. In still another embodiment, the signal transducing element is a soluble chimeric fusion protein that is engineered into and expressed by the biosensor cell. The soluble chimeric fusion protein is then secreted/excreted into the extracellular space where it binds to a cell surface signal transducer, such as a native receptor or receptor protein that is adapted to activate the signal transduction pathway that ultimately results in the reporter protein emitting a detectable signal.

The chimeric fusion proteins of this invention may include: (i) a component of a protein that is adapted to bind to the at least one type of detector molecule (e.g., a soluble antibody); and (ii) a component of a receptor complex normally expressed by the living, engineered biosensor cell. In some embodiments, the component of the protein that is adapted to bind to the at least one type of detector molecule may be derived from a bacterial binding protein (i.e., an antibody binding protein derived from a bacteria) such as, for example, the IgG binding domain of a strep G protein (referred to herein as IgGbp or Igbp in the Figures). Tandem repeats of this IgG binding domain may be included to increase the affinity of the binding protein for the soluble antibody. In an alternate embodiment, the component of the chimeric fusion protein that is adapted to bind to the at least one type of detector molecule is an antibody binding domain derived from a receptor protein such as, for example, the murine Fc gamma RI (FcγRI) receptor. In various exemplary embodiments, the component of the receptor complex normally expressed by the living, engineered biosensor cell is IgM (for B cell biosensors); Igα/β (for B cell biosensors);

IgE (for mast cell biosensors); CD19 (for B cell biosensors), CD3zeta (for T cell biosensors), or FcεRI (for mast cell biosensors).

The non-antibody signal transducing elements of this invention may include either complete protein sequences or engineered protein fragments such as selected protein domains derived from larger protein molecules. One of ordinary skill in the art will appreciate that fragments of larger molecules may be created using standard genetic engineering techniques such as synthetic gene technology. When fragments of larger proteins are used to engineer antibody binding motifs as aspects of chimeric fusion proteins it is important to design the engineered proteins to ensure proper conformational folding of the selected protein fragments. Therefore, it is useful to include (in the fusion proteins) short spacer or linker elements that do not readily form protein secondary structures. Short combinations of amino acids such as glycine, serine and alanine, for example, may be used for these spacer or linker elements. In an exemplary embodiment, the amino acid sequence glycine (G), serine (S), alanine (A), serine (S), glycine (G), serine (S), glycine (G) is used to separate a binding domain from a component of a receptor complex in an engineered protein molecule (see SEQ ID NO: 19). With regard to the peptide linker or spacer used to connect the detector element to the signal-transducing element or interconnect different segments of a signal-transducing element: the linker typically joins the carboxyl terminus of one element to the amino terminus of another. Peptide linkers may vary from 0 to 25 amino acids in length or any intermediate integer value and typically, but not always, comprise hydrophilic amino acids such as glycine (G) and serine (S).

As previously stated, each signal transducing element binds to a detector molecule that binds to a specific analyte of interest. A detector molecule that has bound to an analyte will either (i) bind to a transmembrane signal transducing element; or (ii) to a signal transducing element that will itself bind to a cell surface signal transducer (e.g., native receptor). In the first situation, upon the binding of a sufficient number of analytes to a sufficient number of detector molecules that are themselves bound to transmembrane non-antibody signal transducing elements, an aggregation of signal transducing elements occurs on the biosensor cell surface, the signal transduction pathway is activated, the biological process occurs, and the detectable signal is emitted by the reporter protein. In the second case, upon the binding of a sufficient number of analytes to a sufficient number of detector molecules to a sufficient number of non-antibody signal transducing elements that are themselves bound to the appropriate native receptor, an aggregation of the receptors occurs on the cell surface, the signal transduction pathway is activated, the increase in intracellular calcium occurs, and detectable light is emitted by the reporter protein.

A first non-antibody signal transducing element in accordance with an exemplary embodiment of the present invention includes a bacterial binding protein (IgGbp) fused to the IgM heavy chain constant domain (B cell) with a GSASGSG linker. SEQ ID NO: 1 provides the DNA sequence for signal transducing element IgGbp-IgM and SEQ ID NO: 2 provides the protein sequence for signal transducing element IgGbp-IgM.

A second non-antibody signal transducing element in accordance with an exemplary embodiment of the present invention includes a bacterial binding protein (IgGbp) fused to the Igα/β component of the B cell receptor with a GSASGSG linker. SEQ ID NO: 3 provides the DNA sequence for signal transducing element IgGbp-Igα/β and SEQ ID NO: 4 provides the protein sequence for signal transducing element IgGbp-Igα/β.

A third non-antibody signal transducing element in accordance with an exemplary embodiment of the present invention includes a bacterial binding protein (IgGbp) fused to the CD3 zeta chain of the T-cell receptor with a GSASGSG linker. SEQ ID NO: 5 provides the DNA sequence for signal transducing element IgGbp-CD3ζ and SEQ ID NO: 6 provides the protein sequence for signal transducing element IgGbp-CD3ζ.

A fourth non-antibody signal transducing element in accordance with an exemplary embodiment of the present invention includes the FcγRI antibody binding domain fused to the IgM heavy chain constant domain (B cell) with a GSASGSG linker. SEQ ID NO: 7 provides the DNA sequence for signal transducing element FcγRI-IgM and SEQ ID NO: 8 provides the protein sequence for signal transducing element FcγRI-IgM.

A fifth non-antibody signal transducing element in accordance with an exemplary embodiment of the present invention includes the FcγRI antibody binding domain fused to the Igα/β component of the B-cell receptor with a GSASGSG linker. SEQ ID NO: 9 provides the DNA sequence for signal transducing element FcγRI-Igα/β and SEQ ID NO: 10 provides the protein sequence for signal transducing element FcγRI-Igα/β.

A sixth non-antibody signal transducing element in accordance with an exemplary embodiment of the present invention includes the FcγRI antibody binding domain fused to the CD3 zeta chain of the T-cell receptor with a GSASGSG linker. SEQ ID NO: 11 provides the DNA sequence for signal transducing element FcγRI-CD3ζ and SEQ ID NO: 12 provides the protein sequence for signal transducing element FcγRI-CD3ζ.

A seventh exemplary non-antibody signal transducing element in accordance with the present invention includes a bacterial binding protein (IgGbp) fused to the IgE constant domain (B cell) with a GSASGSG linker. SEQ ID NO: 13 provides the DNA sequence for signal transducing element IgGbp-IgE and SEQ ID NO: 14 provides the protein sequence for signal transducing element IgGbp-IgE.

An eighth exemplary non-antibody signal transducing element in accordance with the present invention includes the FcγRI antibody binding domain fused to the IgE constant domain (B cell) with a GSASGSG linker. SEQ ID NO: 15 provides the DNA sequence for signal transducing element FcγRI-IgE and SEQ ID NO: 16 provides the protein sequence for signal transducing element FcγRI-IgE.

A ninth exemplary non-antibody signal transducing element in accordance with the present invention includes monomeric streptavidin fused to the CD3 zeta chain of the T-cell receptor with a GSASGSG linker. SEQ ID NO: 17 provides the DNA sequence for signal transducing element mSA-CD3ζ and SEQ ID NO: 18 provides the protein sequence for signal transducing element mSA-CD3ζ. Monomeric streptavidin is a recombinant form of streptavidin that includes mutations that break the streptavidin tetramer into a monomer and to enhance the solubility of the resultant isolated subunit.

Example Biosensor I

Figure 1B:
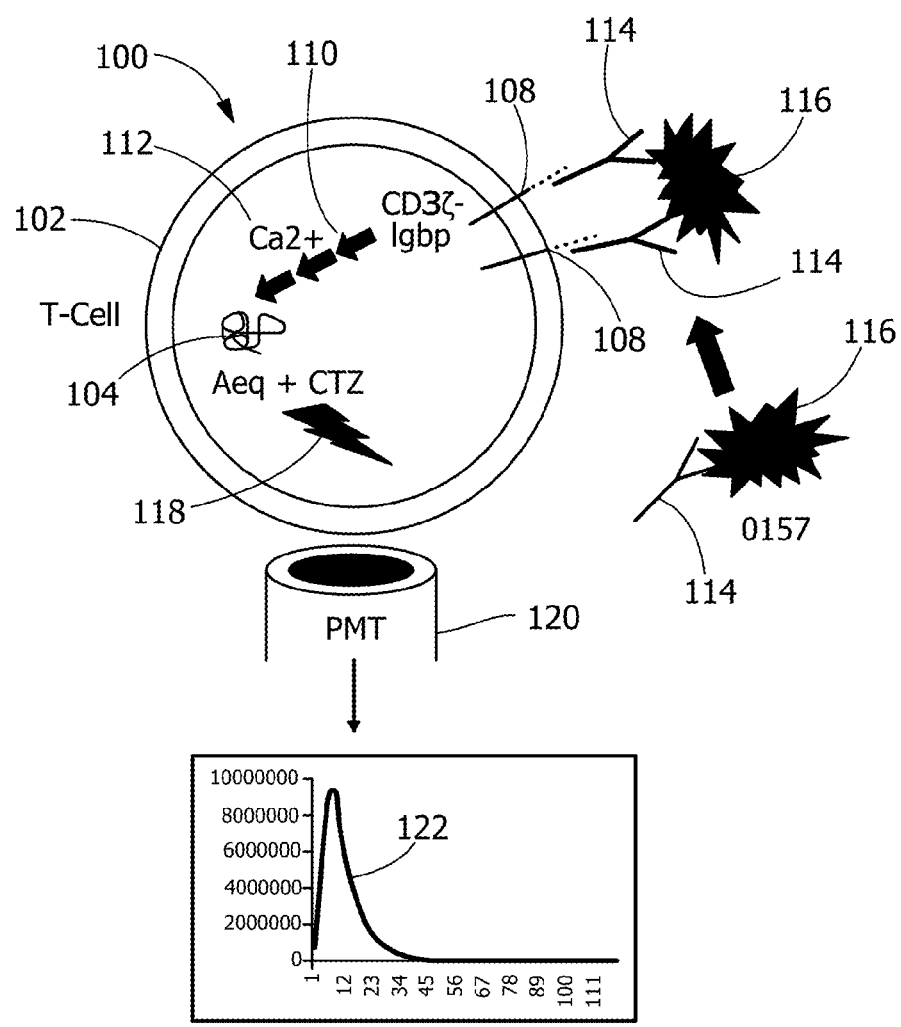

With reference to FIGS. 1a-b, a first biosensor 100 in accordance with an exemplary embodiment of the present invention includes Jurkat T cells 102 that have been engineered to produce aequorin 104 and that have been charged with CTZ 106 to form an aequorin/CTZ complex, as previously described. This particular biosensor has also been engineered to express the transmembrane non-antibody signal transducing element 108, which is IgGbp-CD3ζ (SEQ ID NOS: 5-6), although the transmembrane non-antibody signal transducing element FcγRI-CD3ζ (SEQ ID NO: 11-12) may also be used with biosensor 100. Biosensor cell 102 also includes at least one signal transduction pathway 110, the activation of which results in an increase of intracellular Ca2+ 112. As shown in FIG. 1b, when a sufficient number of detector molecules 114 (e.g., soluble antibodies) to which target analyte 116 (e.g., *E. coli* 0157) is bound bind to transmembrane non-antibody signal transducing elements 108, signal transduction pathway 110 is activated, intracellular Ca2+ 112 increases, the aequorin/CTZ complex undergoes a conformational change and emits a signal (photon) of light 118 which is detected by photo multiplier tube 120, and spike 122 is graphically displayed on a testing device (see description below), indicating the presence of target analyte 116 within a sample being tested. The display may be both qualitative and quantitative with regard to target analyte 116.

Example Biosensor II

With reference to FIGS. 2a-b, a second biosensor 200 in accordance with an exemplary embodiment of the present invention includes MC/9 (ATCC® CRL-8306™) mast cells 202 that have been engineered to produce aequorin 204 and that have been charged with CTZ 206 to form an aequorin/CTZ complex, as previously described. This particular biosensor expresses the native Fc epsilon receptor (i.e., FcεRI) 207, which binds to soluble non-antibody signal transducing element 208, which is IgGbp-IgE (SEQ ID NOS: 13-14), although the non-antibody signal transducing element FcγRI-IgE. (SEQ ID NO: 15-16) may also be used with biosensor 200. As shown in FIG. 2b, when a sufficient number of detector molecules 214 (e.g., soluble antibodies) to which target analyte 216 (e.g., *E. coli* 0157) is bound bind to non-antibody signal transducing elements 208 that have previously bound to native Fc epsilon receptors 207, signal transduction pathway 210 is activated, intracellular Ca2+ 212 increases, the aequorin/CTZ complex undergoes a conformational change and emits a signal (photon) of light 218 which is detected by photo multiplier tube 220, and spike 222 is graphically displayed on a testing device (see description below), indicating the presence of target analyte 216 within a sample being tested. The display may be both qualitative and quantitative with regard to target analyte 216.

Example Biosensor III

With reference to FIGS. 3a-b, a third biosensor 300 in accordance with an exemplary embodiment of the present invention includes MC/9 (ATCC® CRL-8306™) mast cells 302 that have been engineered to produce aequorin 304 and that have been charged with CTZ 306 to form an aequorin/CTZ complex, as previously described. This particular biosensor expresses the native Fc epsilon receptor (i.e., FcεRI) 307, which binds to non-antibody signal transducing element 308, which is IgGbp-IgE (SEQ ID NOS: 13-14), although the non-antibody signal transducing element FcγRI-IgE. (SEQ ID NO: 15-16) may also be used with biosensor 300. In this particular embodiment, biosensor cells 302 have been further engineered to express IgGbp-IgE and excrete this non-antibody signal transducing element into the extracellular space, wherein it binds to the native FcεRI expressed on the cell surface. As shown in FIG. 3b, when a sufficient number of detector molecules 314 (e.g., soluble antibodies) to which target analyte 316 (e.g., *E. coli* 0157) is bound bind to non-antibody signal transducing elements 308 that have previously bound to native Fc epsilon receptors 307, signal transduction pathway 310 is activated, intracellular Ca2+ 312 increases, the aequorin/CTZ complex undergoes a conformational change and emits a signal (photon) of light 318 which is detected by photo multiplier tube 320, and spike 322 is graphically displayed on a testing device (see description below), indicating the presence of target analyte 316 within a sample being tested. The display may be both qualitative and quantitative with regard to target analyte 316.

Example Biosensor IV

Figure 4:
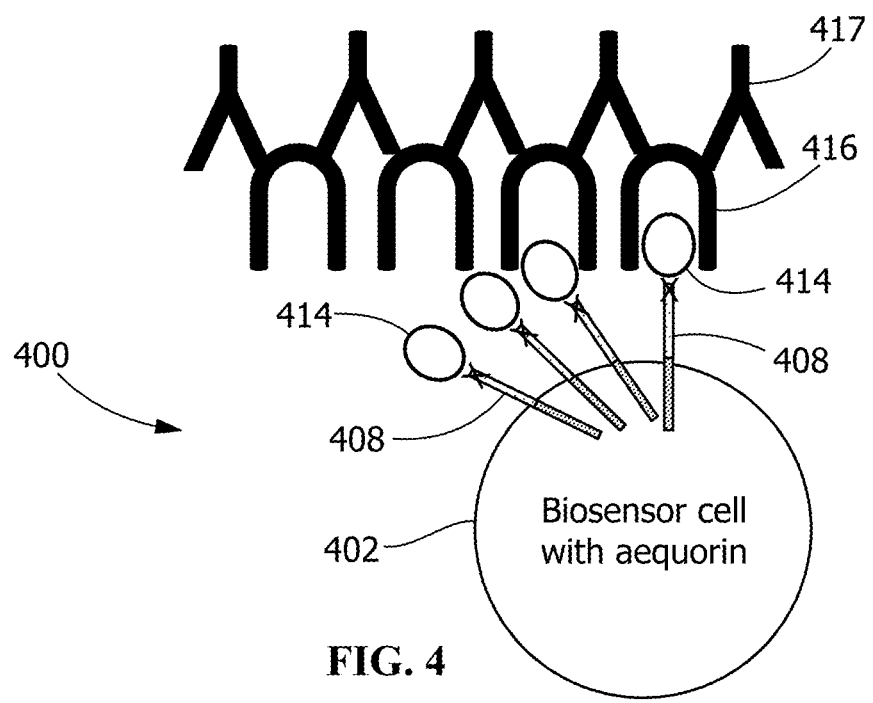
FIG. 4 is an illustration of a fourth biosensor in accordance with an exemplary embodiment of the present invention, wherein biosensor cells have been engineered to produce aequorin and to express the transmembrane non-antibody signal transducing element mSA-CD3ζ, which binds to a biotinylated detector element.

With reference to FIG. 4, a fourth biosensor 400 in accordance with an exemplary embodiment of the present invention includes biosensor cells 402 that have been engineered to produce aequorin and to express transmembrane non-antibody signal transducing element 408, which is mSA-CD3ζ (SEQ ID NO: 17-18). Non-antibody signal transducing element mSA-CD3ζ (monomeric streptavidin-CD3ζ) binds to a biotinylated detector molecule 414, which specifically binds to a target molecule 416 such as, for example, epidermal growth factor (EGF). An anti-target molecule antibody 417 such as, for example, anti-EGF, creates target multimers that cluster multiple signal transducing elements and induce signal transduction as previously described. In other embodiments, the monomeric streptavidin component is replaced with a biotinylated component and alternate linkage means may be employed.

Example Biosensor V

Figure 5:
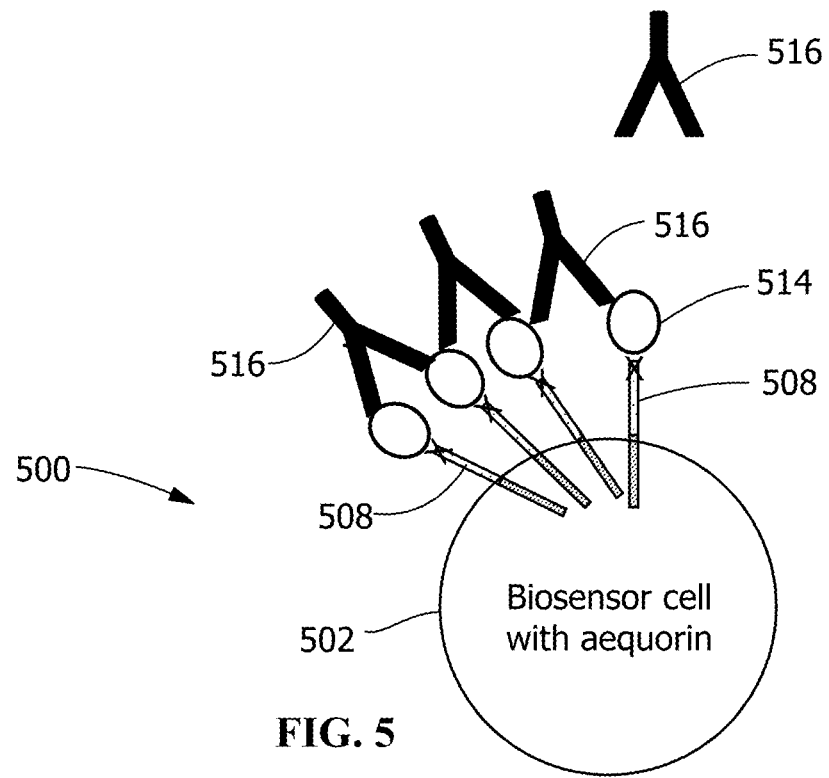
FIG. 5 is an illustration of a fifth biosensor in accordance with an exemplary embodiment of the present invention, wherein biosensor cells have been engineered to produce aequorin and to express the transmembrane non-antibody signal transducing element mSA-CD3ζ, which binds to a biotinylated detector element.

With reference to FIG. 5, a fifth biosensor 500 in accordance with an exemplary embodiment of the present invention includes biosensor cells 502 that have been engineered to produce aequorin and to express transmembrane non-antibody signal transducing element 508, which is mSA-CD3ζ (SEQ ID NO: 17-18). Non-antibody signal transducing element mSA-CD3ζ (monomeric streptavidin-CD3ζ) binds to a biotinylated detector molecule 514, which in some embodiments is an autoantigen molecule. Biotinylated detector molecule 514 specifically binds to a target molecule 516, which in some embodiments is an anti-autoantigen molecule. Autoantibodies in a serum sample create target multimers that cluster multiple signal transducing elements and induce signal transduction as previously described. In other embodiments, the monomeric streptavidin component is replaced with a biotinylated component and alternate linkage means may be employed.

The amino acid sequences of the signal-transducing polypeptide used to produce the chimeric proteins of the invention may have at least 70%, 75%, 80%, 85%, 87.5%, 90%, 92.5%, 95%, 97.5%, 98%, 99% sequence identity or similarity to the proteins or domains identified by or in the following accession numbers: IgM heavy chain (GenBank: CAC20458.1), Ig-alpha (P11912.2, GI: 547896), Ig-beta (P40259.1 GI: 728994), CD19 (AAA69966.1 GI: 901823), CD3zeta (P20963.2, GI: 23830999), IgE alpha (1F2Q_A, GI: 9257150) and Fc-epsilonR1 subunit alpha (P12319.1, GI: 119865).

*Staphylococcus aureus* Protein A (P02976.3, GI: 110283003) is encoded by the spa gene of *Staphylococcus aureus* and its structure, including its Ig-binding segments, and immunoglobulin-binding properties are well-known and are incorporated by reference to Graille, et al., Proc Natl Acad Sci USA. 2000 May 9; 97(10):5399-404; and Roben, et al. J Immunol. 1995 Jun. 15; 154(12):6437-45. Variants of Protein A or its immunoglobulin-binding segments having at least 70%, 75%, 80%, 85%, 87.5%, 90%, 92.5%, 95%, 97.5%, 98%, 99% sequence identity or similarity to known Protein A amino acid sequences and the capacity to bind to an immunoglobulin or other analyte, such as those described by Graille, et al. and Roben, et al., may be produced by molecular biological techniques well-known in the art including by direct synthesis of a nucleic acid encoding an immunoglobulin-binding amino acid sequence.

Other bacterial immunoglobulin-binding proteins, such as *Streptococcus* Protein G and engineered variants of such proteins, are known and are incorporated by reference to Bailey, et al., J Immunol Methods. 2014 Dec. 15; 415:24-30 (doi: 10.1016/j.jim.2014.10.003) (Epub 2014 Oct. 22); and to Watanabe, et al., J Biol Chem. 2009 May 1; 284(18): 12373-8 (doi: 10.1074/jbc.M809236200) (Epub 2009 Mar. 6). Variants of Protein G or its immunoglobulin-binding segments having at least 70%, 75%, 80%, 85%, 87.5%, 90%, 92.5%, 95%, 97.5%, 98%, 99% sequence identity or similarity to known Protein G amino acid sequences and the capacity to bind to an immunoglobulin or other analyte, such as those described by Bailey, et al. and Watanabe, et al. may be produced by molecular biological techniques well-known in the art including by direct synthesis of a nucleic acid encoding an immunoglobulin-binding amino acid sequence.

Fc receptors (FcR) bind to the Fc portion of an immunoglobulin and many types such Fc receptors are known, including FcγRI and FcεRI. The structural and functional binding characteristics of these FcRs are incorporated by reference to Fridman, FASEB J. 1991 September; 5(12): 2684-90. Variants of FcRs or their immunoglobulin-binding segments having at least 70%, 75%, 80%, 85%, 87.5%, 90%, 92.5%, 95%, 97.5%, 98%, 99% sequence identity or similarity to a known FcR amino acid sequence, such as a sequence described by Fridman, may be produced by molecular biological techniques well-known in the art including by direct synthesis of a nucleic acid encoding an immunoglobulin-binding amino acid sequence.

A signal transducing protein according to the invention may have at least 70%, 75%, 80%, 85%, 87.5%, 90%, 92.5%, 95%, 97.5%, 98%, 99% sequence identity or similarity to the disclosed chimeric signal transducing proteins described by SEQ ID NOS: 2, 4, 6, 8, 10, 12, 14, 16, and 18 and also have the ability to bind an analyte, such as an immunoglobulin, and then transduce a signal into the engineered biosensor cell. Such variants may be constructed by methods well known in the molecular biological arts or by chemical synthesis of polynucleotides encoding the variant chimeric reporter proteins, insertion of the encoding sequences into a vector, and transformation or transfection of a competent cell with the vector.

Cell Sorting and Cloning

The design and construction of the biosensors of this invention resulted in a mixed population of biosensor cells when cultured. Some cells did not express the engineered factors while others expressed the factors at varying levels. Following successful electroporation and gene insertion, biosensor cells were cultured and tested for biological response (flash signal) as mixed populations. Single cell sorting was performed using a Flow Cytometer. Cells were isolated and then expanded for analysis to select those that expressed high levels of the desired proteins. For this process, fluorescently labeled antibodies were used to target different receptors on the biosensor cells, thereby enabling the sorting process. Individual clones were screened for signaling and the best clones were selected. Through this process, the most suitable clones were identified and isolated. Fluorescence-Activated Cell Sorting (FACS) and live cell staining for extracellular protein was conducted as described below.

Engineered biosensor cells were counted, gently centrifuged, and re-suspended in wash buffer (HBSS+2% BSA) to a final concentration of $1 \times 10^7$-$1 \times 10^8$ cells/mL. In each experiment, either a full antibody with the Fc region or $F(ab)_2$ was used. When using the full antibody, 1-0.5 μg of Fc receptor blocking antibody was added to each empty 12×15 mm tube that was to receive cells. Into each of these tubes, 100 μL of cells ($1 \times 10^6$ to $1 \times 10^7$ cells) was added on top of the Fc blocking antibody. Cells were mixed gently and incubated for 15 minutes at 4° C. or room temperature. When using $F(ab)_2$, the previous step of blocking Fc was omitted. A total of 1 μg of primary antibody (against the receptor of choice) was added, and the cells were then mixed gently before incubating for 20-40 minutes on ice (or at 4° C.). This temperature prevented receptor internalization. Cells were gently agitated (swirled) intermittently to encourage labeling. A 2 mL volume of cold wash buffer was added then cells were centrifuged at 4° C. and the supernatant discarded. The wash step was repeated before re-suspending cells in 100 μL of wash/sorting buffer. A secondary FITC-labeled antibody was added (0.5-1 μg) to the cells and mixed before incubating on ice (or at 4° C.) for 20-40 minutes. Cells were protected from light during the entire process. A 2 mL volume of cold wash buffer was added then cells centrifuged and supernatant discarded. The wash step was repeated and cells re-suspend in 0.5-1 mL of wash buffer. Cells were incubated on ice until the time for sorting. Sorting was done as soon as possible (at least on the same day). Cloning and culturing cells after single cell sorting was conducted as described below.

Biosensor cells were sorted into 96 well plates with each well containing one cell and 100-200 μL cell growth media. Plates were scanned/monitored for the next 10 to 14 days to determine the rate of growth and to judge when to transfer to a 24 well plate. During scanning, different markings were used for different conditions. Some wells were marked if they contained live cells, but were not ready for transfer and contaminated wells were also marked. Cells were transferred to a 24 well plate containing 1.0 mL of the appropriate media in each well. In cases of contaminated cells, washing was done by adding all of the cell suspension from a well into 5 ml of sterile 1×PBS in a 15 mL conical tube. Cells were then centrifuged at 170 RCF for 10 minutes and the supernatant discarded. The pellet was re-suspended in 1.0 mL of fresh media in a 24 well plate to be cultured. Following continued growth, cells were transferred to a 12 well plate with 1.5 mL of fresh media per well.

For clone screening, after growing in a 12 well plate, cells were counted to determine if they were ready for charging and flash testing. During flash testing, a single iteration involved 25,000 cells. Enough cells were grown to accommodate testing and also leave some to continue growing. This step marked the first round of clone screening. Selected clones were grown further and subjected to subsequent tests depending on the desired properties. For biological response, for example, Jurkat-FcγRI-CD3ζ clones were screened using anti-CD3ε antibodies (positive control) and monoclonal antibodies against bacteria with the respective bacteria while Digitonin was used for chemical response test. MC/9-Aeq clones were screened using anti-FcεRI antibodies (biological response) and Digitonin (chemical response).

In summary, fluorescence-activated cell sorting (FACS) was performed using fluorescent antibody labels to select and isolate cells which were highly expressing the desired proteins, which in this case were the engineered receptors. This process resulted in a population of highly-expressing biosensor cells which was further confirmed by flash testing using the PMT in the testing device. During the entire process, cells were counted using an automatic cell counter to eliminate human error and enhance consistency and efficiency. Different clones of Jurkat-FcγRI-CD3ζ gave different levels of biological response when tested with Anti-*E. coli* O111 mAb and *E. coli* O111 bacteria. Many clones were tested the same way and the highest responders were saved in a clone bank. Likewise, chemical response results obtained from testing different MC/9-Aeq clones using the chemical Digitonin indicated that different clones gave different levels of chemical response depending on the level of Aequorin expression. The clones with the highest signal were saved in the clone bank.

Culturing Biosensor Cells

Different culture media formulations were used for different cell lines to ensure optimal growth conditions. MC/9 mast cells were cultured in Complete Mast Cell Media (DMEM—Sigma, Cat. No. D5796; 1× Pen/Strep; 10% FBS; 10% T-Stim Supplement; 50 µM β-mercaptoethanol). Jurkat T-cells were cultured in complete RPMI media (RPMI-ThermoFisher; 10% FBS; 1× Pen/Strep). Depending on the characteristics of the electroporated constructs, different antibiotics were used for selection in cell culture. Appropriate antibiotics were added to the growth media 2-3 days after electroporation to select for cells that had successfully integrated the linearized DNA constructs. Cell concentration was kept between $4.0 \times 10^5$ and $1.0 \times 10^6$ cells/mL for optimal cell growth. Different cell lines and clones were processed for long term storage and stocks were frozen in liquid nitrogen as follows: (i) cells were centrifuged at 150 RCF for 10 minutes and the supernatant was discarded; (ii) the cell pellet was re-suspended in freezing media (RPMI; 50% FBS; 10% DMSO) at a concentration of $5.0 \times 10^5$ cells/mL; and (iii) volumes of 1 mL were aliquoted into 2 mL Nunc Cryo-vials and frozen at −80° C. for 24 hours before being transferred to liquid nitrogen for long term storage.

Charging Biosensor Cells

The biosensor cells of this invention were centrifuged in 50 mL conical tubes at 150 RCF for 10 minutes. The supernatant was discarded and pellet re-suspended in charging media (RPMI; 10% antibody-depleted FBS; 1× pen/strep; 0.1% Pluronic F68 and 1.5 mM coelenterazine) at a concentration of 25,000 cells/180 µL. Additionally, cells were also been charged at different concentrations such as, for example, 100,000 cells/180 µL and 400,000 cells/180 µL. Cells were charged at room temperature with gentle shaking/rocking for 24-26 hours. Before use, the commercially available antibody-depleted FBS may be purified further using other antibody depletion systems.

Concentrating Cells

The biosensor cells of this invention were demonstrated to be more effectively charged at lower concentrations rather than higher concentrations. For example, charging cells at a density of 25,000 cells/180 µL versus 400,000 cells/180 µL was shown to result in a two-fold increase in detectable signal. Jurkat-FcγRI-CD3ζ clone P5G7 cells were charged at both 400,000 cells/180 µL and 25,000 cells/180 µL then tested at 400,000 cells/180 µL in each reaction. Overnight *E. coli* O111 bacteria culture was used with 23 nM anti-*E. coli* O111 mAb. Biosensor cells charged at a lower concentration gave a higher signal for the same number of bacteria cells tested. Biosensor cell density is mostly changed by concentrating the cells after charging to allow for optimal pathogen detection. Different concentrations were used for pathogen detection depending on the target pathogen and quality of the antibody, when the detector molecule is a soluble antibody. Biosensor cells are concentrated by centrifugation at 150 RCF for 10 minutes and the cell pellet is re-suspended in the desired volume of the testing medium. The charging medium may also serve as the testing medium. In certain instances, addition of normal FBS to the media triggered a biological response resulting in a biosensor signal (flash) due to high concentration of antibodies in normal FBS. Therefore, commercially available antibody-depleted FBS was used in the charging process, which reduced the antibody triggered signal without totally eliminating it. Additional methods were used to further deplete traces of antibodies in the commercially available antibody-depleted FBS.

Bioassay

In exemplary embodiments of this invention, the analyte bioassay is formatted with the biosensor cell and a soluble monoclonal antibody (mAb) that is specific for that analyte (e.g., pathogen). In these embodiments, the specificity of the bioassay is directly related to the selective binding of the soluble antibody to the target analyte and the specificity and sensitivity of the biosensor is determined by detection and measurement of bioluminescence. In this process, biosensor cells are initially charged using the light-emitting molecule, coelenterazine (CTZ). The soluble antibody of choice and the sample being analyzed are then added. If a target pathogen is present in the sample, it interacts with the soluble antibody, which binds to a fusion protein expressed by the biosensor cell, ultimately triggering a signal cascade that results in light emission from the biosensor cell. The emitted light is detected by a photo multiplier tube (PMT) in the testing device and the signal emitted by the biosensor cell is displayed as photon counts per second. As described below, various methods have been developed to detect pathogens based on the soluble antibody and the target pathogen. Three such methods, described in detail below, include: (i) instant addition of detector molecules (e.g., antibodies); (ii) coating biosensor cells with detector molecules (e.g., antibodies); and (iii) coating analytes (e.g., bacteria) with antibodies.

Testing Unit

The bioassay aspect of the present invention herein may be carried out in a testing subunit or test cartridge designed for use with a bench-top or portable testing system and device such as that disclosed in U.S. patent application Ser. No. 13/711,296 (U.S. Pat. No. 9,023,640), which is incorporated by reference herein, in its entirety. The test cartridge, which may be a single-use, disposable item, receives both the sample and the biosensor and introducing the biosensor into the test cartridge mixes the sample and the biosensor in a predictable and controlled manner. The test cartridge further includes a reaction chamber for receiving the test sample and the biosensor, wherein the reaction chamber has a predetermined internal geometry and has been further adapted to minimize or eliminate background noise for the purpose of improving the overall signal to noise ratio. At least one stabilizer may be located in the reaction chamber for minimizing shear force damage to the test sample and biosensor during the mixing process.

In an exemplary embodiment, the reaction chamber and fluid channels that lead to the reaction chamber within the test cartridge are designed to achieve several objectives. An inlet channel for fluid entering the reaction chamber includes a tubular shape and the diameter of the tube is relatively small and tapers to become smaller at the inlet to the reaction chamber. This increases the velocity of fluid entering the reaction chamber and promotes more vigorous and homogenous mixing due to the bulk motion of the reagents within the reaction chamber. It is desirable to mix the reagents and sample in a way to promote mixing beyond molecular diffusion, in order to minimize the duration of the test by ensuring that any infectious agent present in the sample rapidly encounters the biosensor. The inlet channel may be offset from the central axis of the reaction chamber to promote a clockwise or counterclockwise rotational motion of the reagents around the central axis of the test chamber as the fluids are mixed in order to increase homogeneity of the mixture. The inlet channel is also approximately tangent to the interior surface of the reaction chamber for allowing incoming fluid to travel from the inlet channel to the reaction chamber while remaining in contact with the side surface of the reaction chamber, which allows for a minimally turbulent flow and minimal introduction of air bubbles into the mixed fluids. Bubbles are undesirable due to the unpredictable refraction of light they cause as light emitted by the reagents travels through bubbles within the mixed reagents or on the surface of the mixed reagents. The axis of the inlet channel may be angled above horizontal (e.g., about 30 degrees) to provide a partially downward direction to the incoming fluid flow to ensure that the reagent is mixed with the fluid residing at the bottom of the reaction chamber. Alternatively, the reagents may be introduced to the test chamber using alternative fluid delivery means such as a vertical channel to deliver the reagents to the bottom of the reaction chamber, or delivering the fluid directly on the central axis of the test chamber in order to create a column of reagent flowing into the test chamber thereby promoting mixing through entrainment.

The shape (i.e., predetermined geometry) of the reaction chamber may be a revolved section facilitating clockwise or counterclockwise motion of the mixing fluids around the central axis of the reaction chamber. Alternatively, if desired, a reaction chamber shape other than a revolved section such as a rectangular or irregular shape may be utilized. In one embodiment, the revolved section used to form the reaction chamber is a portion of an ellipse for facilitating the collection of stray light emitted by the reagents and reflecting this light toward the surface of the detector, which may be a photomultiplier tube (PMT) (Hamamatsu). The surface of the reaction chamber may be reflective, in order to enhance the light collection properties of the elliptical shape. In some embodiments, the maximum diameter of the surface of the PMT is limited to achieve a maximum signal to noise ratio of the output of the system. The diameter of the reaction chamber may be designed to approximately match the diameter of the PMT, which influences the elliptical shape that can be achieved in a reaction chamber designed to hold a specific volume of fluids. Due to the constrained elliptical shape, the reaction chamber surface color may be a partially diffusing white due to the additional light collection that occurs when light that would not otherwise be reflected directly to the PMT surface is partially diffused by the white surface and a fraction of this is directed toward the PMT surface. Alternatively, other surface finishes and materials such as a near-mirror finish aluminum, or a transparent material could be used if desired. Further, it is desirable for the reaction chamber material to be minimally phosphorescent, in order to prevent light emitted from the reaction chamber itself from eclipsing any emitted light from the reagents and preventing detection. Although white polymeric materials such as acrylonitrile butadiene styrene or other such polymeric materials have been found to exhibit a low level of phosphorescence, the additional light collection provided by the combination of light reflection and diffusion has been found to be a benefit to the signal to noise ratio of the light sensing circuit output.

In an exemplary embodiment, the testing subunit provides a system for use in sample analysis. The system includes a biosensor reagent, wherein the biosensor reagent includes living biological cells; a reservoir card, having a long loop portion and a short loop portion, wherein the reservoir card stores the biosensor reagent; and a test cartridge base, wherein the test cartridge base is configured to accept the reservoir card. The test cartridge base further includes: (i) a reaction chamber having a central axis, wherein the reaction chamber has the shape of a revolved half ellipse; and (ii) an inlet channel connected to the reaction chamber, wherein the inlet channel is positioned above the reaction chamber at an angle of 15-60 degrees above the horizontal, wherein the inlet channel is offset from the central axis of the reaction chamber, and wherein upon introducing a sample to be analyzed into the test cartridge base through the inlet channel, the sample is homogeneously mixed with the biosensor reagent while minimizing damage to the living biological cells.

In another exemplary embodiment, the testing subunit provides a system for rapidly detecting the presence of an analyte in a biological sample. This system includes a biosensor reagent including at least one antibody specific for a predetermined analyte and a bioluminescent agent, wherein the at least one antibody is expressed on the surface of living, engineered lymphocytes and wherein the bioluminescent agent is expressed by the living, engineered lymphocytes, the biosensor reagent being operative to: (i) detect the presence of a specific analyte in a sample to be tested, and (ii) emit a detectable light signal when the biosensor reagent reacts with the sample and detects the presence of the specific analyte in the sample. A test cartridge is also included. The test cartridge further includes: (i) a reservoir card, wherein the reservoir card further includes the biosensor reagent; and (ii) a test cartridge base, wherein the test cartridge base is configured to accept the reservoir card. The test cartridge base further includes: a) a reaction chamber having a central axis, wherein the reaction chamber has the shape of a revolved half ellipse; b) an inlet channel connected to the reaction chamber, wherein the inlet channel is positioned above the reaction chamber at an angle of 15-60 degrees above the horizontal, and wherein the inlet channel is offset from the central axis of the reaction chamber; and c) wherein upon introducing the sample into the test cartridge base through the inlet channel, the sample is homogeneously mixed with the biosensor reagent while minimizing damage to the living, engineered lymphocytes and minimizing any bubbling of the mixed biosensor reagent and sample in the reaction chamber. A testing unit adapted to receive the test cartridge is also included. The testing unit including a sensor for detecting the detectable light signal emitted by the biosensor reagent upon reacting with the sample, the detection of the emitted detectable light signal being indicative of the presence of the analyte in the sample and, wherein detection of the specific analyte in the sample occurs in real time.

Example Bioassay 1: Instant Addition of Antibodies

In an exemplary embodiment of the bioassay of the present invention, wherein the detector molecule is a soluble antibody, the soluble antibody and sample to be tested are mixed together immediately prior introduction of the biosensor cells to the test sample. In this embodiment, charged biosensor cells are centrifuged and concentrated to about 400,000 cells/180 μL (adequate for a single reaction) in the charging medium. A 180 μL (about 400,000 cells) aliquot of the charged biosensor cells is then loaded into the long loop portion of the reservoir card. For a positive control, 30 μL of anti-CD3ε antibody in RPMI media is loaded into the short loop portion of the reservoir card. The reservoir card is then locked into the test cartridge base. A 2 μL volume of an antibody (at 0.5 mg/mL) against the target pathogen, such as anti-*E. coli* O111 (wherein the target pathogen is *E. coli* O111), is mixed with 28 μL of the sample to be tested in the cartridge mixing chamber. The test cartridge base is inserted into the testing device and the charged biosensor cells are injected into the reaction chamber to initiate the reaction. The resulting signal is recorded for 4 to 8 minutes and at the end of the test period, the 30 μL of anti-CD3ε antibody is injected from the short loop of the reservoir into reaction chamber as a positive control reaction that is recorded for 2 minutes. As an alternative positive control, 30 μL of 0.61 mM Digitonin can be used rather than anti-CD3ε antibody. A negative control test can be performed using a predetermined pathogen that is not specific for the antibody being used.

Example Bioassay 2: Coating Biosensor Cells with Antibodies

In another exemplary embodiment of the bioassay of the present invention, wherein the detector molecule is a soluble antibody, the biosensor cells are coated with the soluble antibody for a period of time prior to mixing the sample to be tested with the biosensor cells. In this embodiment, charged biosensor cells are centrifuged and concentrated to about 400,000 cells/180 μL (adequate for one reaction) in the charging medium. A 180 μL (about 400,000 cells) aliquot of the biosensor cells is then mixed with a 2 μL volume of an antibody (at 0.5 mg/mL) against the target pathogen, such as anti-*E. coli* O111 (wherein the target pathogen is *E. coli* O111), in an Eppendorf tube. The biosensor cells mixed with the antibody are incubated at room temperature for 10 minutes and then loaded into the long loop portion of the reservoir card. For a positive control, 30 μL of anti-CD3ε antibody in RPMI media is loaded into the short loop portion of the reservoir card. The reservoir card is then locked into the test cartridge base. A 30 μL volume of the sample to be tested is added into the reaction chamber. The test cartridge base is inserted into the testing device and the biosensor cells are injected into the mixing chamber to initiate the reaction. The resulting signal is recorded for 4 to 8 minutes and at the end of the test period, the 30 μL of anti-CD3ε antibody is injected from the short loop of the reservoir into reaction chamber as a positive control reaction that is recorded for 2 minutes. As an alternative positive control, 30 μL of 0.61 mM Digitonin can be used rather than anti-CD3ε antibody. A negative control test can be performed using a predetermined pathogen that is not specific for the antibody being used.

Example Bioassay 3: Coating Analyte with Antibodies

In another exemplary embodiment of the bioassay of the present invention, wherein the detector molecule is a soluble antibody, the analyte (e.g., pathogenic bacteria) is coated with the soluble antibody for a period of time prior to mixing the sample to be tested with the biosensor. In this embodiment, charged biosensor cells are centrifuged and concentrated to about 400,000 cells/180 μL (adequate for one reaction) in the charging medium. A 180 μL (about 400,000 cells) aliquot of the biosensor cells is loaded into the long loop portion of the reservoir card. For a positive control, 30 μL of anti-CD3ε antibody in RPMI media is loaded into the short loop portion of the reservoir card. The reservoir card is then locked into the cartridge base. A 2 μL volume of an antibody (at 0.5 mg/mL) against the target pathogen, such as anti-*E. coli* O111 (wherein the target pathogen is *E. coli* O111), is mixed with 28 μL of the sample to be tested in an Eppendorf tube. The sample is incubated at room temperature for 10 minutes then added into the cartridge mixing chamber. The cartridge is inserted into the PMT and the biosensor cells are injected into the mixing chamber to initiate the reaction. The resulting signal is recorded for 4 to 8 minutes and at the end of the test period, the 30 μL of anti-CD3ε antibody is injected from the short loop of the reservoir into reaction chamber as a positive control reaction that is recorded for 2 minutes. As an alternative positive control, 30 μL of 0.61 mM Digitonin can be used rather than anti-CD3ε antibody. A negative control test can be performed using a predetermined pathogen that is not specific for the antibody being used.

The exemplary bioassays described herein may include other additives that reduce background noise and enhance signal. Using anti-CD3ε antibody as a positive control, the system has been demonstrated to detect fewer than 10 charged biosensor cells in a mixture of 50,000 uncharged biosensor cells. The biosensor itself has been demonstrated to detect 230 CFU of bacteria in a sample of 30 μL. In the bioassays described above, a proprietary monoclonal antibody (1F11) against *E. coli* O111 bacteria was used to detect *E. coli* O111 bacteria with *E. coli* O157 being used as a negative control. *E. coli* O157 was demonstrated to give negative results, thereby proving the specificity of the system. Numerous commercially available antibodies may also be used with the described bioassay. With regard to the proprietary monoclonal antibody (1F11), antibody analysis and selection of the monoclonal antibody was accomplished as described below.

Antibody production was determined by an ELISA performed in 96-well multiwell plates. Each well was coated with different LPS (*E. coli* O157, *E. coli* O127, *E. coli* O111, *E. coli* O26, *Klebsiella pnuemoniae, Salmonella enterica* and naïve sera) or bacteria cells (*E. coli* O157, *E. coli* O111, *E. coli* 26 and *E. coli* DH5α). Hybridoma supernatant from different clones of mAb O157 or mAb O111 were added to the wells. Horseradish peroxidase-conjugated (HRP) goat anti-mouse IgG was used for detection (Appendix III.A.3). The two hybridoma clones (1B10 and 6G1) of *E. coli* O157 exclusively recognize LPS of *E. coli* O157 and *E. coli* O157.

The nine hybridoma clones of *E. coli* O111 specifically recognize LPS of *E. coli* O111 and *E. coli* O111. The clones from the highest optical density (OD) reading were chosen for validation, which was accomplished as described below.

The hybridoma cell pellets were collected and stored at −80° C. before RNA extraction. The extracted RNA was used as a template for reverse transcription to cDNA, followed by nested PCR amplification. All positive PCR products were cloned into TA cloning vectors and sent for sequencing. The variable regions of the light chain and the heavy chain were determined after analysis of sequences. Four single chain antibodies (scFv) of O157 (1B10) (customized mAb produced by FSC) and ATCC HB 10452, as well as two single chain antibodies of O111 produced by FSC (1F11 and 1F2) were recombinantly expressed and purified by Immobilized metal ion affinity chromatography (IMAC). The sequence of scFv was constructed in the following order: pel B secretion signal+amino acid Alanine+Histidine tag+amino acids Glycine-Serine-Serine-Glycine+TEV cleavage site+amino acids Glycine-Serine-Serine-Glycine+heavy chain variable region+Linker region Serine-Alanine-Aspartic Acid-Aspartic Acid-Alanine-lysine-lysine-Aspartic Acid-Alanine-Alanine-Lysine-Lysine-Aspartic Acid-Aspartic Acid-Alanine-Lysine-Lysine-Aspartic Acid-Aspartic Acid+light chain variable region. The purified scFvs were tested using multi-well plates coated with LPS of O157 or O111.

The purpose of this study was to investigate the interactions of monoclonal antibody (mAb) to whole bacterial cells (*E. coli* O157 or *E. coli* O111), and to estimate the kinetic constant (KD) of antibody-bacterial interaction. In these assays, goat anti-*E. coil* O157 polyclonal antibody, goat anti-*E. coli* O111 polyclonal antibody, three monoclonal antibodies (1022, 1024 and 1061) against *E. coli* O157, and one monoclonal antibody against *E. coli* O111 were used. A CM5 sensor chip and amine coupling kit were also used. All assays were performed on a Biacore X100 instrument. In the protocol, one polyclonal antibody (against a select bacteria) was immobilized onto a CM5 sensor chip. The select bacteria was then bound followed by injection of a monoclonal antibody against the same bacteria in a continuous buffer flow. The interaction was monitored in real time. The relative binding of the antibody to each bacterium was recorded in resonance units (RUs). Results of the BIAcore analysis of binding an *E. coli* O157 specific antibody (mAb FF754) to *E. coli* O157 and *E. coli* O111 indicated that O157 mAb was specific for its target antigen.

While the present invention has been illustrated by the description of exemplary embodiments thereof, and while the embodiments have been described in certain detail, there is no intention to restrict or in any way limit the scope of the appended claims to such detail. Additional advantages and modifications will readily appear to those skilled in the art. Therefore, the invention in its broader aspects is not limited to any of the specific details, representative devices and methods, and/or illustrative examples shown and described. Accordingly, departures may be made from such details without departing from the spirit or scope of the general inventive concept.

---

What is claimed:

1. A system for rapid detection of analytes, comprising:
   (a) a living, engineered biosensor cell, wherein the living, engineered biosensor cell is derived from a cellular component of a mammalian immune system, and wherein the living, engineered biosensor cell expresses a plurality of at least one predetermined type of receptor molecule on the surface thereof;
   (b) a reporter protein, wherein the reporter protein is engineered into and expressed by the living, engineered biosensor cell, and wherein the reporter protein emits a detectable signal in response to certain predetermined cytosolic changes in the living, engineered biosensor cell;
   (c) a signal transduction pathway engineered into or occurring naturally within the living, engineered biosensor cell, wherein the signal transduction pathway controls a biological process within the cytosol of the living, engineered biosensor cell, and wherein the biological process, when it occurs, causes the reporter protein to emit a detectable signal;
   (d) at least one type of detector molecule, wherein each detector molecule is adapted to bind to a specific analyte;
   (e) at least one analyte, wherein the at least one analyte binds to the detector molecule that is specific to that analyte;
   (f) a plurality of soluble non-antibody signal transducing elements, wherein each soluble signal transducing element is adapted to bind to a receptor molecule on the surface of the living, engineered biosensor cell and to a detector molecule, and wherein the receptor molecule is operative to activate the signal transduction pathway engineered into or occurring naturally within the living, engineered biosensor cell; and
   (g) wherein upon the binding of a sufficient number of analytes to a sufficient number of the detector molecules to a sufficient number of the non-antibody signal transducing elements that are themselves bound to the cell surface receptor molecules, an aggregation of the receptor molecules occurs, the signal transduction pathway is activated, the biological process occurs, and the detectable signal is emitted by the reporter protein.

2. The system of claim 1, wherein the biosensor cell is derived from a mast cell.

3. The system of claim 1, wherein the at least one predetermined type of receptor molecule expressed on the surface of the biosensor cell is FcεRI.

4. The system of claim 1, wherein the reporter protein is aequorin and the detectable signal is a flash of blue light.

5. The system of claim 1, wherein the biological process controlled by the signal transduction pathway further includes an increase in intracellular calcium.

6. The system of claim 1, wherein each non-antibody signal transducing element is a soluble chimeric fusion protein that includes a bacterial IgG binding domain fused to an IgE constant domain with a GSASGSG (SEQ ID NO: 19) linker.

7. The system of claim 1, wherein each non-antibody signal transducing element is a soluble chimeric fusion protein that includes an FcγRI antibody binding domain fused to and IgE constant domain with a GSASGSG (SEQ ID NO: 19) linker.

8. The system of claim 1 wherein the non-antibody signal transducing element is encoded by a DNA sequence having at least 95% identity to a DNA sequence selected from the group consisting of SEQ ID NOS: 13 and 15.

9. The system of claim 1, wherein the non-antibody signal transducing element is a chimeric fusion protein having an amino acid sequence selected from the group consisting of SEQ ID NOS: 14 and 16.

10. The system of claim 1, wherein the at least one detector molecule is a soluble antibody.

11. The system of claim 1, wherein the at least one detector molecule is soluble IgG.

12. The system of claim 1, wherein the analyte is a food-borne infectious agent.

13. The system of claim 1, wherein the analyte is either a bacterium or a virus.

14. A method for detecting an analyte, comprising contacting a sample containing the analyte with the system of claim 1 and detecting the analyte when a signal is emitted by the reporter protein.

15. A method for making the system of claim 1, comprising transfecting or transforming an immunocyte with one or more polynucleotides encoding elements (b), (c), and (f) of the system.

* * * * *